United States Patent
Thoren et al.

(10) Patent No.: US 9,877,753 B2
(45) Date of Patent: Jan. 30, 2018

(54) ORTHOPEDIC IMPLANT KIT

(71) Applicant: Wright Medical Technology, Inc., Memphis, TN (US)

(72) Inventors: Brian Thoren, Memphis, TN (US); Ramon Luna, Arlington, TN (US); Christine Petteys, Bartlett, TN (US); Joseph Woodard, Memphis, TN (US); Daniel McCormick, Memphis, TN (US); Kian-Ming (Kevin) Wong, Lakeland, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 15/299,862

(22) Filed: Oct. 21, 2016

(65) Prior Publication Data
US 2017/0035475 A1   Feb. 9, 2017

Related U.S. Application Data

(60) Division of application No. 13/804,228, filed on Mar. 14, 2013, now Pat. No. 9,498,273, which is a (Continued)

(51) Int. Cl.
*A61B 17/88* (2006.01)
*A61F 2/42* (2006.01)
(Continued)

(52) U.S. Cl.
CPC ........ *A61B 17/7291* (2013.01); *A61B 17/862* (2013.01); *A61B 17/8883* (2013.01); (Continued)

(58) Field of Classification Search
CPC .......... A61F 2002/423; A61F 2/4225
See application file for complete search history.

(56) References Cited

U.S. PATENT DOCUMENTS

| 321,389 A | 6/1885 | Schirmer |
|---|---|---|
| 346,148 A | 7/1886 | Durham |

(Continued)

FOREIGN PATENT DOCUMENTS

| CN | 1047025 A | 11/1990 |
|---|---|---|
| CN | 201085677 | 7/2008 |

(Continued)

OTHER PUBLICATIONS

Brochure MKT 016 A: iFuse HT Hammertoe Correction Implant, OrthoPro LLC, 2 pages, undated.
(Continued)

*Primary Examiner* — David Bates
(74) *Attorney, Agent, or Firm* — Duane Morris LLP

(57) ABSTRACT

An implant kit has an adapter having a first end, a second end, and a longitudinal axis extending from the first and to the second end, wherein the first end is configured for removably receiving and engaging an implant and the second end is configured for removably coupling to a driver shaft of an implant driving tool, and an implant preloaded into the first end of the adapter, the implant having an elongated threaded portion; and a blade portion extending from the elongated threaded portion, and having two serrated edges, wherein the blade portion is received in the first end of the adapter and the elongated threaded portion of the implant is coaxially aligned with the longitudinal axis of the adapter.

16 Claims, 43 Drawing Sheets

Related U.S. Application Data continuation-in-part of application No. 13/086,136, filed on Apr. 13, 2011, now Pat. No. 9,072,564.

(60) Provisional application No. 61/350,665, filed on Jun. 2, 2010.

(51) Int. Cl.
 *A61B 17/72* (2006.01)
 *A61B 17/86* (2006.01)
 *A61F 2/30* (2006.01)

(52) U.S. Cl.
 CPC ...... *A61B 17/8886* (2013.01); *A61B 17/8891* (2013.01); *A61F 2002/30622* (2013.01); *A61F 2002/423* (2013.01)

(56) References Cited

U.S. PATENT DOCUMENTS

| | | |
|---|---|---|
| 348,589 A | 9/1886 | Sloan |
| 373,074 A | 11/1887 | Jones |
| 430,236 A | 6/1890 | Rogers |
| 561,968 A | 6/1896 | Coulon |
| 736,121 A | 8/1903 | Lipscomb |
| 821,025 A | 5/1906 | Davies |
| 882,937 A * | 3/1908 | Fegley ............... B25B 13/5091 81/124.2 |
| 1,966,835 A | 7/1934 | Stites |
| 2,140,749 A | 12/1938 | Kaplan |
| 2,361,107 A | 10/1944 | Johnson |
| 2,451,747 A | 10/1948 | Kindt |
| 2,490,364 A | 12/1949 | Livingston |
| 2,600,517 A | 6/1952 | Rushing |
| 2,697,370 A | 12/1954 | Brooks |
| 2,832,245 A | 4/1958 | Burrows |
| 2,895,368 A | 7/1959 | Place |
| 3,462,765 A | 8/1969 | Swanson |
| 3,466,669 A | 9/1969 | Flatt |
| 3,593,342 A | 7/1971 | Niebauer et al. |
| 3,681,786 A | 8/1972 | Lynch |
| 3,739,403 A | 6/1973 | Nicolle |
| 3,759,257 A | 9/1973 | Fischer et al. |
| 3,760,802 A | 9/1973 | Fischer et al. |
| 3,779,239 A | 12/1973 | Fischer et al. |
| 3,824,631 A | 7/1974 | Burstein et al. |
| D243,716 S | 3/1977 | Treace et al. |
| 4,047,524 A | 9/1977 | Hall |
| 4,096,896 A | 6/1978 | Engel |
| 4,156,296 A | 5/1979 | Johnson et al. |
| 4,170,990 A | 10/1979 | Baumgart et al. |
| 4,175,555 A | 11/1979 | Herbert |
| 4,198,713 A | 4/1980 | Swanson |
| 4,204,284 A | 5/1980 | Koeneman |
| 4,213,208 A | 7/1980 | Marne |
| 4,237,875 A | 12/1980 | Termanini |
| 4,262,665 A | 4/1981 | Roalstad et al. |
| 4,263,903 A * | 4/1981 | Griggs ............... A61B 17/0642 227/147 |
| 4,275,717 A | 6/1981 | Bolesky |
| 4,276,660 A | 7/1981 | Laure |
| 4,278,091 A | 7/1981 | Borzone |
| 4,304,011 A | 12/1981 | Whelan, III |
| 4,321,002 A | 3/1982 | Froehlich |
| 4,364,382 A | 12/1982 | Mennen |
| 4,367,562 A | 1/1983 | Gauthier |
| 4,404,874 A | 9/1983 | Lieser |
| 4,434,796 A | 3/1984 | Karapetian et al. |
| 4,454,875 A | 6/1984 | Pratt et al. |
| 4,485,816 A | 12/1984 | Krumme |
| D277,509 S | 2/1985 | Lawrence et al. |
| D277,784 S | 2/1985 | Sgariato et al. |
| 4,516,569 A | 5/1985 | Evans et al. |
| 4,570,623 A | 2/1986 | Ellison et al. |
| 4,590,928 A | 5/1986 | Hunt et al. |
| D284,099 S | 6/1986 | Laporta et al. |
| 4,634,382 A | 1/1987 | Kusano et al. |
| 4,642,122 A | 2/1987 | Stefee |
| 4,655,661 A | 4/1987 | Brandt |
| D291,731 S | 9/1987 | Alkins |
| 4,723,540 A | 2/1988 | Gilmer, Jr. |
| 4,723,541 A | 2/1988 | Reese |
| 4,731,087 A | 3/1988 | Sculco et al. |
| 4,756,711 A | 7/1988 | Mai et al. |
| 4,759,768 A | 7/1988 | Hermann et al. |
| 4,790,304 A | 12/1988 | Rosenberg |
| 4,865,606 A | 9/1989 | Rehder |
| 4,908,031 A | 3/1990 | Frisch |
| 4,915,092 A | 4/1990 | Firica et al. |
| 4,932,974 A | 6/1990 | Pappas et al. |
| 4,940,467 A | 7/1990 | Tronzo |
| 4,955,916 A | 9/1990 | Carignan et al. |
| 4,963,144 A | 10/1990 | Huene |
| 4,969,909 A | 11/1990 | Barouk |
| 5,002,563 A | 3/1991 | Pyka et al. |
| 5,007,932 A | 4/1991 | Bekki et al. |
| 5,011,497 A | 4/1991 | Persson et al. |
| 5,019,079 A | 5/1991 | Ross |
| 5,029,753 A | 7/1991 | Hipon et al. |
| 5,037,440 A | 8/1991 | Koenig |
| 5,046,513 A | 9/1991 | Gatturna et al. |
| 5,047,059 A | 9/1991 | Saffar |
| 5,053,038 A | 10/1991 | Sheehan |
| 5,059,193 A | 10/1991 | Kuslich |
| 5,062,851 A | 11/1991 | Branemark |
| 5,089,009 A | 2/1992 | Green |
| 5,092,896 A | 3/1992 | Meuli et al. |
| 5,108,395 A | 4/1992 | Laurain |
| 5,133,761 A | 7/1992 | Krouskop |
| 5,147,363 A | 9/1992 | Harle |
| 5,171,252 A | 12/1992 | Friedland |
| 5,179,915 A | 1/1993 | Cohen et al. |
| 5,190,546 A | 3/1993 | Jervis |
| 5,199,839 A | 4/1993 | DeHaitre |
| 5,207,712 A | 5/1993 | Cohen |
| 5,209,756 A | 5/1993 | Seedhom et al. |
| 5,213,347 A | 5/1993 | Rulon et al. |
| 5,222,975 A | 6/1993 | Crainich |
| 5,246,443 A | 9/1993 | Mai |
| 5,281,225 A | 1/1994 | Vicenzi |
| 5,304,204 A | 4/1994 | Bregen |
| 5,324,307 A | 6/1994 | Jarrett et al. |
| 5,326,364 A | 7/1994 | Clift, Jr. et al. |
| 5,326,366 A | 7/1994 | Pascarella et al. |
| 5,330,476 A | 7/1994 | Hiot et al. |
| 5,342,396 A | 8/1994 | Cook |
| 5,352,229 A | 10/1994 | Goble et al. |
| 5,354,301 A | 10/1994 | Catellano |
| 5,358,405 A | 10/1994 | Imai |
| 5,360,450 A | 11/1994 | Giannini |
| 5,366,479 A | 11/1994 | McGarry et al. |
| 5,380,334 A | 1/1995 | Torrie et al. |
| 5,395,372 A | 3/1995 | Holt et al. |
| 5,405,400 A | 4/1995 | Linscheid et al. |
| 5,405,401 A | 4/1995 | Lippincott, III et al. |
| 5,417,692 A | 5/1995 | Goble et al. |
| 5,425,776 A | 6/1995 | Cohen |
| 5,425,777 A | 6/1995 | Sarkisian et al. |
| 5,437,674 A | 8/1995 | Worcel et al. |
| 5,449,359 A | 9/1995 | Groiso |
| 5,454,814 A | 10/1995 | Comte |
| 5,458,648 A | 10/1995 | Berman et al. |
| 5,470,230 A | 11/1995 | Daftary et al. |
| 5,474,557 A | 12/1995 | Mai |
| 5,480,447 A | 1/1996 | Skiba |
| 5,484,443 A | 1/1996 | Pascarella et al. |
| 5,498,265 A | 3/1996 | Asnis et al. |
| 5,507,822 A | 4/1996 | Bouchon et al. |
| 5,516,248 A | 5/1996 | DeHaitre |
| 5,522,903 A | 6/1996 | Sokolow et al. |
| 5,529,075 A | 6/1996 | Clark |
| 5,536,127 A | 7/1996 | Pennig |
| 5,549,681 A | 8/1996 | Segmüller et al. |
| 5,551,871 A | 9/1996 | Besselink et al. |

(56) References Cited

U.S. PATENT DOCUMENTS

| | | |
|---|---|---|
| 5,554,157 A | 9/1996 | Errico et al. |
| 5,578,034 A | 11/1996 | Estes |
| 5,591,165 A | 1/1997 | Jackson |
| 5,595,563 A | 1/1997 | Moisdon |
| 5,601,558 A | 2/1997 | Torrie et al. |
| D378,409 S | 3/1997 | Michelson |
| 5,634,925 A | 6/1997 | Urbanski |
| 5,643,264 A | 7/1997 | Sherman et al. |
| 5,645,599 A | 7/1997 | Samani |
| 5,660,188 A | 8/1997 | Groiso |
| 5,669,913 A | 9/1997 | Zobel |
| 5,674,297 A | 10/1997 | Lane et al. |
| 5,683,466 A | 11/1997 | Vitale |
| 5,690,629 A | 11/1997 | Asher et al. |
| 5,702,472 A | 12/1997 | Huebner |
| 5,707,395 A | 1/1998 | Li |
| 5,713,903 A | 2/1998 | Sander et al. |
| 5,713,904 A | 2/1998 | Errico et al. |
| 5,720,753 A | 2/1998 | Sander et al. |
| 5,725,585 A | 3/1998 | Zobel |
| 5,728,127 A | 3/1998 | Asher et al. |
| 5,733,307 A | 3/1998 | Dinsdale |
| 5,741,256 A | 4/1998 | Bresina |
| 5,749,916 A | 5/1998 | Richelsoph |
| 5,769,852 A | 6/1998 | Brånemark |
| 5,776,202 A | 7/1998 | Copf et al. |
| 5,779,707 A | 7/1998 | Bertholet et al. |
| 5,782,927 A | 7/1998 | Klawittler et al. |
| 5,785,713 A | 7/1998 | Jobe |
| 5,840,078 A | 11/1998 | Yerys |
| 5,853,414 A | 12/1998 | Groiso |
| 5,876,434 A | 3/1999 | Flomenblit et al. |
| 5,882,444 A | 3/1999 | Flomenblit et al. |
| 5,893,850 A | 4/1999 | Cachia |
| 5,919,193 A | 7/1999 | Slavitt |
| 5,928,236 A | 7/1999 | Augagneur et al. |
| 5,941,890 A | 8/1999 | Voegele et al. |
| 5,951,288 A | 9/1999 | Sawa |
| 5,958,159 A | 9/1999 | Prandi |
| 5,980,524 A | 11/1999 | Justin et al. |
| 5,984,970 A | 11/1999 | Bramlet |
| 5,984,971 A | 11/1999 | Faccioli et al. |
| 6,011,497 A | 1/2000 | Tsang et al. |
| 6,017,366 A | 1/2000 | Berman |
| 6,030,162 A | 2/2000 | Huebner |
| 6,045,573 A | 4/2000 | Wenstrom, Jr. et al. |
| 6,048,151 A | 4/2000 | Kwee |
| 6,048,343 A | 4/2000 | Mathis et al. |
| 6,083,242 A | 7/2000 | Cook |
| 6,099,571 A | 8/2000 | Knapp |
| 6,102,642 A | 8/2000 | Kawashita et al. |
| 6,146,387 A | 11/2000 | Trott et al. |
| 6,187,009 B1 | 2/2001 | Herzog et al. |
| 6,193,757 B1 | 2/2001 | Foley et al. |
| 6,197,037 B1 | 3/2001 | Hair |
| 6,200,321 B1 | 3/2001 | Orbay et al. |
| 6,200,330 B1 | 3/2001 | Benderev et al. |
| 6,200,345 B1 | 3/2001 | Morgan |
| 6,224,600 B1 | 5/2001 | Protogirou |
| 6,248,109 B1 | 6/2001 | Stofella |
| 6,299,613 B1 | 10/2001 | Ogilvie et al. |
| 6,305,053 B1 | 10/2001 | Galbreath |
| 6,306,140 B1 | 10/2001 | Siddiqui |
| 6,319,284 B1 | 11/2001 | Rushdy et al. |
| 6,332,885 B1 | 12/2001 | Martella |
| 6,336,928 B1 | 1/2002 | Guerin et al. |
| 6,352,560 B1 | 3/2002 | Poeschmann et al. |
| 6,383,223 B1 | 5/2002 | Baehler et al. |
| 6,386,877 B1 | 5/2002 | Sutter |
| 6,406,234 B2 | 6/2002 | Frigg |
| 6,413,260 B1 | 7/2002 | Berrevoets et al. |
| 6,419,706 B1 | 7/2002 | Graf |
| 6,423,097 B2 | 7/2002 | Rauscher |
| 6,428,634 B1 | 8/2002 | Besselink et al. |
| 6,436,099 B1 | 8/2002 | Drewry et al. |
| 6,451,057 B1 | 9/2002 | Chen et al. |
| 6,454,808 B1 | 9/2002 | Masada |
| 6,458,134 B1 | 10/2002 | Songer et al. |
| 6,475,242 B1 | 11/2002 | Bramlet |
| 6,508,841 B2 | 1/2003 | Martin et al. |
| 6,517,543 B1 | 2/2003 | Berrevoets et al. |
| 6,533,788 B1 | 3/2003 | Orbay |
| 6,551,321 B1 | 4/2003 | Burkinshaw |
| 6,551,343 B1 | 4/2003 | Törmälä et al. |
| 6,575,973 B1 | 6/2003 | Shekalim |
| 6,575,976 B2 | 6/2003 | Grafton |
| 6,582,453 B1 | 6/2003 | Tran et al. |
| 6,648,890 B2 | 11/2003 | Culbert et al. |
| 6,679,668 B2 | 1/2004 | Martin et al. |
| 6,682,565 B1 | 1/2004 | Krishnan |
| 6,685,706 B2 | 2/2004 | Padget et al. |
| 6,699,247 B2 | 3/2004 | Zucherman et al. |
| 6,699,292 B2 | 3/2004 | Ogilvie et al. |
| 6,706,045 B2 | 3/2004 | Lin et al. |
| 6,767,350 B1 | 7/2004 | Lob |
| 6,773,437 B2 | 8/2004 | Ogilvie et al. |
| 6,811,568 B2 | 11/2004 | Minamikawa |
| 6,869,449 B2 | 3/2005 | Ball et al. |
| 6,875,235 B2 | 4/2005 | Ferree |
| 7,037,309 B2 | 5/2006 | Weil et al. |
| 7,037,324 B2 | 5/2006 | Martinek |
| 7,037,342 B2 | 5/2006 | Nilsson et al. |
| 7,041,106 B1 | 5/2006 | Carver et al. |
| 7,044,953 B2 | 5/2006 | Capanni |
| 7,112,214 B2 | 9/2006 | Peterson et al. |
| 7,182,787 B2 | 2/2007 | Hassler et al. |
| 7,192,445 B2 | 3/2007 | Ellingsen et al. |
| 7,207,994 B2 | 4/2007 | Vlahos et al. |
| 7,240,677 B2 | 7/2007 | Fox |
| 7,261,716 B2 | 8/2007 | Strobel |
| 7,291,175 B1 | 11/2007 | Gordon |
| 7,569,061 B2 | 8/2009 | Colleran |
| 7,585,316 B2 | 9/2009 | Trieu |
| 7,588,603 B2 | 9/2009 | Leonard |
| 7,695,471 B2 | 4/2010 | Cheung et al. |
| 7,708,759 B2 | 5/2010 | Lubbers et al. |
| 7,727,235 B2 | 6/2010 | Contiliano et al. |
| 7,780,701 B1 | 8/2010 | Meridew et al. |
| 7,780,737 B2 | 8/2010 | Bonnard et al. |
| 7,785,357 B2 | 8/2010 | Guan et al. |
| 7,837,738 B2 | 11/2010 | Reigstad et al. |
| 7,842,091 B2 | 11/2010 | Johnstone et al. |
| 7,887,589 B2 | 2/2011 | Glenn et al. |
| 7,909,880 B1 | 3/2011 | Grant |
| 7,918,879 B2 | 4/2011 | Yeung et al. |
| 7,959,681 B2 | 6/2011 | Lavi |
| 7,963,995 B2 | 6/2011 | Richelsoph |
| 7,976,565 B1 | 7/2011 | Meridew |
| 7,985,246 B2 | 7/2011 | Trieu |
| 8,002,811 B2 | 8/2011 | Corradi et al. |
| 8,057,524 B2 | 11/2011 | Meridew |
| 8,100,983 B2 | 1/2012 | Schulte |
| 8,118,839 B2 | 2/2012 | Taylor |
| 8,118,849 B2 | 2/2012 | Wahl et al. |
| 8,197,509 B2 | 6/2012 | Contiliano et al. |
| 8,262,712 B2 | 9/2012 | Coilard-Lavirotte et al. |
| 8,267,939 B2 | 9/2012 | Cipoletti et al. |
| 8,337,537 B2 | 12/2012 | Pelo et al. |
| 8,394,097 B2 | 3/2013 | Peyrot et al. |
| 8,394,132 B2 | 3/2013 | Lewis et al. |
| 8,414,583 B2 | 4/2013 | Prandi et al. |
| 8,465,525 B2 | 6/2013 | Hawkins et al. |
| 8,475,456 B2 | 7/2013 | Augoyard et al. |
| 8,523,944 B2 | 9/2013 | Jiminez et al. |
| 8,591,545 B2 | 11/2013 | Lunn et al. |
| 8,608,785 B2 | 12/2013 | Reed et al. |
| 8,616,091 B2 | 12/2013 | Anderson |
| 8,636,457 B2 | 1/2014 | Connors |
| 8,641,769 B2 | 2/2014 | Malandain |
| 8,647,390 B2 | 2/2014 | Bellemere et al. |
| 8,764,842 B2 | 7/2014 | Graham |
| 8,840,677 B2 | 9/2014 | Kale et al. |
| 8,888,779 B2 | 11/2014 | Senn |
| D720,072 S | 12/2014 | Cheney et al. |

(56) References Cited

U.S. PATENT DOCUMENTS

| | | |
|---|---|---|
| 8,906,060 B2 | 12/2014 | Hart |
| 8,986,386 B2 | 3/2015 | Oglaza et al. |
| 8,998,999 B2 | 4/2015 | Lewis et al. |
| 9,044,287 B2 | 6/2015 | Reed et al. |
| 9,056,014 B2 | 6/2015 | McCormick et al. |
| 9,125,704 B2 | 9/2015 | Reed et al. |
| 9,138,274 B1 | 9/2015 | Biesinger et al. |
| 9,149,268 B2 | 10/2015 | Graul et al. |
| 9,474,561 B2 | 10/2016 | Shemwell |
| 2001/0025199 A1 | 9/2001 | Rauscher |
| 2001/0028836 A1 | 10/2001 | Kohori |
| 2001/0049529 A1 | 12/2001 | Cachia et al. |
| 2002/0019636 A1 | 2/2002 | Ogilvie et al. |
| 2002/0022887 A1 | 2/2002 | Huene |
| 2002/0026194 A1 | 2/2002 | Morrison et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0072803 A1 | 6/2002 | Saunders et al. |
| 2002/0082705 A1 | 6/2002 | Bouman et al. |
| 2002/0111690 A1 | 8/2002 | Hyde |
| 2002/0128713 A1 | 9/2002 | Ferree |
| 2002/0165544 A1 | 11/2002 | Perren et al. |
| 2002/0183846 A1 | 12/2002 | Kuslich et al. |
| 2003/0032961 A1 | 2/2003 | Pelo et al. |
| 2003/0040805 A1 | 2/2003 | Minamikawa |
| 2003/0069645 A1 | 4/2003 | Ball et al. |
| 2003/0130660 A1 | 7/2003 | Levy et al. |
| 2003/0191422 A1 | 10/2003 | Sossong |
| 2003/0233095 A1 | 12/2003 | Urbanski et al. |
| 2004/0010315 A1 | 1/2004 | Song |
| 2004/0093081 A1 | 5/2004 | Nilsson et al. |
| 2004/0097941 A1 | 5/2004 | Weiner et al. |
| 2004/0102853 A1 | 5/2004 | Boumann et al. |
| 2004/0111117 A1 | 6/2004 | Colleran et al. |
| 2004/0133204 A1 | 7/2004 | Davies |
| 2004/0138756 A1 | 7/2004 | Reeder |
| 2004/0220574 A1 | 11/2004 | Pelo et al. |
| 2004/0220678 A1 | 11/2004 | Chow et al. |
| 2004/0230193 A1 | 11/2004 | Cheung et al. |
| 2004/0230194 A1 | 11/2004 | Urbanski et al. |
| 2004/0230313 A1 | 11/2004 | Saunders |
| 2004/0249461 A1 | 12/2004 | Ferree |
| 2005/0113836 A1 | 5/2005 | Lozier et al. |
| 2005/0119757 A1 | 6/2005 | Hassler et al. |
| 2005/0123672 A1 | 6/2005 | Justin et al. |
| 2005/0124443 A1 | 6/2005 | Summers |
| 2005/0149031 A1 | 7/2005 | Ciccone et al. |
| 2005/0177158 A1 | 8/2005 | Doubler et al. |
| 2005/0187636 A1 | 8/2005 | Graham |
| 2005/0251265 A1 | 11/2005 | Calandruccio et al. |
| 2005/0261768 A1 | 11/2005 | Trieu |
| 2005/0283159 A1 | 12/2005 | Amara |
| 2006/0052725 A1 | 3/2006 | Santilli |
| 2006/0052878 A1 | 3/2006 | Schmieding |
| 2006/0074421 A1 | 4/2006 | Bickley et al. |
| 2006/0074488 A1 | 4/2006 | Abdou |
| 2006/0074492 A1 | 4/2006 | Frey |
| 2006/0084998 A1 | 4/2006 | Levy et al. |
| 2006/0100715 A1 | 5/2006 | De Villiers |
| 2006/0129153 A1 | 6/2006 | Klaue et al. |
| 2006/0149258 A1 | 7/2006 | Sousa |
| 2006/0173462 A1 | 8/2006 | Kay et al. |
| 2006/0200151 A1 | 9/2006 | Ducharme et al. |
| 2006/0229617 A1 | 10/2006 | Meller et al. |
| 2006/0247787 A1 | 11/2006 | Rydell et al. |
| 2007/0038303 A1 | 2/2007 | Myerson et al. |
| 2007/0078518 A1 | 4/2007 | Lavi |
| 2007/0106283 A1 | 5/2007 | Garcia et al. |
| 2007/0123873 A1 | 5/2007 | Czartoski et al. |
| 2007/0123993 A1 | 5/2007 | Hassler et al. |
| 2007/0142920 A1 | 6/2007 | Niemi |
| 2007/0177959 A1 | 8/2007 | Chopp et al. |
| 2007/0185583 A1 | 8/2007 | Branemark |
| 2007/0185584 A1 | 8/2007 | Kaufmann et al. |
| 2007/0198018 A1 | 8/2007 | Biedermann et al. |
| 2007/0213831 A1 | 9/2007 | de Cubber |
| 2007/0239158 A1 | 10/2007 | Trieu et al. |
| 2007/0293866 A1 | 12/2007 | Stroeckel et al. |
| 2008/0039949 A1 | 2/2008 | Meesenburg et al. |
| 2008/0051912 A1 | 2/2008 | Hollawell |
| 2008/0086139 A1 | 4/2008 | Bourke et al. |
| 2008/0132894 A1 | 6/2008 | Coilard-Lavirotte et al. |
| 2008/0132958 A1 | 6/2008 | Pech et al. |
| 2008/0154385 A1 | 6/2008 | Trail et al. |
| 2008/0161919 A1 | 7/2008 | Melkent |
| 2008/0177262 A1 | 7/2008 | Augoyard et al. |
| 2008/0177291 A1 | 7/2008 | Jensen et al. |
| 2008/0177334 A1 | 7/2008 | Stinnette |
| 2008/0195215 A1 | 8/2008 | Morton |
| 2008/0195219 A1 | 8/2008 | Wiley et al. |
| 2008/0221574 A1 | 9/2008 | Cavallazzi |
| 2008/0221697 A1 | 9/2008 | Graser |
| 2008/0221698 A1 | 9/2008 | Berger |
| 2008/0255618 A1 | 10/2008 | Fisher et al. |
| 2008/0269908 A1 | 10/2008 | Warburton |
| 2008/0294204 A1 | 11/2008 | Chirico et al. |
| 2009/0005782 A1 | 1/2009 | Chirico et al. |
| 2009/0012564 A1 | 1/2009 | Chirico et al. |
| 2009/0036893 A1 | 2/2009 | Kartalian et al. |
| 2009/0149891 A1 | 6/2009 | Lee et al. |
| 2009/0163918 A1 | 6/2009 | Levy et al. |
| 2009/0187219 A1 | 7/2009 | Pachtman et al. |
| 2009/0204158 A1 | 8/2009 | Sweeney |
| 2009/0210016 A1 | 8/2009 | Champagne et al. |
| 2009/0216282 A1 | 8/2009 | Blake et al. |
| 2009/0254189 A1 | 10/2009 | Scheker |
| 2009/0254190 A1 | 10/2009 | Gannoe et al. |
| 2009/0259316 A1 | 10/2009 | Ginn et al. |
| 2010/0010637 A1 | 1/2010 | Pequignot |
| 2010/0016982 A1 | 1/2010 | Solomons |
| 2010/0023012 A1 | 1/2010 | Voor |
| 2010/0030221 A1 | 2/2010 | Christian et al. |
| 2010/0049244 A1 | 2/2010 | Cohen et al. |
| 2010/0057214 A1 | 3/2010 | Graham et al. |
| 2010/0061825 A1 | 3/2010 | Liu et al. |
| 2010/0069913 A1 | 3/2010 | Chirico |
| 2010/0069970 A1 | 3/2010 | Lewis et al. |
| 2010/0121390 A1 | 5/2010 | Kleinman |
| 2010/0125274 A1 | 5/2010 | Greenhalgh et al. |
| 2010/0131014 A1 | 5/2010 | Peyrot et al. |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0217325 A1 | 8/2010 | Hochschuler et al. |
| 2010/0249942 A1 | 9/2010 | Goswami et al. |
| 2010/0256639 A1 | 10/2010 | Tyber et al. |
| 2010/0256770 A1 | 10/2010 | Hakansson et al. |
| 2010/0262254 A1 | 10/2010 | Lawrence et al. |
| 2010/0274293 A1 | 10/2010 | Terrill et al. |
| 2010/0286692 A1 | 11/2010 | Greenhalgh et al. |
| 2010/0292799 A1 | 11/2010 | Hansell et al. |
| 2010/0324556 A1 | 12/2010 | Tyber et al. |
| 2010/0331893 A1 | 12/2010 | Geist et al. |
| 2011/0004255 A1 | 1/2011 | Weiner et al. |
| 2011/0004317 A1 | 1/2011 | Hacking et al. |
| 2011/0066190 A1 | 3/2011 | Schaller et al. |
| 2011/0082507 A1 | 4/2011 | Klaue |
| 2011/0082508 A1 | 4/2011 | Reed |
| 2011/0093017 A1 | 4/2011 | Prasad et al. |
| 2011/0093075 A1 | 4/2011 | Duplessis et al. |
| 2011/0093085 A1 | 4/2011 | Morton |
| 2011/0118739 A1 | 5/2011 | Tyber et al. |
| 2011/0144644 A1 | 6/2011 | Prandi et al. |
| 2011/0144766 A1 | 6/2011 | Kale et al. |
| 2011/0208252 A1 | 8/2011 | Erhart |
| 2011/0257652 A1 | 10/2011 | Roman |
| 2011/0301652 A1 | 12/2011 | Reed et al. |
| 2011/0301653 A1 | 12/2011 | Reed et al. |
| 2011/0306975 A1 | 12/2011 | Kaikkonen et al. |
| 2011/0319946 A1 | 12/2011 | Levy et al. |
| 2012/0016428 A1 | 1/2012 | White et al. |
| 2012/0065692 A1 | 3/2012 | Champagne et al. |
| 2012/0065738 A1 | 3/2012 | Schulman |

(56) References Cited

U.S. PATENT DOCUMENTS

| | | |
|---|---|---|
| 2012/0089197 A1 | 4/2012 | Anderson |
| 2012/0136448 A1 | 5/2012 | Seifert et al. |
| 2012/0209337 A1 | 8/2012 | Weinstein |
| 2012/0259419 A1 | 10/2012 | Brown et al. |
| 2012/0271362 A1 | 10/2012 | Martineau et al. |
| 2012/0323241 A1 | 12/2012 | McClellan et al. |
| 2013/0030475 A1 | 1/2013 | Weiner et al. |
| 2013/0053975 A1 | 2/2013 | Reed et al. |
| 2013/0060295 A1 | 3/2013 | Reed et al. |
| 2013/0066383 A1* | 3/2013 | Anderson .......... A61B 17/7233 606/329 |
| 2013/0066435 A1 | 3/2013 | Averous et al. |
| 2013/0079776 A1 | 3/2013 | Zwirkoski et al. |
| 2013/0090655 A1 | 4/2013 | Tontz |
| 2013/0096634 A1 | 4/2013 | Suh |
| 2013/0123862 A1 | 5/2013 | Anderson et al. |
| 2013/0131822 A1 | 5/2013 | Lewis et al. |
| 2013/0150965 A1 | 6/2013 | Taylor et al. |
| 2013/0190761 A1 | 7/2013 | Prandi et al. |
| 2013/0211451 A1 | 8/2013 | Wales et al. |
| 2013/0226191 A1 | 8/2013 | Thoren et al. |
| 2013/0253597 A1 | 9/2013 | Augoyard et al. |
| 2013/0274814 A1* | 10/2013 | Weiner ................ A61B 17/1682 606/301 |
| 2013/0317559 A1 | 11/2013 | Leavitts et al. |
| 2013/0317599 A1 | 11/2013 | Michal et al. |
| 2013/0325138 A1 | 12/2013 | Graham |
| 2014/0018930 A1 | 1/2014 | Oster |
| 2014/0025125 A1 | 1/2014 | Sack et al. |
| 2014/0052196 A1 | 2/2014 | McGinley et al. |
| 2014/0107713 A1 | 4/2014 | Pech et al. |
| 2014/0135768 A1 | 5/2014 | Roman |
| 2014/0142715 A1 | 5/2014 | McCormick |
| 2014/0180428 A1 | 6/2014 | McCormick |
| 2014/0188179 A1 | 7/2014 | McCormick |
| 2014/0188237 A1 | 7/2014 | McCormick et al. |
| 2014/0188239 A1 | 7/2014 | Cummings |
| 2014/0257289 A1 | 9/2014 | Kecman et al. |
| 2014/0276825 A1 | 9/2014 | Brown et al. |
| 2014/0277185 A1 | 9/2014 | Boileau et al. |
| 2014/0277186 A1 | 9/2014 | Granberry et al. |
| 2015/0012098 A1 | 1/2015 | Eastlack et al. |
| 2015/0018954 A1 | 1/2015 | Loebl et al. |
| 2015/0073413 A1 | 3/2015 | Palmer et al. |
| 2015/0088136 A1 | 3/2015 | Vitek et al. |
| 2015/0088266 A1 | 3/2015 | Sander et al. |
| 2015/0094778 A1 | 4/2015 | McCormick et al. |
| 2015/0112342 A1 | 4/2015 | Penzimer et al. |
| 2015/0141994 A1 | 5/2015 | Cheney et al. |
| 2015/0142066 A1 | 5/2015 | Shemwell et al. |
| 2015/0164563 A1 | 6/2015 | Lewis et al. |
| 2015/0223848 A1 | 8/2015 | McCormick et al. |
| 2015/0223849 A1 | 8/2015 | McCormick et al. |
| 2015/0342655 A1 | 12/2015 | Reed et al. |

FOREIGN PATENT DOCUMENTS

| | | |
|---|---|---|
| EP | 0127994 | 12/1984 |
| EP | 0340159 A1 | 11/1989 |
| EP | 0409364 A2 | 1/1991 |
| EP | 0545830 | 6/1993 |
| EP | 0551846 A1 | 7/1993 |
| EP | 0611557 A3 | 8/1994 |
| EP | 0738502 A2 | 10/1996 |
| EP | 880950 A1 | 12/1998 |
| EP | 1300122 | 4/2003 |
| EP | 1825826 A1 | 8/2007 |
| EP | 1870050 A2 | 12/2007 |
| EP | 1708653 B1 | 9/2009 |
| EP | 2156795 A1 | 2/2010 |
| EP | 1923012 B1 | 6/2010 |
| EP | 1868536 B1 | 11/2010 |
| EP | 2275055 B1 | 5/2012 |
| EP | 2221025 B1 | 12/2012 |
| EP | 2221026 B1 | 3/2013 |
| EP | 2564799 A1 | 3/2013 |
| EP | 2774556 A1 | 9/2014 |
| FR | 736058 | 11/1932 |
| FR | 1036978 | 9/1953 |
| FR | 2603794 | 3/1988 |
| FR | 2605878 A1 | 5/1988 |
| FR | 2628312 | 9/1989 |
| FR | 2645735 A1 | 10/1990 |
| FR | 2651119 A1 | 3/1991 |
| FR | 2663838 A1 | 1/1993 |
| FR | 2694696 | 2/1994 |
| FR | 2725126 | 4/1996 |
| FR | 2743490 | 7/1997 |
| FR | 2754702 | 4/1998 |
| FR | 2783702 A1 | 3/2000 |
| FR | 2787313 A1 | 6/2000 |
| FR | 2794019 A1 | 12/2000 |
| FR | 2801189 A1 | 5/2001 |
| FR | 2808182 B1 | 10/2002 |
| FR | 2846545 A1 | 5/2004 |
| FR | 2728779 A1 | 7/2005 |
| FR | 2884406 | 10/2006 |
| FR | 2927529 | 8/2009 |
| FR | 2935601 A1 | 3/2010 |
| GB | 140983 | 4/1920 |
| GB | 2119655 A | 11/1983 |
| GB | 2227540 A | 8/1990 |
| GB | 2336415 A | 10/1999 |
| GB | 2430625 A | 4/2007 |
| JP | S53-128181 A | 11/1978 |
| JP | 60145133 | 7/1985 |
| JP | H07-500520 A | 1/1995 |
| JP | 07303662 | 11/1995 |
| JP | 2004535249 | 11/2004 |
| JP | 2007530194 | 11/2007 |
| JP | 2008-188411 A | 8/2008 |
| JP | 2009-160399 A | 7/2009 |
| JP | 2010-046481 A | 3/2010 |
| JP | 2011-502584 A | 1/2011 |
| JP | 2011-525229 A | 9/2011 |
| SU | 1152582 | 4/1985 |
| WO | WO 92/17122 | 10/1992 |
| WO | WO 96/41596 A1 | 12/1996 |
| WO | WO 98/17189 | 4/1998 |
| WO | WO 98/47449 A1 | 10/1998 |
| WO | WO 99/21515 A1 | 5/1999 |
| WO | WO 01/80751 A1 | 11/2001 |
| WO | WO 2002/034107 A2 | 5/2002 |
| WO | WO 2005/063149 | 7/2005 |
| WO | WO 2005/094706 A1 | 10/2005 |
| WO | WO 2005/104961 | 11/2005 |
| WO | WO 2006/109004 A1 | 10/2006 |
| WO | WO 2006103598 A1 | 10/2006 |
| WO | WO 2007/048038 | 4/2007 |
| WO | WO 2007/135322 A1 | 11/2007 |
| WO | WO 2009/155577 A2 | 12/2009 |
| WO | WO 2013/096746 A1 | 6/2013 |
| WO | WO 2013/131974 A1 | 9/2013 |
| WO | WO 2014/165123 A1 | 10/2014 |

OTHER PUBLICATIONS

Brochure p/n 030-1788 Rev A: ExtremiFuse Hammertoe Fixation System, OsteoMED Smalll Bone Orthopedics, 6 pages, undated.

Brochure 900-01-008 Rev C: Hammer Toe Implant System Instructions for Use, Trilliant Surgical Ltd, 2 pages, undated.

Japanese Patent Office, Office Action corresponding to foreign counterpart Japanese Patent Application No. 2013-265478, dated Jan. 13, 2015, 3pgs.

Bensmann, et al., "Nickel-titanium Osteosynthesis Clips," Reprint from Medical Focus, 1983.

Besselink, Sachdeva, "Applications of Shape Memory Effects," Memory Metal Holland, Memory Medical Systems, Publication Date Unknown.

Dai, K.R., et al., "Treatment of Intra-Articular Fractures with Shape Memory Compression Staples," Injury, (1993) 24, (IO), 651-655.

(56) References Cited

OTHER PUBLICATIONS

Haasters, Dr. J., et al., "The Use of Ni—Ti as an Implant Material in Orthopedics", pp. 426-444.
Kuo, M.D., et al., "The Use of Nickel-Titanium Alloy in Orthopedic Surgery in China," Orthopedics, Jan. 1989, vol. 12/No. 1.
Lu, M.D., Shibi, "Medical Applications of Ni—Ti Alloys in China," pp. 445-451.
Ricart, "The Use of a Memory Shape Staple in Cervical Anterior Fusion," Proceedings of the Second International Conference on Shape Memory and Superelastic Technologies, Asilomar Conference Center, Pacific Grove, CA, USA, Mar. 2-6, 1997.
Ricart, "The Use of a Memory-Shaple Staple in Cervical Anterior Fusion," in Shape Memory Implants, Springer-Verlag Berlin Heidelberg, 2000.
Tang, Dai, Chen, "Application of a Ni—Ti Staple in the Metatarsal Osteotomy," Bio-Medical Materials and Engineering 6, (1996), 307-312, IOS Press.

* cited by examiner

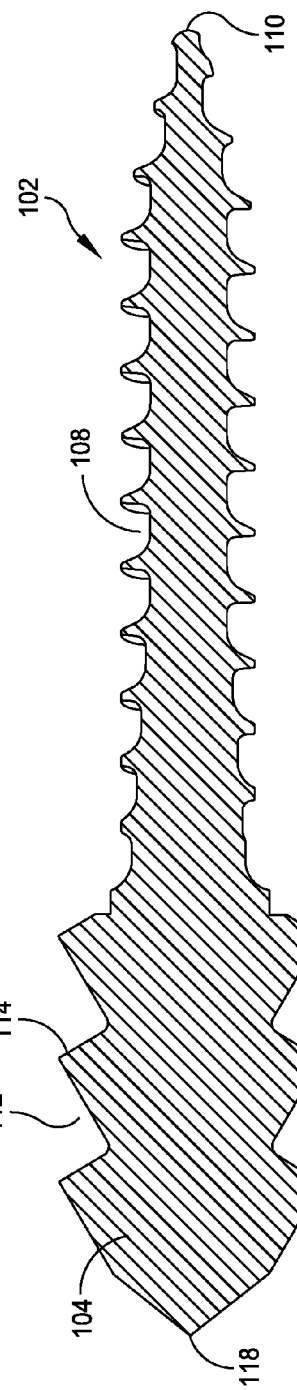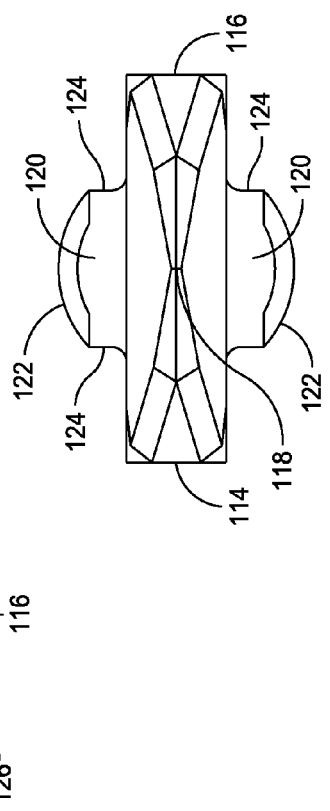
FIG. 2
FIG. 3
FIG. 4

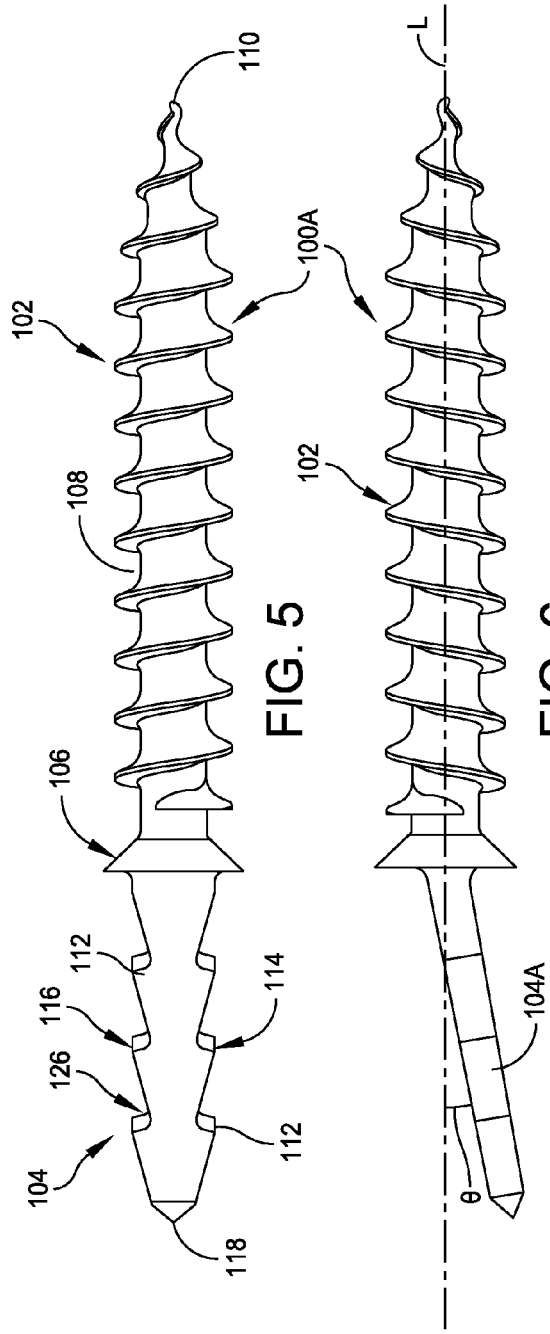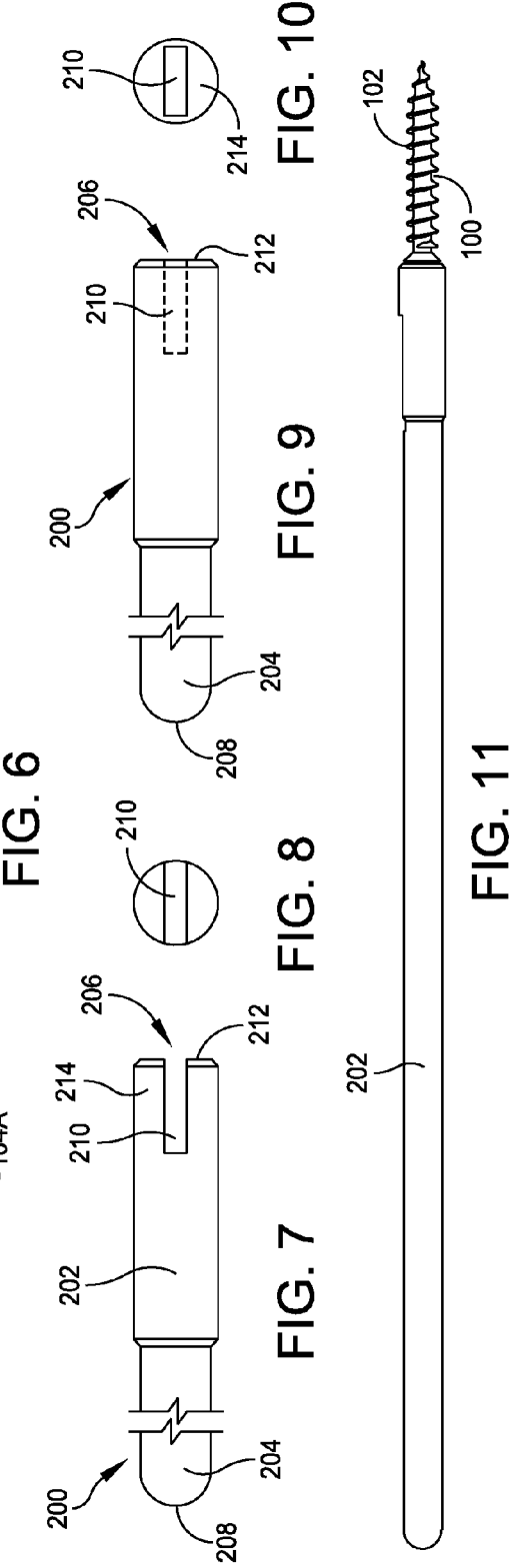

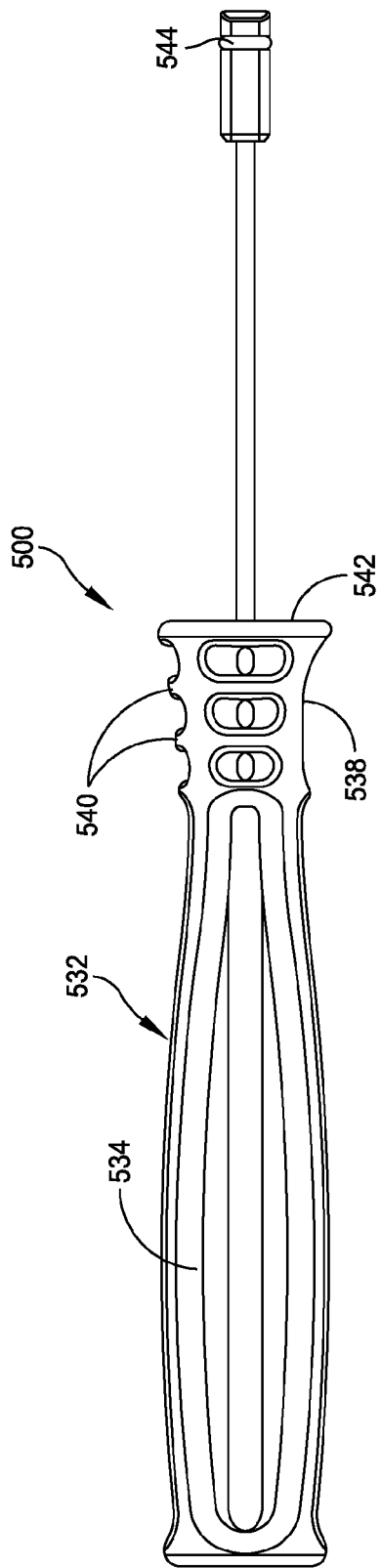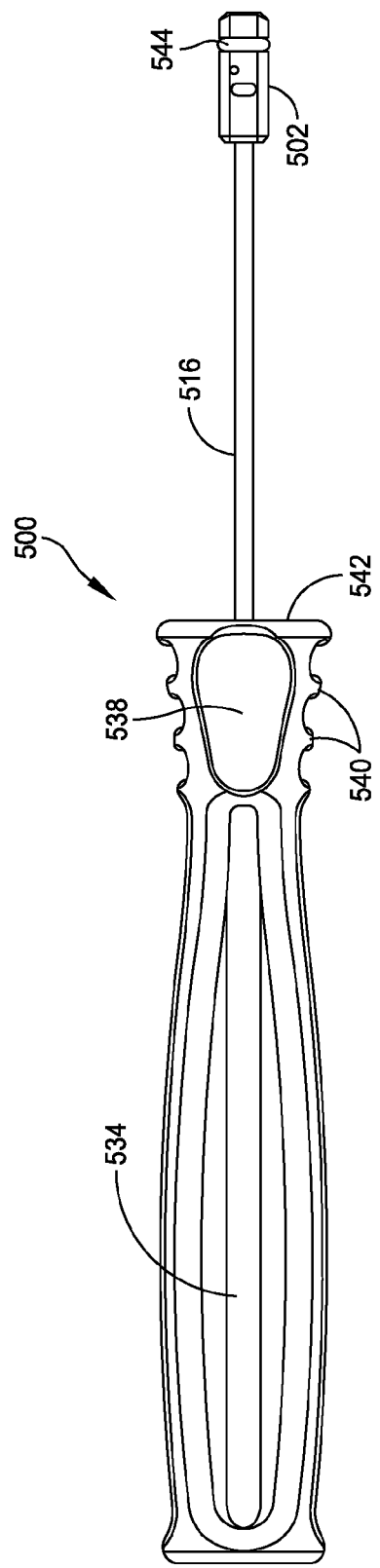

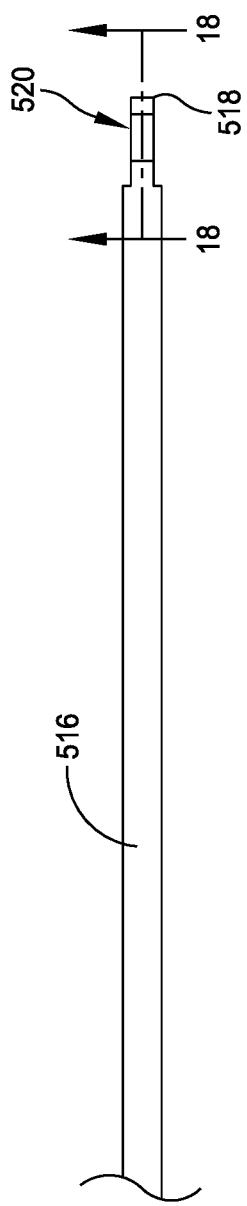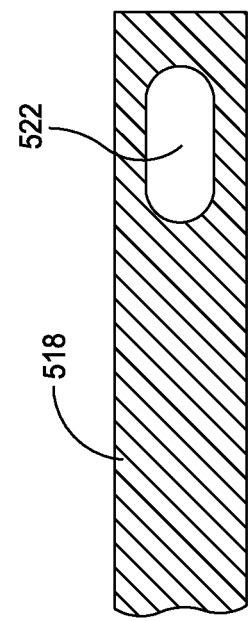
FIG. 17
FIG. 18

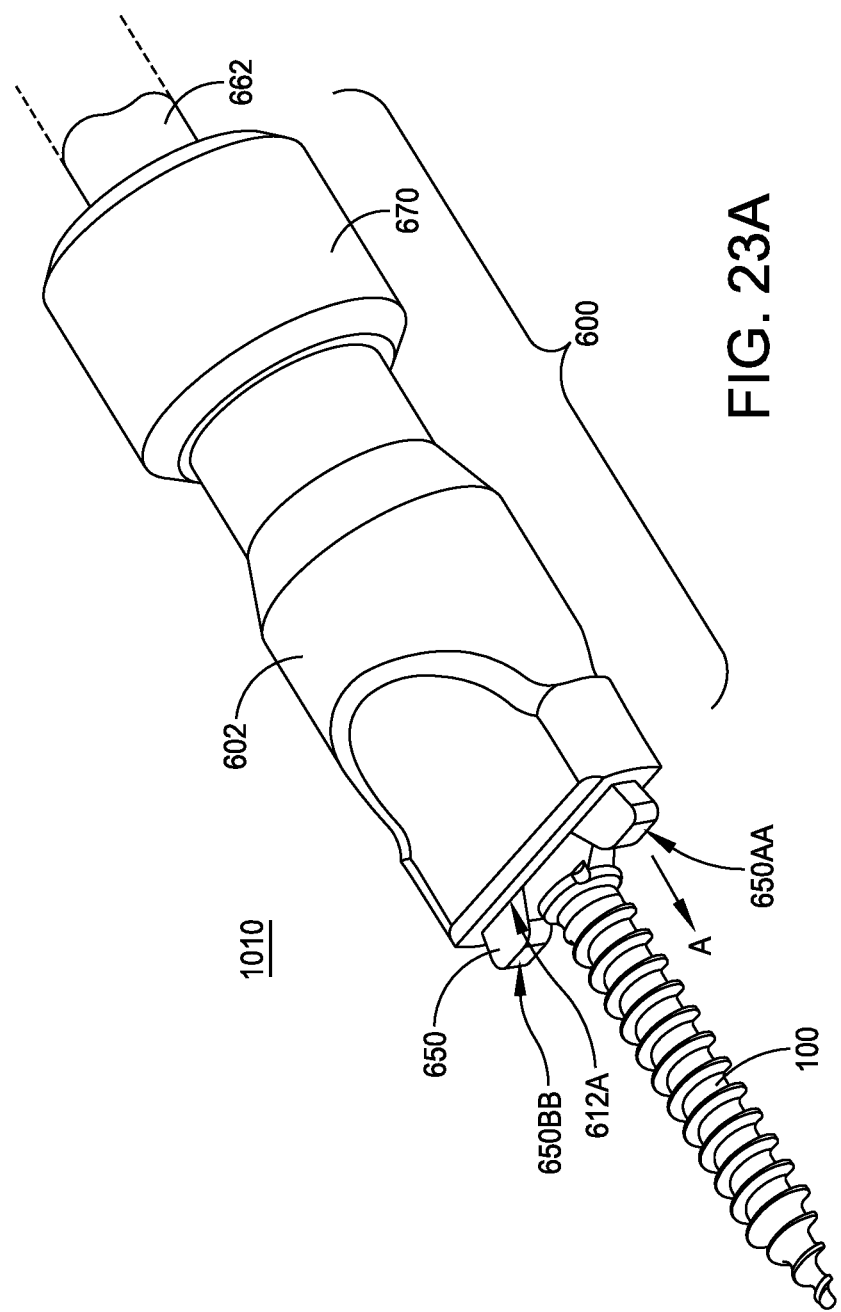

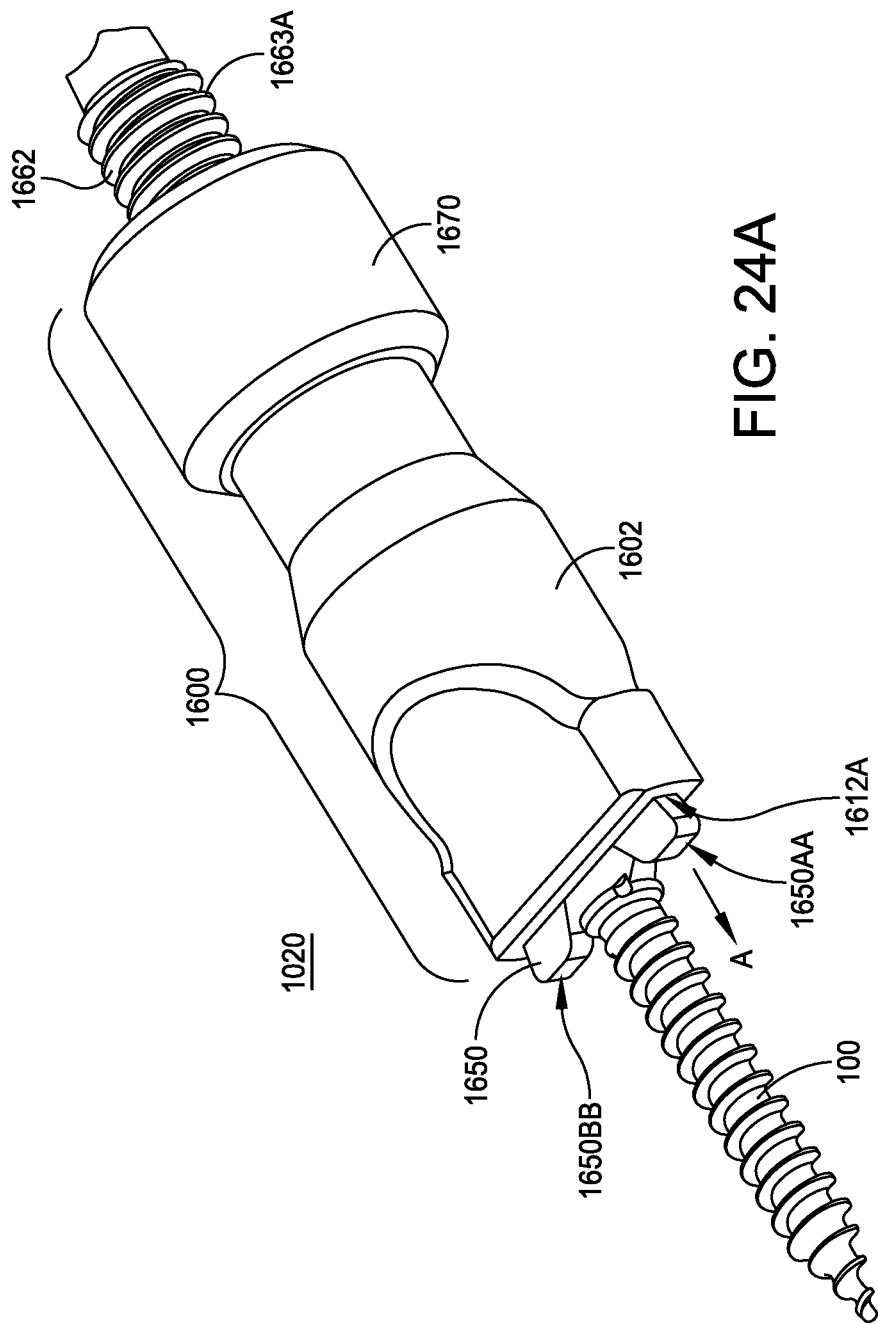

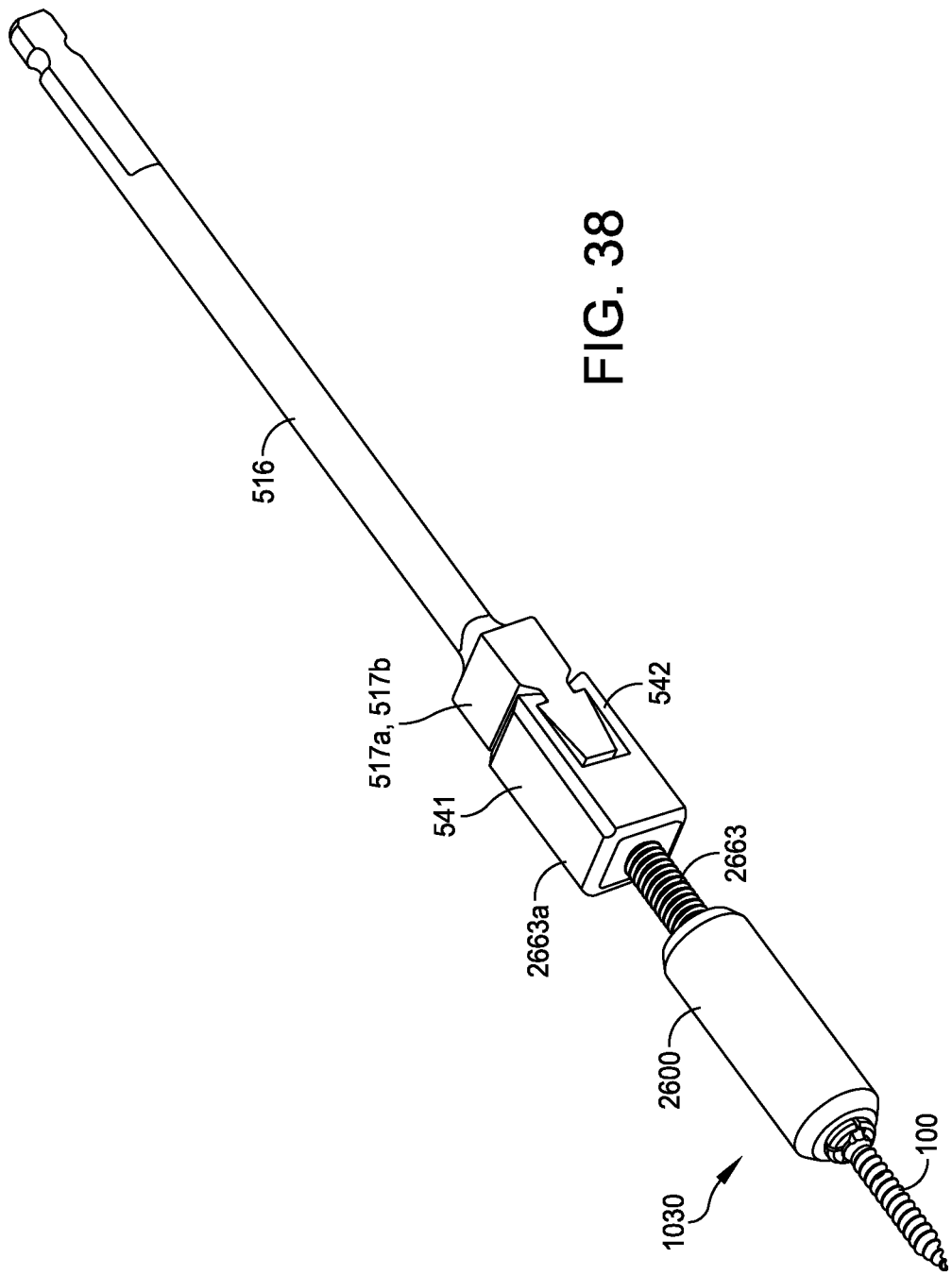

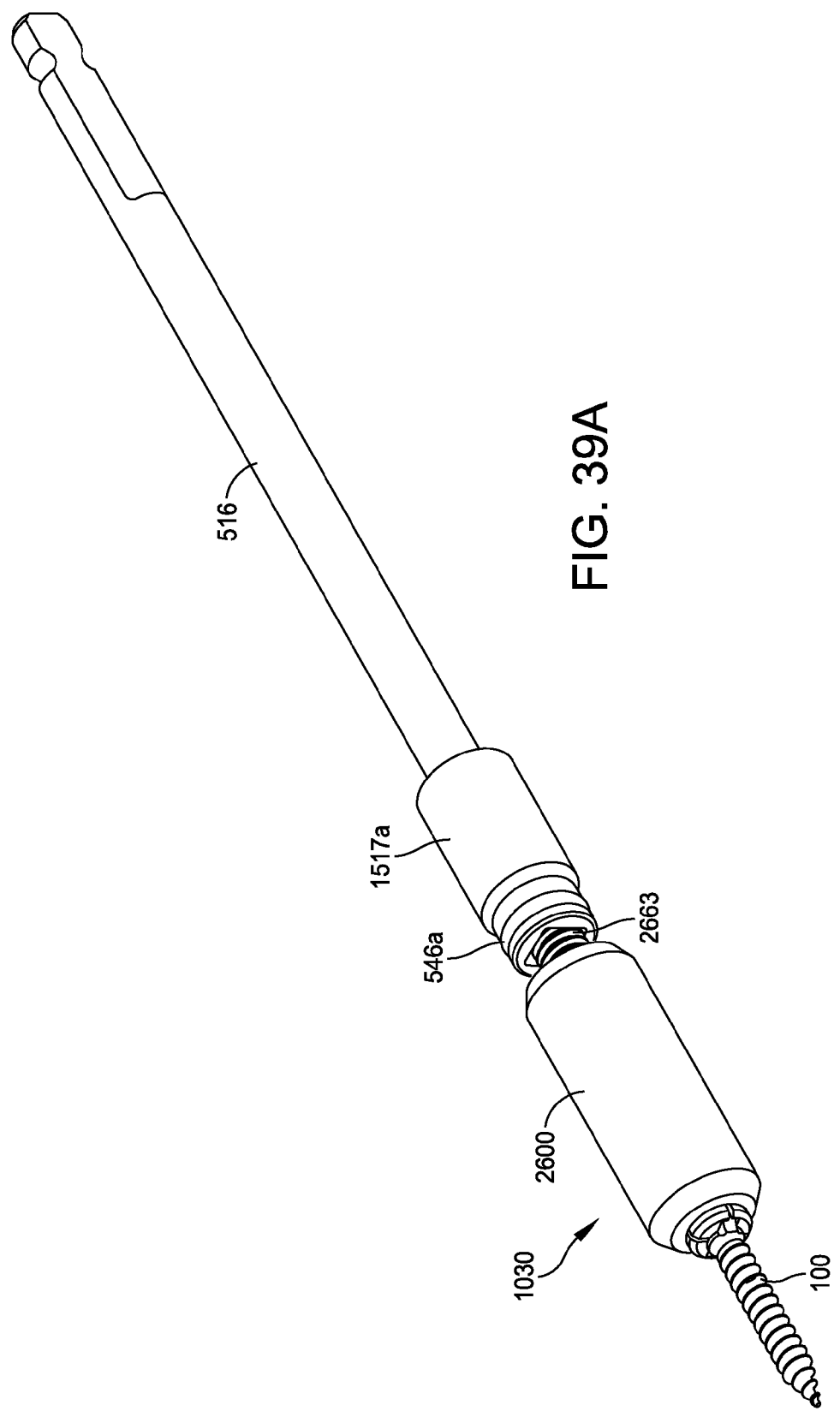

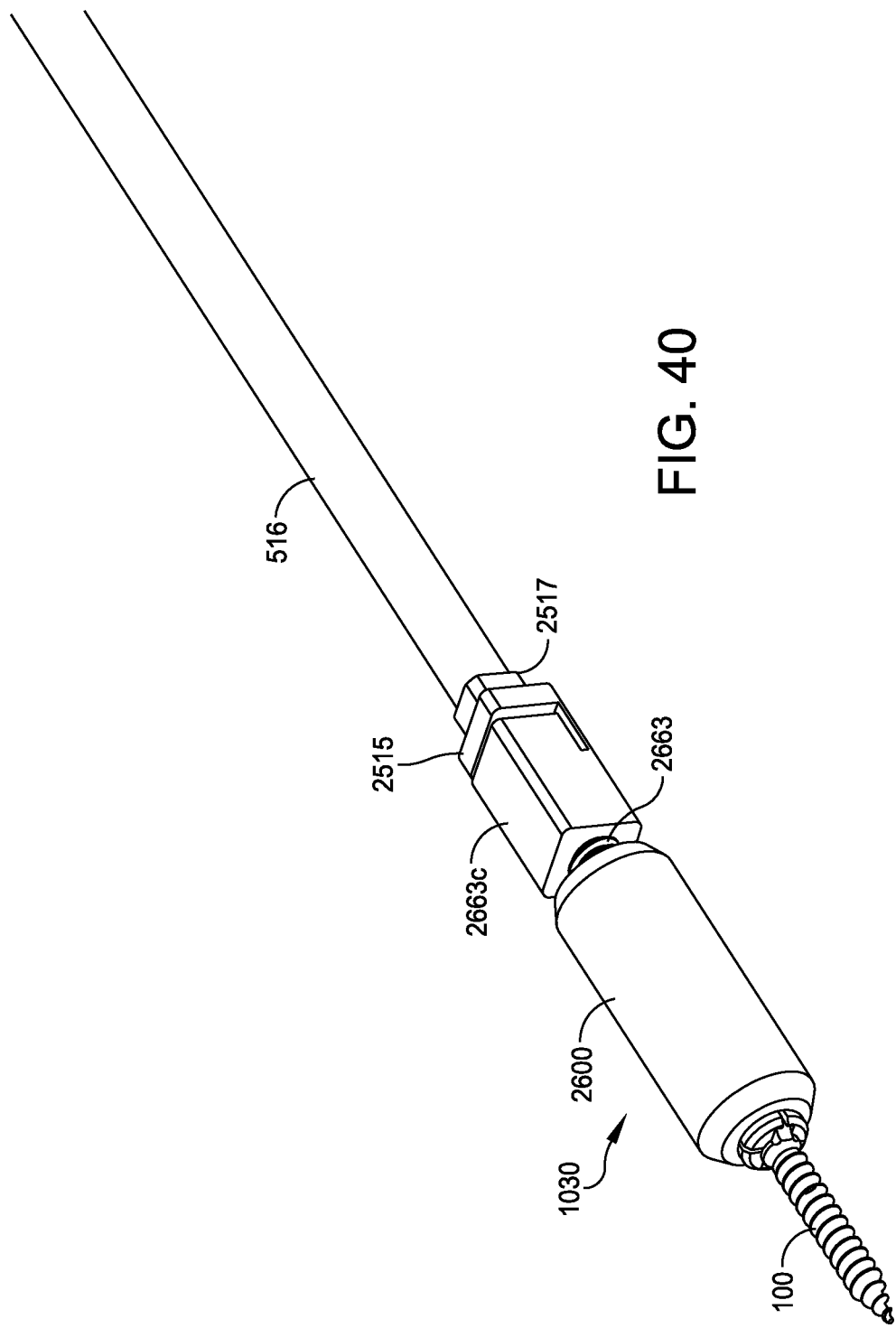

ORTHOPEDIC IMPLANT KIT

CROSS-REFERENCE TO RELATED APPLICATIONS

This application is a division of U.S. patent application Ser. No. 13/804,228, filed Mar. 14, 2013, which is a continuation-in-part of U.S. patent application Ser. No. 13/086,136, filed Apr. 13, 2011, which claims priority to U.S. Provisional Application Ser. No. 61/350,665, which was filed on Jun. 2, 2010, the entire disclosures of which are herein incorporated by reference.

FIELD OF DISCLOSURE

The disclosed system and method relate implants. More specifically, the disclosed system and method relate to installing an implant for treating hammer toe.

BACKGROUND

Hammer toe is a deformity of the toe that affects the alignment of the bones adjacent to the proximal interphalangeal (PIP) joint. Hammer toe can cause pain and can lead to difficulty in walking or wearing shoes. A hammer toe can often result in an open sore or wound on the foot. In some instances, surgery may be required to correct the deformity by fusing one or both of the PIP and distal interphalangeal (DIP) joints.

The most common corrective surgery includes the placement of a pin or rod in the distal, middle, and proximal phalanxes of the foot to fuse the PIP and DIP joints. The pin or rod is cut at the tip of the toe, externally of the body. A plastic or polymeric ball is placed over the exposed end of the rod, which remains in the foot of the patient until the PIP and/or DIP joints are fused in approximately 6 to 12 weeks. This conventional treatment has several drawbacks such as preventing the patient from wearing closed toe shoes while the rod or pin is in place, and the plastic or polymeric ball may snag a bed sheet or other object due to it extending from the tip of the toe resulting in substantial pain for the patient.

Another conventional implant includes a pair of threaded members that are disposed within adjacent bones of a patient's foot. The implants are then coupled to one another through male-female connection mechanism, which is difficult to install in situ and has a tendency to separate.

Yet another conventional implant has a body including an oval head and a pair of feet, which are initially compressed. The implant is formed from nitinol and is refrigerated until it is ready to be installed. The head and feet of the implant expand due to the rising temperature of the implant to provide an outward force on the surrounding bone when installed. However, the temperature sensitive material may result in the implant deploying or expanding prior to being installed, which requires a new implant to be used.

SUMMARY

An implant kit according to an embodiment comprises an adapter and an implant preloaded in the adapter. The adapter has a first end, a second end, and a longitudinal axis extending from the first and to the second end, wherein the first end is configured for receiving an implant and the second end is configured for coupling to a driver shaft of an implant driving tool. The implant is preloaded into the first end of the adapter and the implant comprises an elongated threaded portion, and a blade portion coaxially extending from the elongated threaded portion, and serrated edges, wherein the blade portion is received in the first end of the adapter and the elongated threaded portion of the implant is coaxially aligned with the longitudinal axis of the adapter.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein:

FIG. 2 is a top side view of the hammer toe implant illustrated in FIG. 1;

FIG. 3 is a sectional view of the hammer toe implant taken along line 3-3 in FIG. 2;

FIG. 4 is an end on view of the hammer toe implant taken along line 4-4 in FIG. 2;

FIG. 5 is a side view of another example of a hammer toe implant;

FIG. 6 is a top side view of the hammer toe implant illustrated in FIG. 5;

FIG. 7 is a side view of one example of a driving adapter for use with the hammer toe implants illustrated in FIGS. 1 and 6;

FIG. 8 is an end view of the driving adapter illustrated in FIG. 7;

FIG. 9 is a side view of another example of a driving adapter for use with the hammer toe implants illustrated in FIGS. 1 and 6;

FIG. 10 is an end view of the driving adapter illustrated in FIG. 9;

FIG. 11 is an assembly view of a hammer toe implant engaged by a driving adapter;

FIG. 12A illustrates another example of a driving assembly for installing an implant;

FIG. 12B illustrates side view of the driving assembly illustrated in FIG. 12A;

FIG. 17 is a plan view of the driver shaft of the driving assembly illustrated in FIG. 12A;

FIG. 18 is a cross-sectional view of the fin of the driver shaft taken along line 25-25 in FIG. 17;

FIGS. 23A-23D are various views of an embodiment of an implant kit comprising an adapter configured for coupling to an hammer toe implant using a spring-biased bifurcated retaining clip;

FIGS. 24A-24D are various views of an embodiment of an implant kit comprising an adapter that is configured for coupling to an hammer toe implant using a thread-biased bifurcated retaining clip;

FIG. 38 shows an embodiment of the implant kit comprising an adapter having an implant receiving end configured according to the adapter of FIG. 25A and having a driver shaft coupling end configured for coupling to the driver shaft by a pair of opposing tabs shown in FIGS. 26A, 26B.

FIGS. 39A-39B are various views of an embodiment of the implant kit comprising an adapter having an implant receiving end configured according to the adapter of FIG. 25A and having a driver shaft coupling end configured for coupling to the driver shaft by an O-ring provided on the driver shaft;

FIG. 40 shows an embodiment of the implant kit comprising an adapter having an implant receiving end configured according to the adapter of FIG. 25A and having a driver shaft coupling end configured for coupling to the driver shaft by an off-set clip shown in FIGS. 28A-28C.

DETAILED DESCRIPTION

Figure 1:
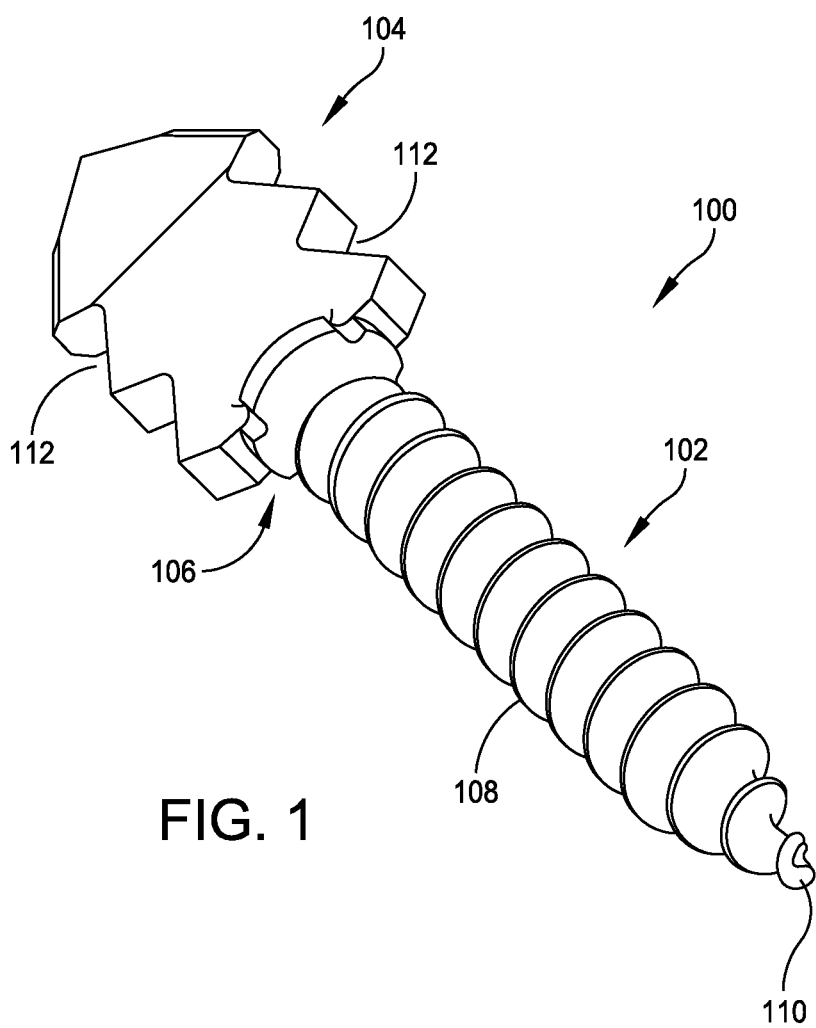
FIG. 1 is an isometric view of one example of an improved hammer toe implant.
Figure 14:
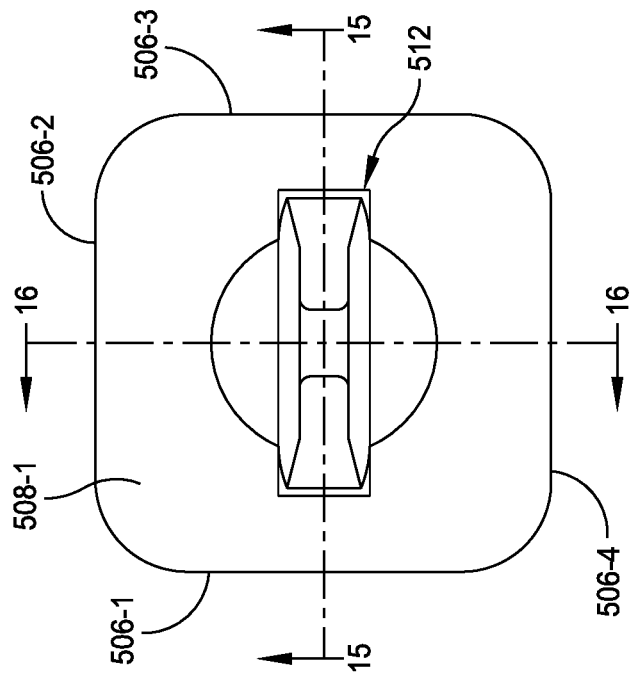
FIG. 14 is an end view of the adapter illustrated in FIG. 13.

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

FIG. 1 illustrates one example of an improved implant 100 for treating hammer toe. As shown in FIG. 1, the hammer toe implant 100 includes an elongate threaded portion 102 and a blade portion 104, which are connected together at an engagement portion 106. Implant 100 may have a substantially linear geometry having an overall length of approximately 19 mm (approximately 0.75 inches). The blade portion 104 extends longitudinally in alignment with the threaded portion 102 as shown in FIGS. 2 and 3.

In some embodiments, such as the implant 100A illustrated in FIGS. 5 and 6, the blade portion 104A may be disposed at angle θ with respect to the longitudinal axis L defined by the threaded portion 102. The angle θ may be between zero and 45 degrees, and more particularly between approximately five and fifteen degrees, although one skilled in the art will understand that the implant 100 may have other dimensions and be provided in different sizes. For example, the implant 100 may be provided in lengths of 16 mm and 22 mm, to name a few potential lengths.

The threaded portion 102 may include a plurality of threads 108 disposed along its entire length, which may be approximately 13 mm (approximately 0.5 inches). The tip 110 of the threaded portion 102 may be pointed to facilitate the advancement of the threads 108 into bone. The threads 108 may have a maximum outer diameter of approximately 2 mm (approximately 0.08 inches), although one skilled in the art will understand that the threaded portion 102 may have other dimensions and be configured to be threaded into a phalanx bone of a person. For example, threads may have an outer diameter of approximately 2.4 mm and 1.6 mm, to name a few potential possibilities.

The blade portion 104 includes a plurality of teeth 112 along its serrated edges 114, 116. The blade portion 104 may have a width that is greater than its thickness as best seen in FIGS. 2 and 4. For example, the blade portion 104 may have a width of approximately 0.4 centimeters (approximately 0.16 inches) and a thickness of approximately 0.1 centimeters (approximately 0.04 inches) each of which taper to a point 118. The blade portion 104 may have a substantially rectangular cross-sectional area as illustrated in FIG. 4, although one skilled in the art will understand that the blade portion 104 may have other cross-sectional geometries.

The engagement portion 106 may include a pair of protrusions 120 extending from opposite sides of the implant 100 and having rounded outer edges 122. The sides 124 of the protrusions 120 may be substantially parallel with each other as shown in FIG. 4.

The implant 100 can be installed using a driving adapter 200 such as the one illustrated in FIGS. 7-10. The driving adapter 200 has an elongate adapter body 202 having a proximal end 204 and a distal end 206. The adapter body 202 of the driving adapter 200 may have a circular cross-sectional geometry, although one skilled in the art would understand that the adapter body 202 may have other cross-sectional geometries including, but not limited to, a triangular, a rectangular, a pentagonal, and a hexagonal cross-sectional geometries to name a few.

The proximal end 204 may be substantially solid and have a rounded tip 208. The distal end 206 may define a slot 210 sized and configured to receive the blade portion 104 of the implant 100 therein. The slot 210 may have a rectangular cross-sectional geometry and have a depth that is sufficient to receive the entire blade portion 104 of the implant 100 such that distal edges 212 of slot 210 contact protrusions 120 of engagement portion 106. However, one skilled in the art will understand that slot 210 may have other cross-sectional geometries and dimensions. Slot 210 may extend through side walls 214 of the adapter body 202 as shown in FIGS. 7 and 8, or side walls 214 may completely enclose slot 210 as shown in FIGS. 9 and 10.

If the driving adapter 200 is to be used with an implant having a substantially linear lengthwise geometry such as the implant 100 illustrated in FIGS. 1-5, then the slot 210 may extend in a direction that is substantially parallel to an axis defined by the adapter body 202 of the driving adapter 200. If the driving adapter 200 is to be used with an implant having a blade portion 104A that extends or oriented at an angle θ with respect to the longitudinal axis A of the threaded portion 102 such as in the implant 100A illustrated in FIGS. 5 and 6, then the slot 210 may extend from the distal edges 212 at the corresponding angle θ with respect to an axis defined by the length of the adapter body 202 such that elongate threaded portion 102 of implant 100A is linearly aligned with the adapter body 202 of the driving adapter 200 when the implant 100A is inserted into the driving adapter 200 as shown in FIG. 11. For example, if the extension angle θ of the blade portion 104A of the implant 100A is ten degree with respect to the longitudinal axis defined by the elongate threaded portion 102, then the slot 210 of the driving adapter 200 would be oriented at ten degrees angle with respect to the longitudinal axis defined by the adapter body 202 such that the threaded portion 102 of the implant 100A and the adapter body 202 of the driving adapter 200 are substantially coaxially aligned.

FIGS. 12A-19 illustrate an example of an implant adapter 502 coupled to a driver shaft 516 of a driver tool 500 for installing a hammer toe implant into bone. As shown in FIGS. 12A and 12B, the driver tool 500 includes a handle 534 that is over-molded or otherwise coupled to the driver shaft 516. The implant adapter 502 includes an adapter body 504 with a substantially rectangular side profile comprising side walls 506-1, 506-2, 506-3, and 506-4 (collectively referred to as "side walls 506") and a pair of end walls 508-1, 508-2 (collectively referred to as "end walls 508") having a substantially square geometry as best seen in FIGS. 13-16.

Figure 13:
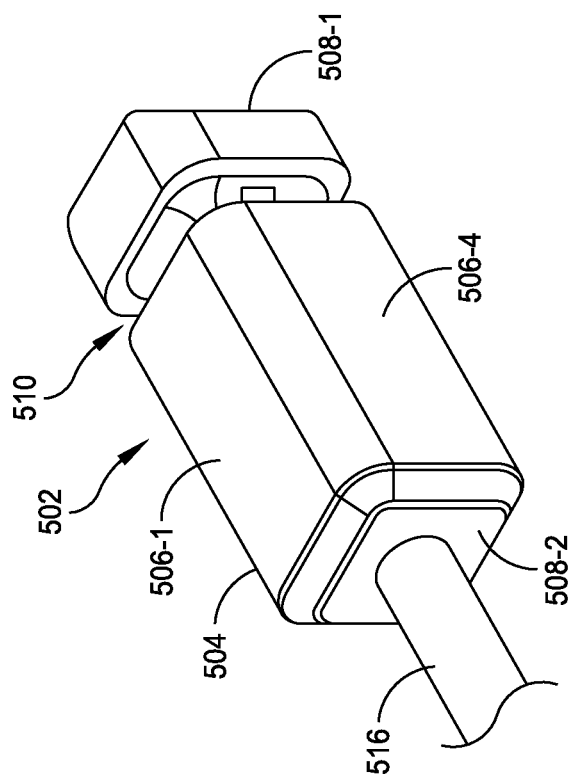
FIG. 13 is an isometric view of an adapter of the driving assembly illustrated in FIG. 12A.

As shown in FIG. 13, the adapter body 504 is provided with a recess or a groove 510 extending circumferentially along the side walls 506 on the adapter. The groove 510 is dimensioned such that an elastic O-ring 544 (see FIGS. 17, 18 and 22) can be received therein. Additionally, the groove 510 is located along the side walls 506 at a distance from the end walls 508 that aligns the groove 510 with a valley portion 126 between the teeth-like serrations 112 on the blade portion 104.

Figure 16:
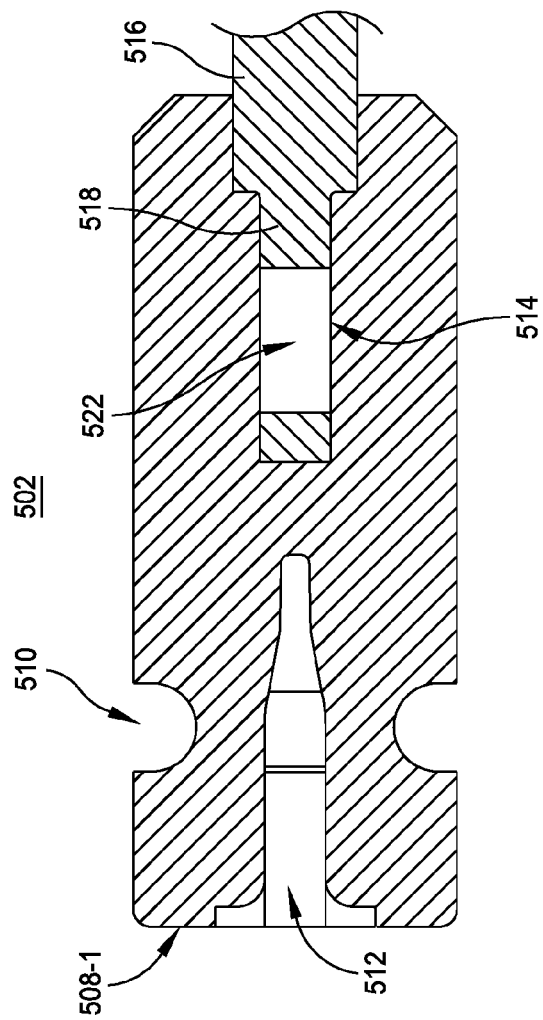
FIG. 16 is a cross-sectional view of the adapter taken along line 22-22 in FIG. 14.
Figure 15:
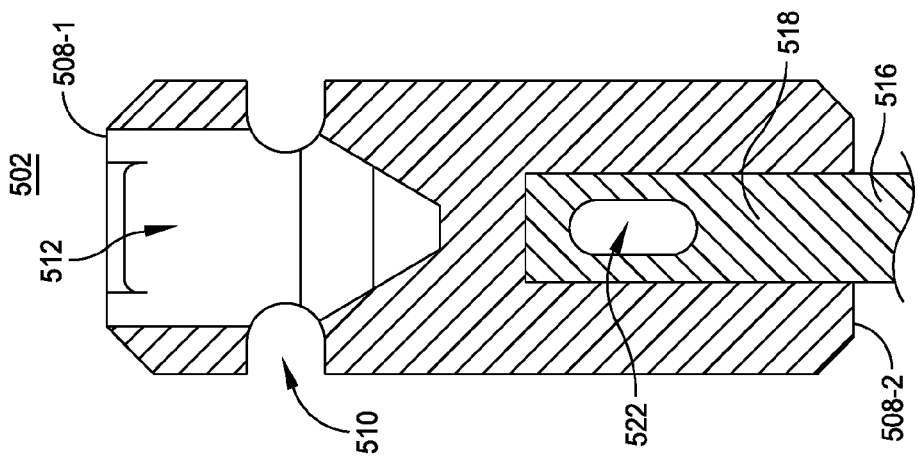
FIG. 15 is a cross-sectional view of the adapter taken along line 21-21 in FIG. 14.
Figure 19:
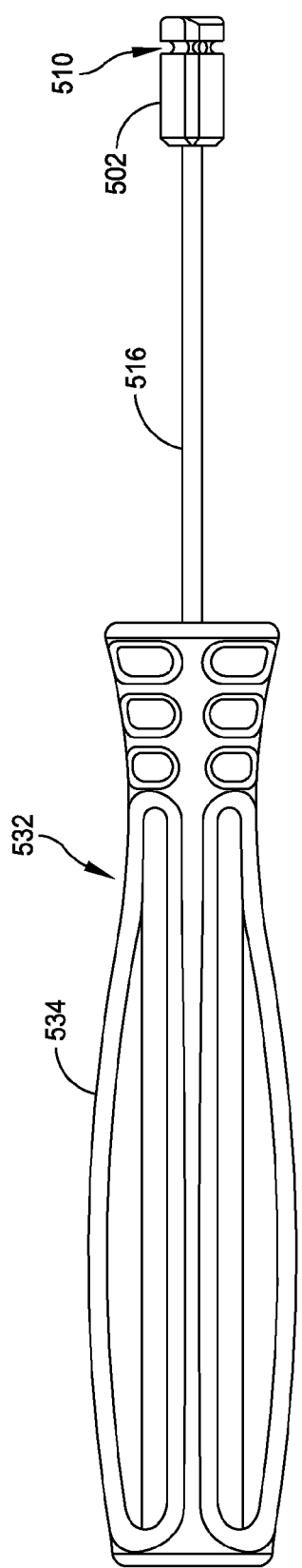
FIG. 19 is a plan view of driving assembly illustrated in FIG. 12A without the o-ring.

The end wall 508-1 defines a slot 512 having a geometry that complements the cross-sectional geometry of the blade portion 104, 104A of the implant 100, 100A. For example, for the implant 100 having a straight blade portion 104 as illustrated in FIG. 2, the aperture 512 may extend approximately parallel to the lengthwise direction of side walls 506. For the blade portion 104A of implant 100A that is angled as illustrated in FIG. 6, the aperture 512 may extend from wall 508-1 at the angle θ relative to the longitudinal axis of the implant adapter 502 or the plane defined by one of the side walls 506-2 or 506-4 as will be understood by one skilled in the art. In some embodiments, the aperture 512 has a depth that is greater than or equal to a length of the blade portion 104, 104A such that the blade portion 104, 104A may be received within the adapter body 504 and the engagement portion 106 abuts the end wall 508-1. Similarly, the end wall 508-2 defines a bore 514 that is sized and configured to receive an adapter-engaging end, of the elongate driver shaft 516 therein. FIG. 16 shows the bore 514 provided in the driver shaft receiving end of the implant adapter 502.

As best seen in FIGS. 15-19, the driver shaft 516 includes a fin 518 disposed at a first end 520. The fin 518 disposed at end 520 of the driver shaft 516 has a rectangular shape and is sized and configured to be received within the bore 514 of adapter 502. The fin 518 defines a slot 522, which is sized and configured to receive a pin (not shown) for cross-pinning driver shaft 516 to adapter 502. In some embodiments, the end 520 may have other cross-sectional geometries including, but not limited to, triangular, square, and pentagonal, to name a few possibilities, that are configured to be received within the bore 514. The adapter 502 can be configured in a variety of different manner to be removably coupled to the driver shaft 516 as described below.

According to an aspect of the present disclosure, the implant can be preloaded into an adapter and provided as an implant kit. Various embodiments of such an implant kit will be described below.

Figure 20A:
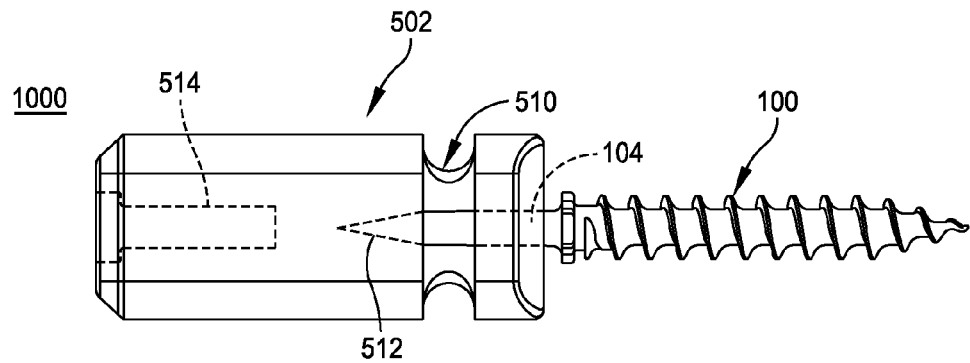
FIGS. 20A, 20B and 21 illustrate an implant kit comprising a hammer toe implant preloaded in the adapter shown in FIGS. 13-16.

FIG. 20A shows an implant kit 1000 in which the blade portion 104 of the implant 100 is inserted into the aperture 512 of the adapter 502. When the implant 100 is received in the adapter 502, the elongated threaded portion 102 of the implant 100 extends coaxially in alignment with the longitudinal axis of the adapter.

Figure 20B:
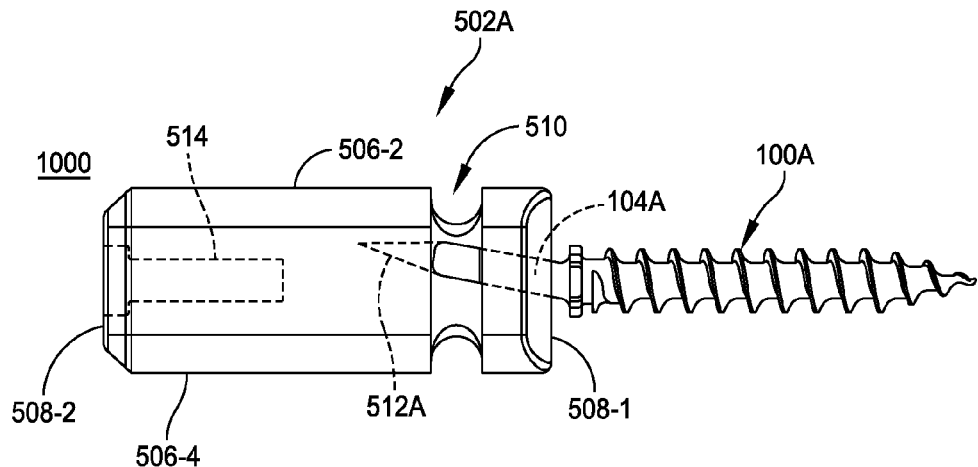

FIG. 20B shows an implant kit 1000 in which the angled blade portion 104A of the implant 100A inserted into the aperture 512A of the adapter 502A. In this embodiment, the aperture 512A is angled correspondingly to receive the angled blade portion 104A of the implant 100A such that when the implant 100A is received in the adapter 502A, elongated threaded portion 102 of the implant 100A extends coaxially in alignment with the longitudinal axis of the adapter.

Figure 21:
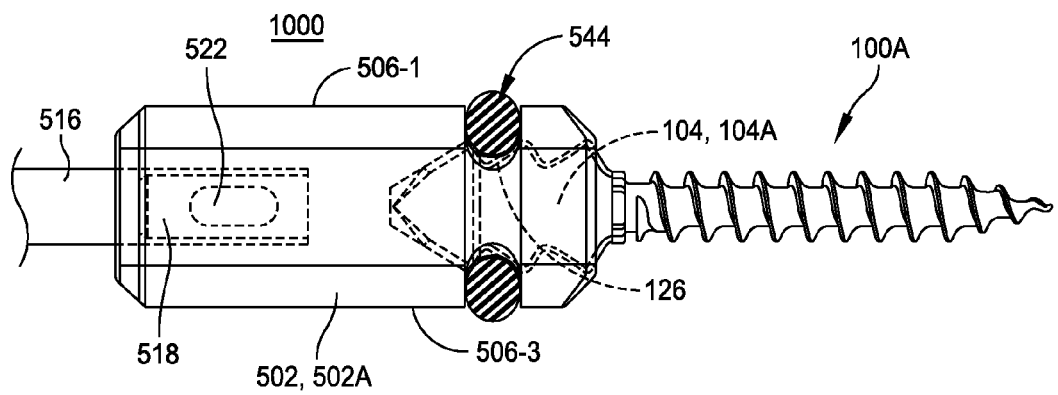

FIG. 21 is a view of the implant kit 1000 in which the implant 100, 100A is preloaded into the adapter 502. FIG. 21 is viewed from within the plane of FIGS. 20A and 20B so that the view shows the full width of the blade portion 104, 104A. In this view of FIG. 21, with the blade portion 104, 104A fully inserted into the adapter 502, 502A, an elastic O-ring 544 (also shown in FIGS. 12A, 12B and 22) placed in the groove 510 retains the implant 100, 100A in the adapter 502, 502A by preventing the implant from sliding out of the adapter. The cross-sections of the O-ring is shown in FIG. 21. The groove 510 is cut into the adapter with a sufficient depth so that when the O-ring 544 is placed therein the O-ring is positioned within the valley 126 between two adjacent teeth 112 on either side of the blade portion 104, 104A, as shown in FIG. 21. Because the O-ring 544 is elastic, one can push the blade portion 104, 104A of the implant into the adapter with sufficient force for one or more of the teeth 112 to push past the O-ring 544 when assembling the implant kit 1000. Once the implant kit 1000 is assembled, however, the O-ring 544 secures and retains the implant 100, 100A in the adapter 502 until one intentionally pulls off the adapter 502 after the implant is driven into a bone.

Figure 22:
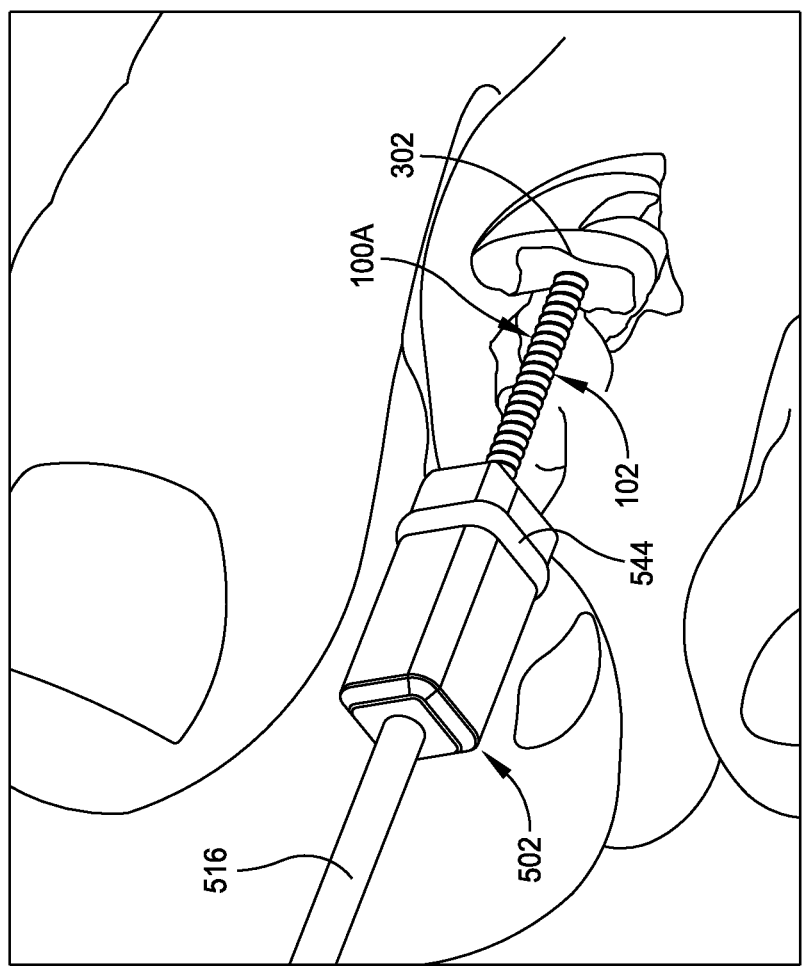
FIG. 22 illustrates a hammer toe implant being driven into a proximal phalanx.

In use, the surgeon would attach the implant kit 1000 to the driver tool 500 to manually drive the threaded portion 102 of the implant 100, 100A into the resected surface of proximal phalanx 302 as illustrated in FIG. 22. The implant 100, 100A is driven into the proximal phalanx 302 until engagement portion 106 abuts the proximal phalanx 302. The implant 100, 100A is then decoupled from the adapter 502 by axially pulling the adapter 502 away from the implant 100, 100A with sufficient force to push the O-ring 544 outward and separate the adapter 502 from the implant 100, 100A.

Figure 23B:
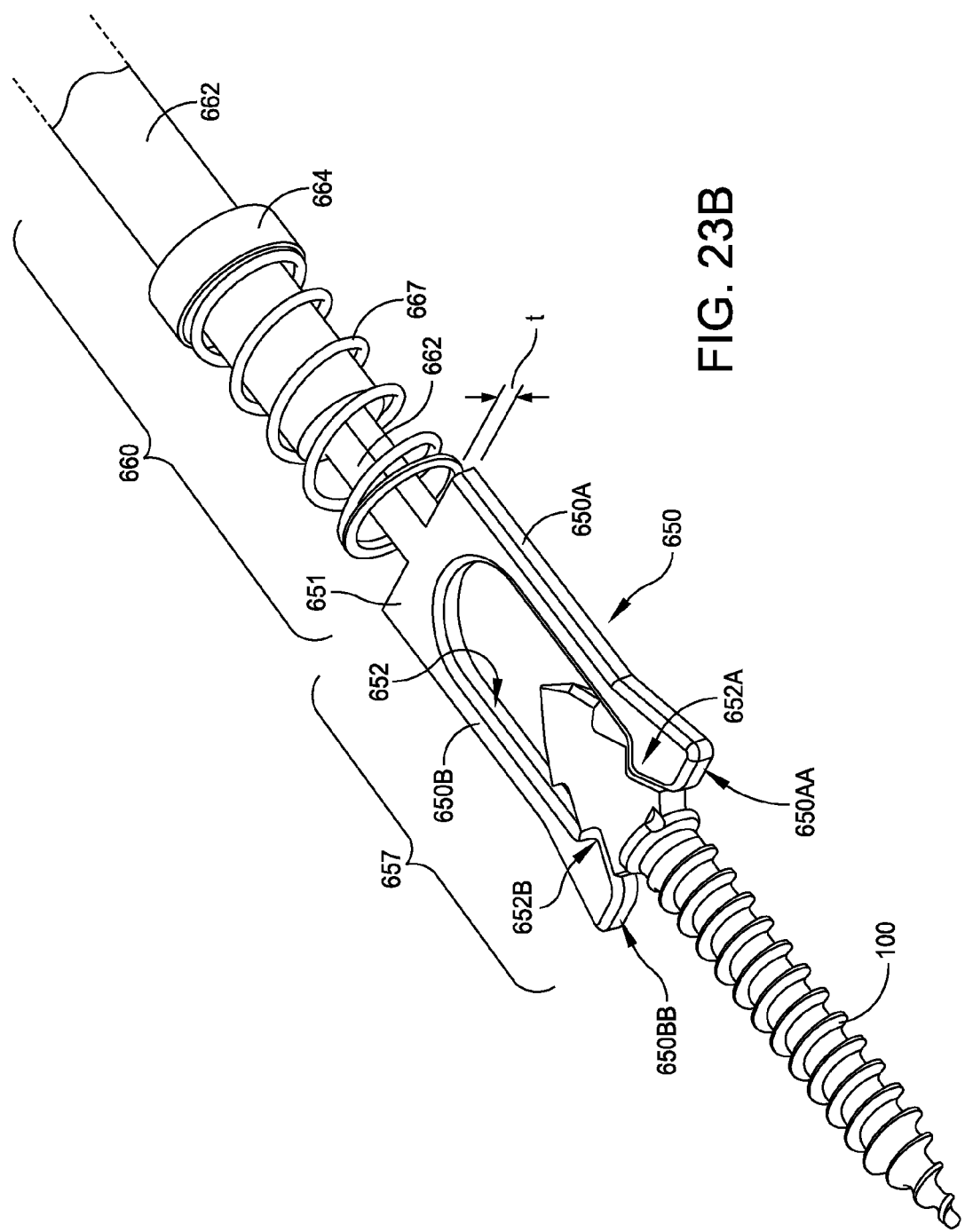
Figure 23C:
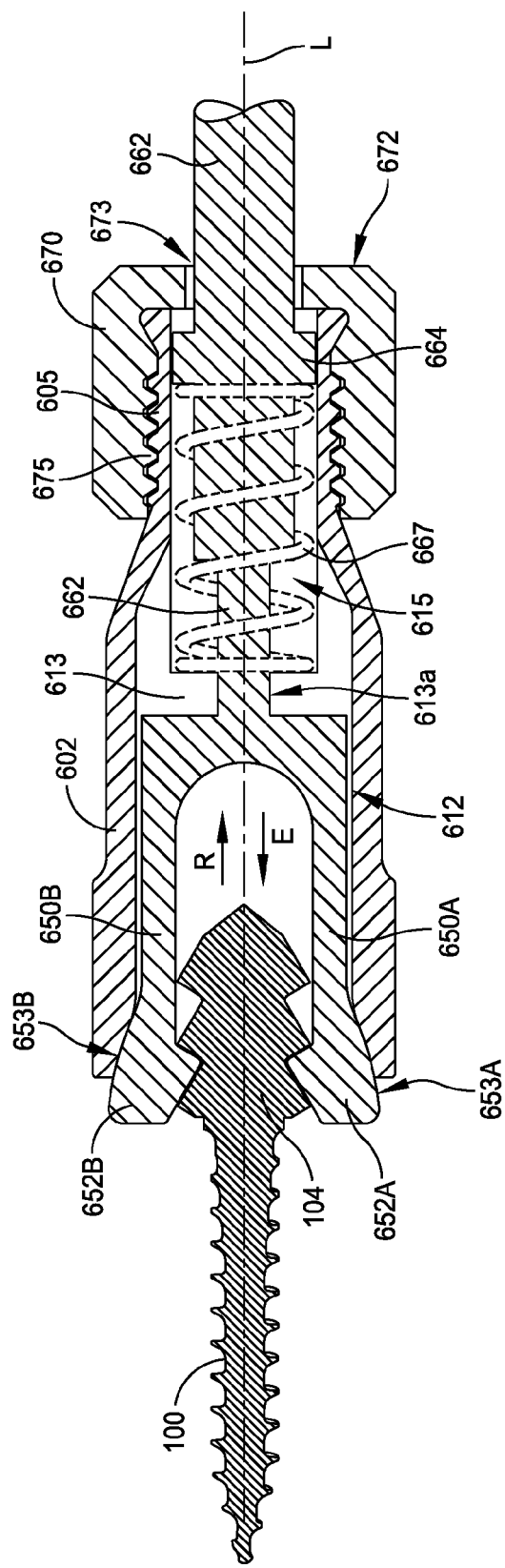

FIGS. 23A-23C show various views of an implant kit 1010 according to another embodiment. The implant kit 1010 comprises an adapter 600 that is configured at a first end for receiving a hammer toe implant 100 and removably retaining the implant therein using a spring-biased bifurcated retaining clip 650. The adapter 600 has an adapter body 602 substantially forming the first end configured for receiving the implant 100. The bifurcated retaining clip 650 is provided within a slot 612 extending into the adapter body 602 from the slot opening 612A. The bifurcated retaining clip 650 is spring-biased to be normally in a fully retracted position shown in FIG. 23A. In the fully retracted position, the bifurcated retaining clip 650 retains the implant 100 by capturing the blade portion 104 between the bifurcated arms. In FIG. 23A, leading ends 650AA, 650BB of the bifurcated retaining clip 650 are shown protruding through the slot opening 612A. The implant 100 is released from the implant kit 1010 by extending the bifurcated retaining clip 650 out in the direction of the arrow A shown in FIG. 23A.

FIG. 23B shows a detailed view of the structure of the bifurcated retaining clip 650. The bifurcated retaining clip 650 comprises an implant-engaging portion 657 and a base portion 660. The implant engaging portion 657 is provided with bifurcated arms 650A and 650B that are configured for holding the blade portion 104 of the implant 100 between the bifurcated arms 650A and 650B at their leading ends 650AA and 650BB.

The bifurcated arms 650A, 650B are dimensioned to have substantially the same thickness t as the blade portion 104 of the implant 100. That allows the bifurcated arms 650A, 650B to fit within the slot 612 of the adapter 602 with the blade portion 104 of the implant 100 held between the bifurcated arms 650A, 650B. The interior surface 652 of the bifurcated arms 650A, 650B at their leading ends 650AA and 650BB can be contoured with protrusions 652A and 652B that are configured for engaging the blade portion 104. In one preferred embodiment, the protrusions 652A, 652B have contours that match the contours of the valley 126 between two teeth 112 of the blade portion 104.

As shown in FIGS. 23B and 23C, the bifurcated arms 650A and 650B are joined at the base end 651. The base portion 660 comprises a stem portion 662 that extends from the base end 651 generally along the longitudinal axis L. The stem portion 662 is configured with a spring-retainer portion 664. As will be discussed further below, the stem portion 662 can be configured to couple to the driver shaft of the driver tool in one of a variety of ways.

FIG. 23C shows a longitudinal cross-sectional view of the implant kit 1010 taken through a plane that is parallel to the blade portion 104. The bifurcated retaining clip 650 is shown in its normal retracted position within the slot 612 of the adapter body 602 with the blade portion 104 of the implant 100 captured and retained in between the bifurcated arms.

The respective outer sides 653A, 653B of the two bifurcated arms 652A, 652B are slanted at an angle flaring out away from the longitudinal axis L of the implant kit so that the overall width of the bifurcated retaining clip 650 between the outer sides 653A, 653B increase towards the leading ends 650AA, 650BB of the bifurcated arms. The slanted outer sides 653A, 653B enable the bifurcated arms 652A, 652B to close on the blade portion 104 as a compressible coil spring 667 retracts the bifurcated retaining clip 650 into the slot 612. As the bifurcated arms are retracted, the outer sides 653A, 653B contact the surfaces of the slot 612 and as the bifurcated arms continue to retract inward, the slanted outer sides 653A, 653B cause the bifurcated arms to be squeezed and close in and grip the blade portion. Thus the implant 100 is retained in the adapter 600 and cannot be decoupled from the adapter until the bifurcated retaining clip 650 is extended out.

At the end opposite from the slot opening 612A, the adapter body 602 is configured with a cylindrical cavity 615.

The base portion 660 of the bifurcated retaining clip is accommodated in the cylindrical cavity 615. Between the cylindrical cavity 615 and the slot 612 is provided an end wall 613. The end wall has a hole 613a through which the stem portion 662 extends.

Figure 23D:
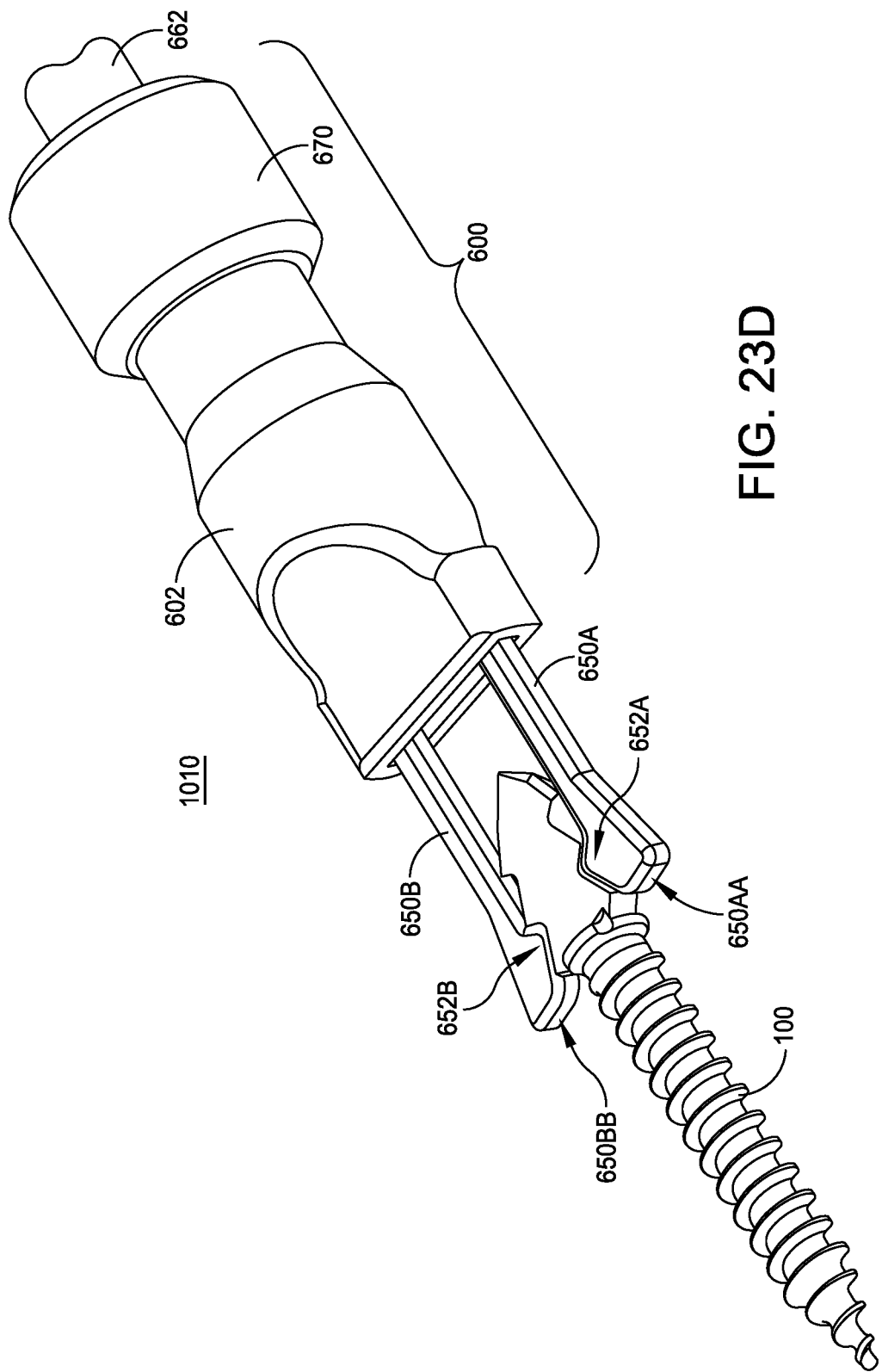

The compressible coil spring 667 is captured between the end wall 613 and the spring-retainer portion 664. The coil spring 667 is normally at its fully expanded configuration and applies bias against the end wall 613 and the spring-retainer portion 664. This spring bias pushes against the spring-retainer portion 664 in the direction of the arrow R with respect to the end wall 613 of the adapter body 602. Because the end wall 613 acts as a stop for the bifurcated arms 652A, 653B, the bias of the coil spring 667 keeps the bifurcated retaining clip 650 in its fully retracted position shown in FIG. 23C. By pushing the base portion 660 in the direction represented by the arrow E towards the slot opening 612A, the coil spring 667 is compressed and the bifurcated arms 650A and 650B will extend out of the slot 612 thus releasing its grip on the implant 100 so that the adapter 650 can be decoupled from the implant 100. FIG. 23D shows the implant kit 1010 in the configuration where the bifurcated retaining clip 650 is in the extended position.

The end of the adapter body 602 with the cylindrical cavity 615 is provided with a retaining nut 670 for retaining the base portion 660 of the bifurcated retaining clip 650 inside the adapter body 602. The retaining nut 670 and the adapter body 602 can be configured to threadably engage each other as shown in FIG. 23C. Screw threads 605 on the adapter body and screw threads 675 on the retaining nut 670 enable this. The retaining nut 670 is provided with a hole 673 for accommodating the stem portion 662 of the bifurcated retaining clip.

FIGS. 24A-24D show various views of an implant kit 1020 that utilizes a thread-biased bifurcated retaining clip 1650 according to another embodiment. The implant kit 1020 comprises an adapter 1600 that is configured at a first end for receiving a hammer toe implant 100 and removably retaining the implant therein using the thread-biased bifurcated retaining clip 1650. The adapter 1600 has an adapter body 1602 substantially forming the first end configured for receiving the implant 100.

The bifurcated retaining clip 1650 is provided within a slot 1612 extending into the adapter body 1602 from the slot opening 1612A. The bifurcated retaining clip 1650 is thread-biased to be normally in a fully retracted position shown in FIG. 24A. In the fully retracted position, the bifurcated retaining clip 1650 retains the adapter 100 by capturing the blade portion 104 of the adapter between the bifurcated arms 1650A, 1650B. The term "thread-biased" is used herein to refer to the fact that in this embodiment, the bifurcated retaining clip 1650 is kept in its retracted position by the operation of screw threads 1663 provided on a stem portion 1662 of the retaining clip 1650.

In FIG. 24A, leading ends 1650AA, 1650BB of the bifurcated retaining clip 1650 are shown protruding through the slot opening 1612A. The implant 100 is released from the implant kit 1020 by extending the bifurcated retaining clip 1650 out in the direction of the arrow A shown in FIG. 24A.

Figure 24B:
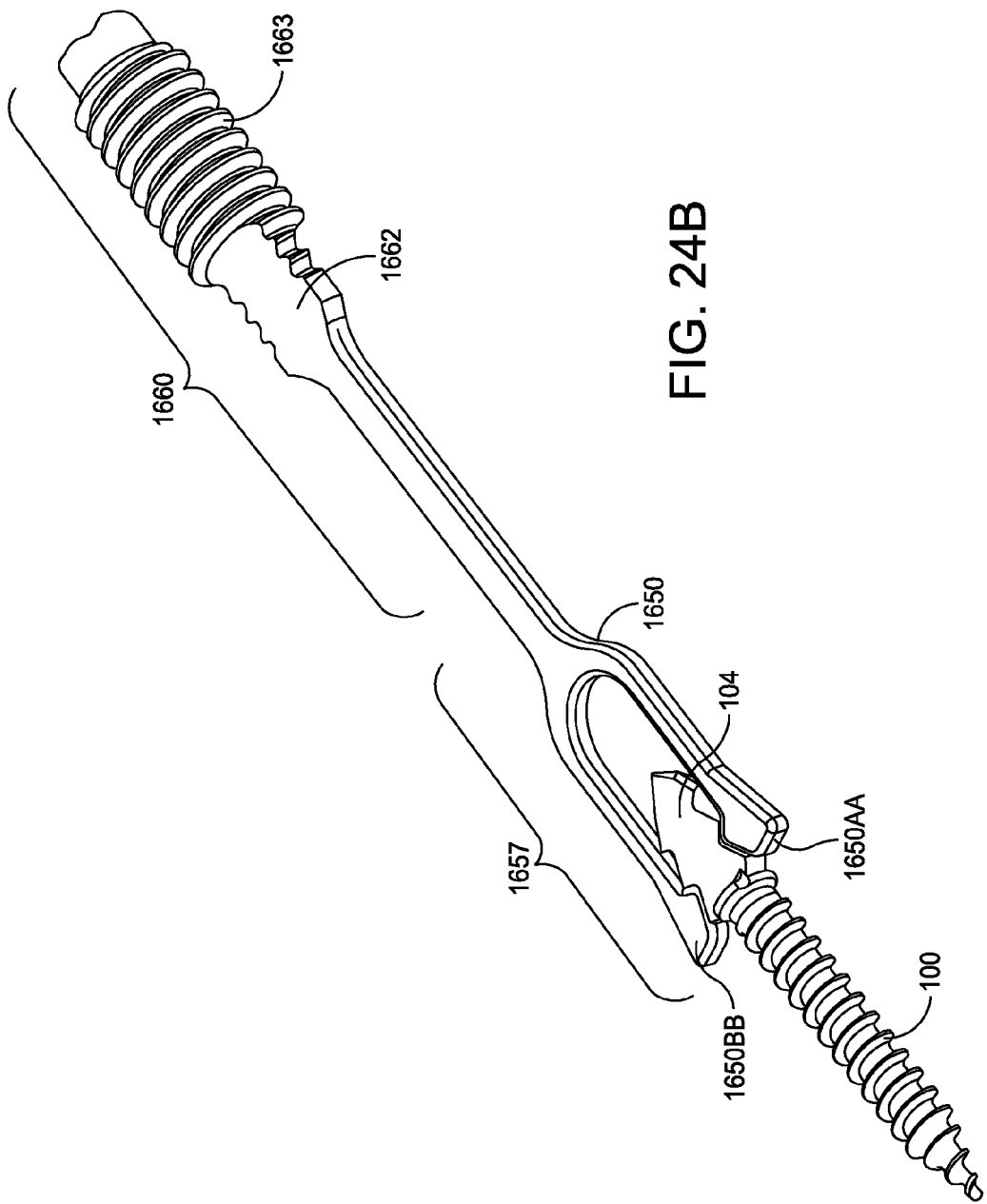

FIG. 24B shows a detailed view of the structure of the bifurcated retaining clip 1650. The bifurcated retaining clip 1650 comprises an implant-engaging portion 1657 and a base portion 1660. The implant engaging portion 1657 is provided with bifurcated arms 1650A and 1650B that are configured for holding the blade portion 104 of the implant 100 between the bifurcated arms 1650A and 1650B at their leading ends 1650AA and 1650BB.

The bifurcated arms 1650A, 1650B are dimensioned to have substantially the same thickness t as the blade portion 104 of the implant 100. That allows the bifurcated arms 1650A, 1650B to fit within the slot 1612 of the adapter 1602 with the blade portion 104 of the implant 100 held between the bifurcated arms 1650A, 1650B. The interior surface 1652 of the bifurcated arms 1650A, 1650B at their leading ends 1650AA and 1650BB can be contoured with protrusions 1652A and 1652B that are configured for engaging the blade portion 104. In one preferred embodiment, the protrusions 1652A, 1652B have contours that match the contours of the valley 126 between two teeth 112 of the blade portion 104.

Figure 24C:
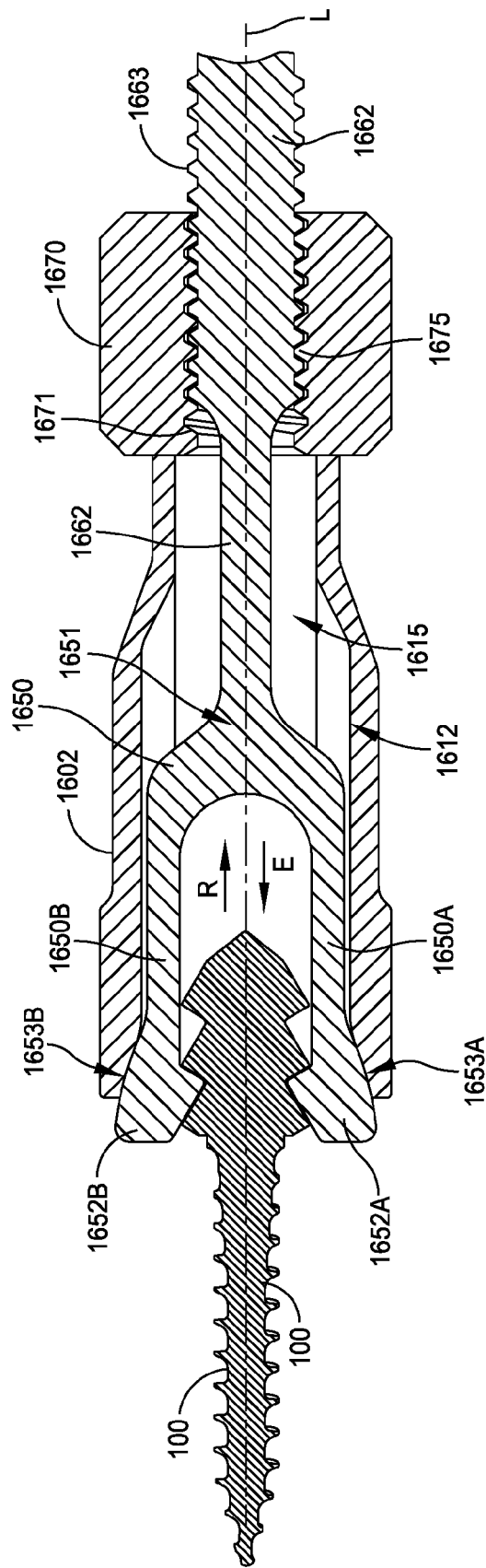
Figure 24D:
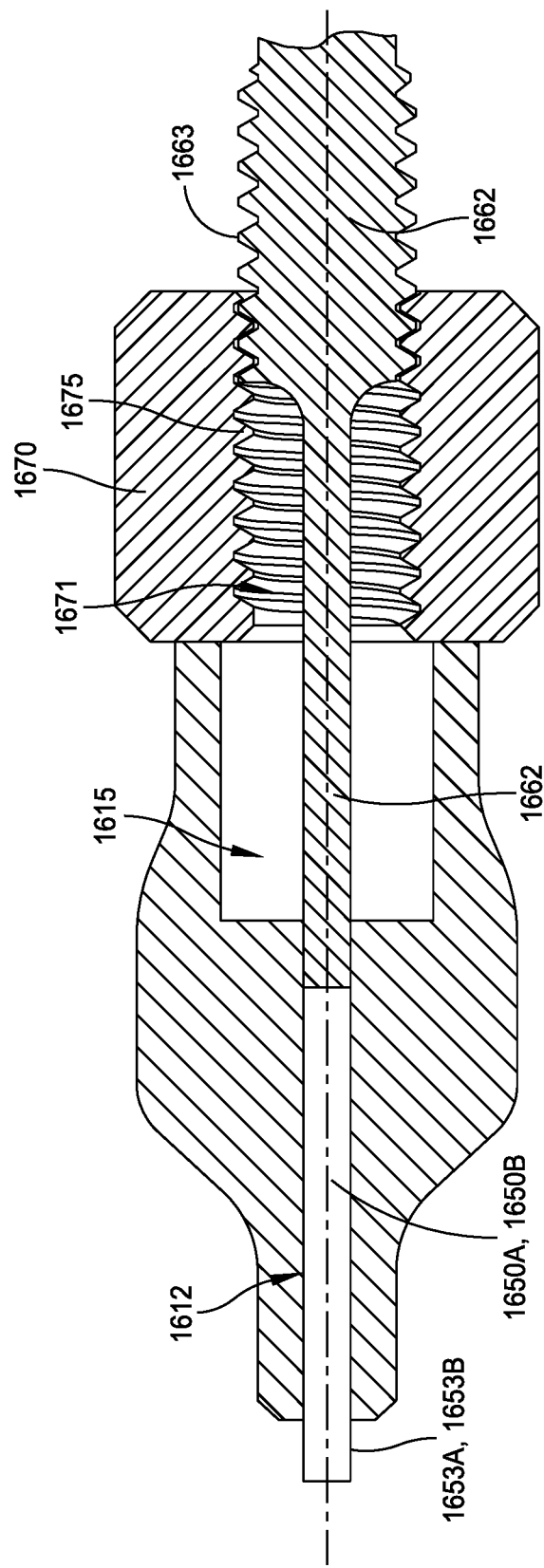

As shown in FIGS. 24B through 24D, the bifurcated arms 1650A and 1650B are joined at the base end 1651. The base portion 1660 comprises a stem portion 1662 that extends from the base end 1651 generally along the longitudinal axis L. The stem portion 1662 is configured with a screw threaded portion 1663. As will be discussed further below, the stem portion 1662 can be configured to couple to the driver shaft of the driver tool in one of a variety of ways.

FIG. 24C shows a longitudinal cross-sectional view of the implant kit 1020 taken through a plane that is parallel to the blade portion 104 and FIG. 24D shows a longitudinal cross-sectional view of the implant kit 1020 taken through a plane that is orthogonal to the blade portion 104. The bifurcated retaining clip 1650 is shown in its normal retracted position within the slot 1612 of the adapter body 1602 with the blade portion 104 of the implant 100 captured and retained in between the bifurcated arms.

The respective outer sides 1653A, 1653B of the two bifurcated arms 1652A, 1652B are slanted at an angle flaring out away from the longitudinal axis L of the implant kit so that the overall width of the bifurcated retaining clip 1650 between the outer sides 1653A, 1653B increase towards the leading ends 1650AA, 1650BB of the bifurcated arms. The bifurcated arms 1650A, 1650B operate in a similar manner to the bifurcated arms 650A, 650B of the implant kit 1010 with respect to capturing and retaining the implant 100. When the bifurcated retaining clip 1650 is in fully retracted position as shown in FIGS. 24A-24D, the bifurcated arms squeeze close and grip the blade portion 104 and retain the implant 100 in the adapter 1600 and cannot be decoupled from the adapter until the bifurcated retaining clip 1650 is extended out.

At the end opposite from the slot opening 1612A, the adapter body 1602 is configured with a cylindrical cavity 1615 and is provided with a retaining nut 1670. The retaining nut 1670 has a threaded longitudinal bore 1671 for threadably receiving the screw threaded portion 1663 of the stem portion 1662 of the bifurcated retaining clip. The stem portion 1662 extends through the cylindrical cavity 1615 and the threaded portion 1663 extends through the threaded bore 1671 of the retaining nut 1670.

The retaining nut 1670 is coupled to the adapter body 1602 in a manner that allows the retaining nut 1670 to be rotatable about the longitudinal axis L of the adapter 1600. The particular structures for the rotatable coupling between the retaining nut 1670 and the adapter body 1602 can be one of a variety of known structures. By turning the retaining nut 1670 in one direction, the bifurcated retaining clip 1650 can be moved in the direction R shown in FIG. 24C and be retracted into the adapter body 1602 for retaining the implant 100. Conversely, by turning the retaining nut 1670 in the opposite direction, the bifurcated retaining clip 1650 can be moved in the direction E shown in FIG. 24C and be extended outward in order to release the implant 100. When the bifurcated retaining clip 1650 is in extended position, it looks similar to the extended configuration of the implant kit 1010 shown in FIG. 23D.

FIGS. 25A-25D are various views of an embodiment of an implant kit 1030 comprising an adapter 2600 configured for coupling to a hammer toe implant 100 using a thread-biased collet 2650. The adapter 2600 comprises a sleeve 2602 and the collet 2650. The sleeve 2602 has openings at each end and a bore 2615 longitudinally extending between the two openings. The collet 2650 is received in the bore 2615. The sleeve 2602 has a first end 2603 that forms one of the openings.

Figure 25A:
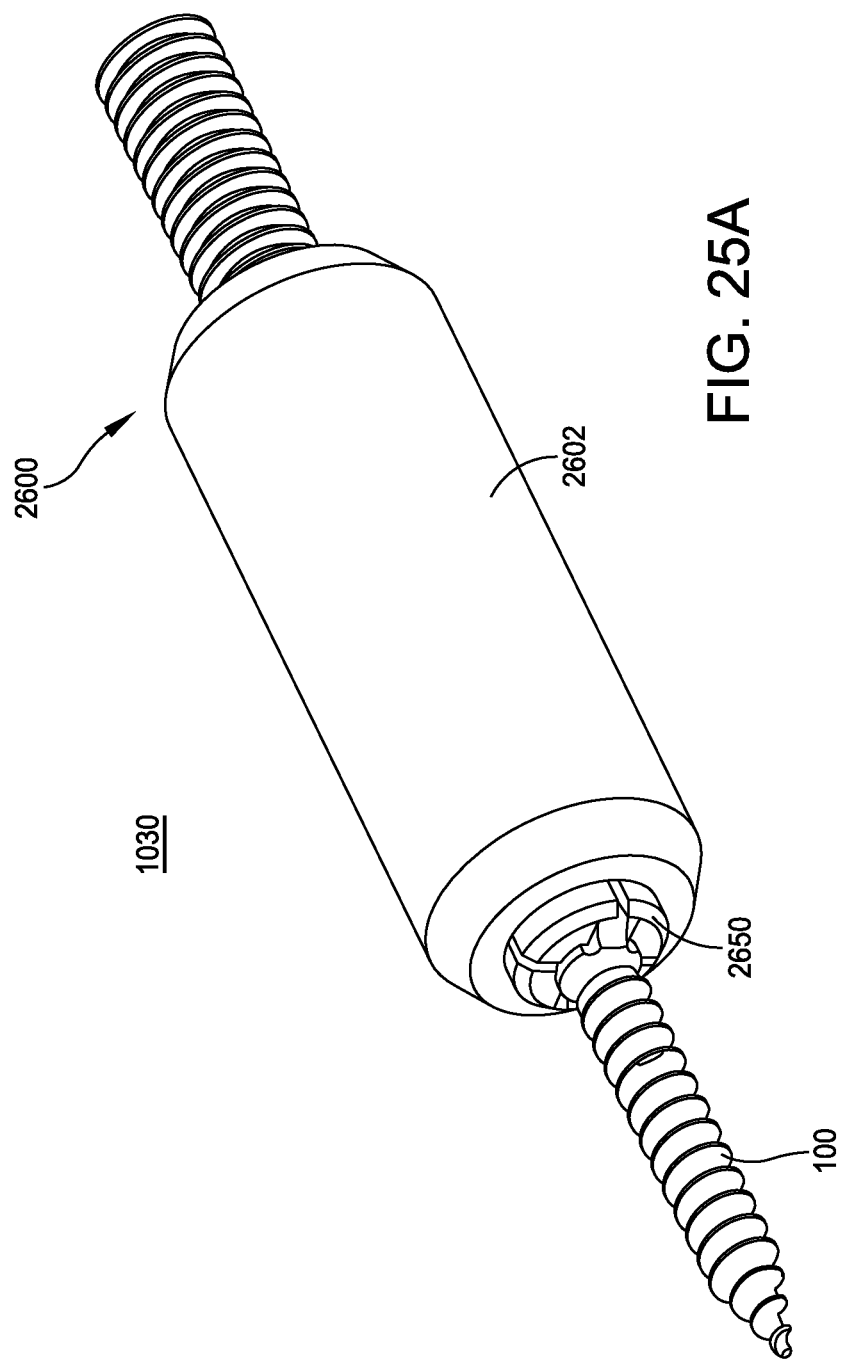
FIGS. 25A-25D are various views of an embodiment of an implant kit comprising an adapter that is configured for coupling to an hammer toe implant using a collet.
Figure 25B:
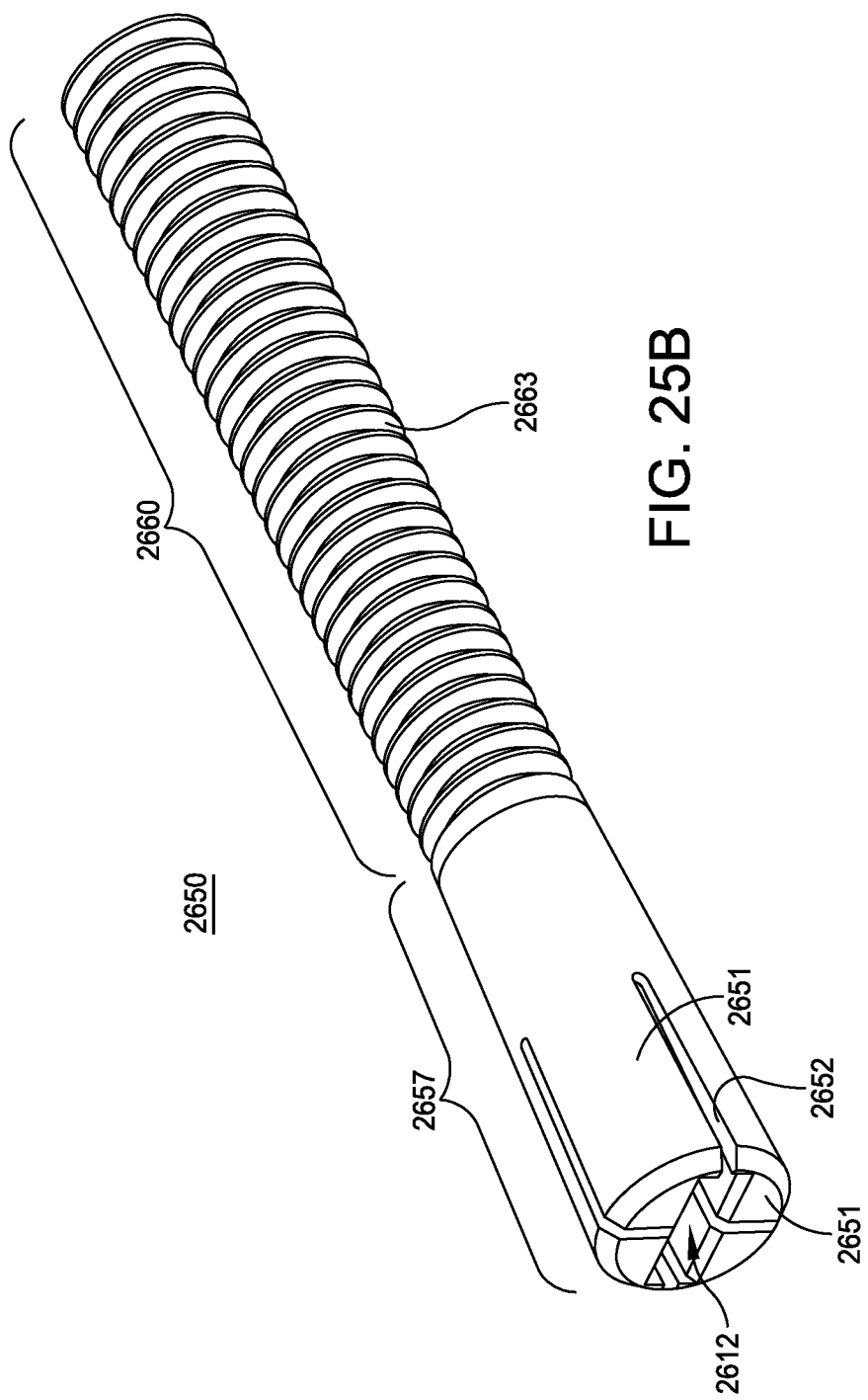
Figure 25C:
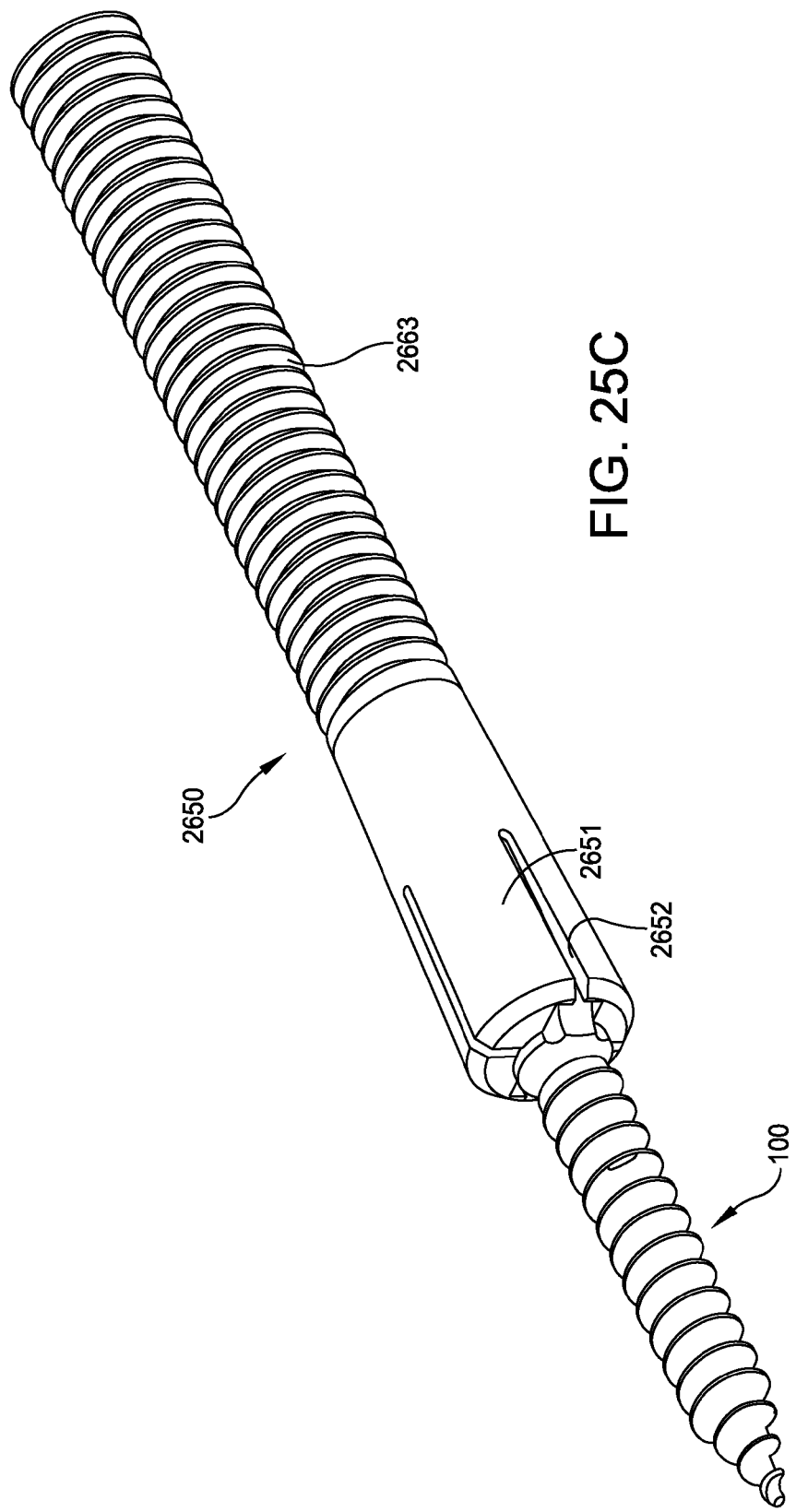

Referring to FIG. 25B, the collet 2650 is generally cylindrical in shape and comprises an implant receiving portion 2657 and a threaded portion 2660. The threaded portion 2660 is provided with screw threads 2663. The implant receiving portion 2657 has an implant-receiving opening 2612 for receiving the blade portion 104 of the implant 100. The implant-receiving opening 2612 is defined by a plurality of collet segments 2651 which are defined by slots 2652 extending from the implant-receiving end towards the threaded portion 2660. This example of a collet has four collet segments 2651. The implant receiving portion 2657 is flared in its outer circumference so that the diameter of the receiving portion 2657 increases towards the implant-receiving end of the collet. FIG. 25C shows the collet 2650 with the implant 100 received in the slot 2652.

Figure 25D:
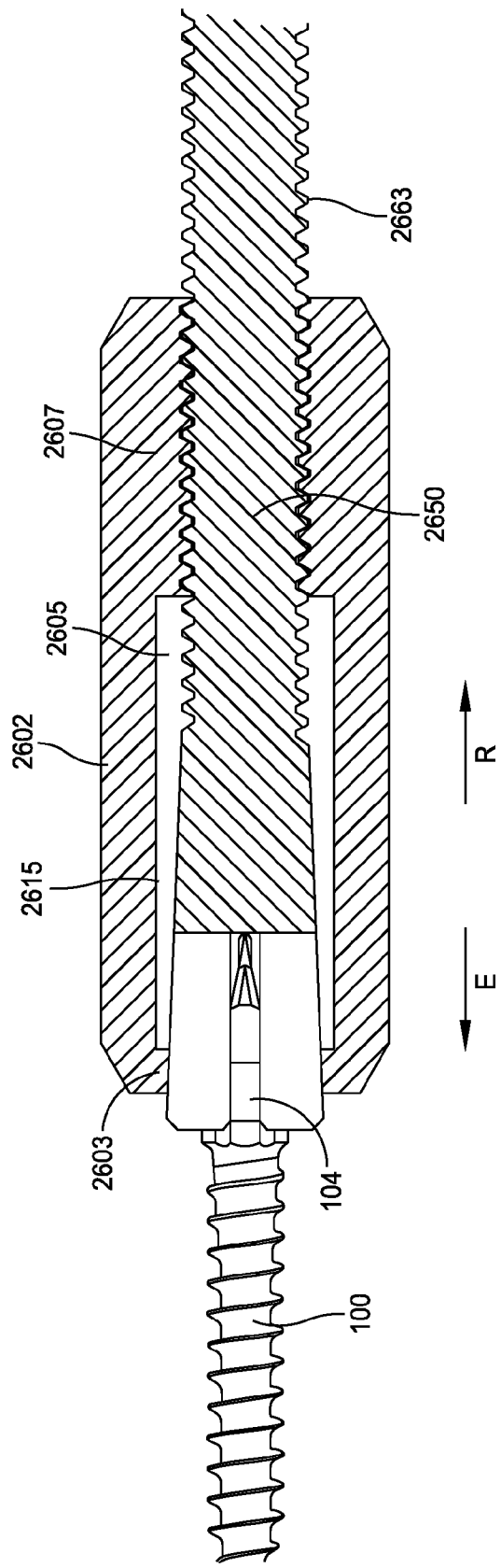

Referring to FIG. 25D, the bore 2615 has a screw threaded portion 2607 and a main portion 2605. The threaded portion 2607 is configured to threadably engage the threads 2663 of the collet 2650. The main portion 2605 has a sufficiently large diameter to accommodate a substantial portion of the implant receiving portion 2657 of the collet 2650 without imposing any mechanical interference. The main portion 2605 terminates at the first end 2603 where the opening formed therein has a diameter smaller than the maximum diameter of the flared implant receiving portion 2657. This configuration allows the collet segments 2651 to be constricted by the first end 2603 when the collet 2650 is retracted into the sleeve 2602 in the direction R shown in FIG. 25D and close in on the blade portion 104 of the implant 100, thus, retaining the implant. Conversely, the implant 100 can be released from the adapter 2600 by extending the collet 2650 outward from the sleeve 2602 in the direction E shown in FIG. 25D. The retraction and extension of the collet 2650 is enabled by turning the sleeve 2602 about the longitudinal axis L relative to the collet 2650 thus engaging the screw threads 2607 and 2663.

Figure 26A:
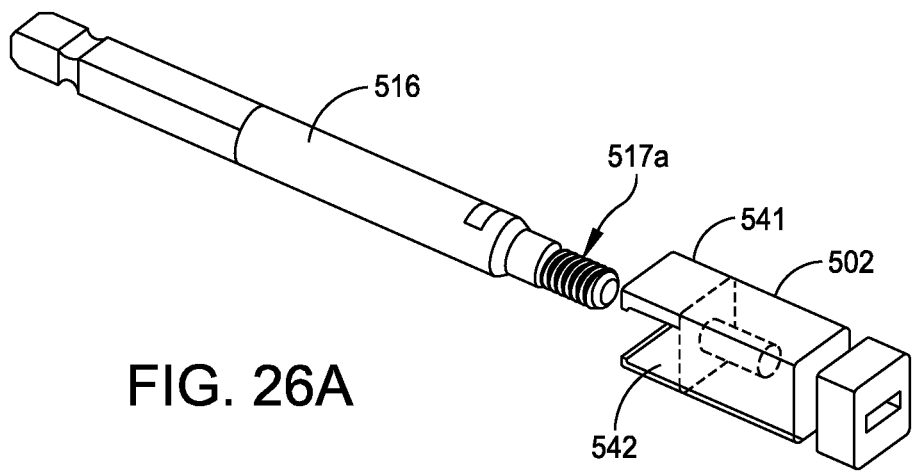
FIGS. 26A-26D are various views of an implant kit according to an embodiment whose adapter has an implant receiving end configured to couple to an implant by an O-ring according to the adapter of FIGS. 13, 21A and 21B and having a driver shaft coupling end configured for coupling to the driver shaft by a pair of opposing tabs.
Figure 26B:
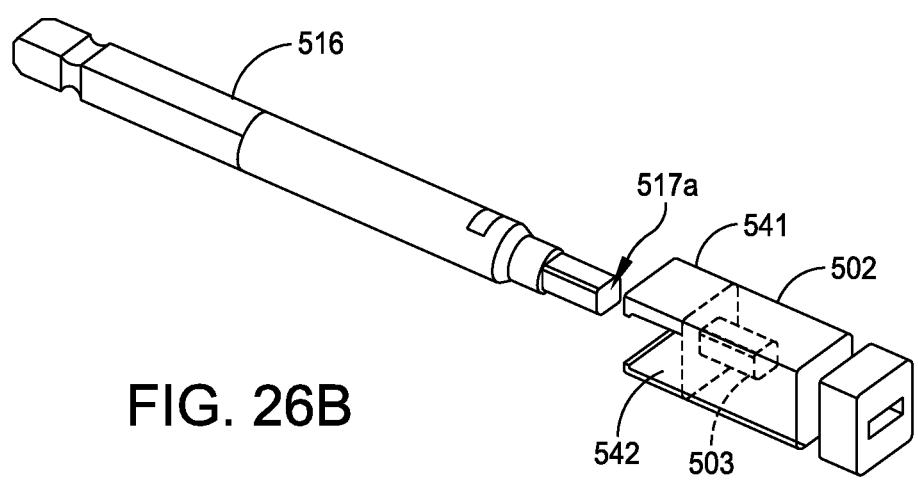

Referring to FIGS. 26A through 41C, various embodiments for removably coupling the implant kits disclosed above to a driver shaft 516 of a driver tool 500 will be described. FIGS. 26A-26D are various views of an embodiment of an adapter such as the adapter 502 of FIGS. 20A-21 having a driver shaft coupling end configured for coupling to the adapter-engaging end 517a, 517b of the driver shaft. The driver shaft coupling end of the adapter 502 is provided with the longitudinally extending bore 514, configured for receiving the adapter-engaging end 517a, 517b, and a pair of opposing tabs 541, 542 extending longitudinally in the direction away from the implant engaging end. FIG. 26A shows a driver shaft 516 whose adapter-engaging end 517a is configured with screw threads. In this embodiment, the driver-engaging end of the adapter 502 is configured to threadably couple to the adapter-engaging end 517a of the driver shaft 502 and the tabs 541, 542 provide additional locking mechanism. FIG. 26B shows a driver shaft 516 whose adapter-engaging end 517b is configured with a magnetic tip. In this embodiment, the driver-engaging end of the adapter 502 is configured to magnetically couple to the adapter-engaging end 517b and the tabs 541, 542 provide additional locking mechanism. The adapter 502 would then be provided with a magnet or a piece of magnetic material 503 for magnetically coupling to the adapter-engaging end 517b.

Figure 26C:
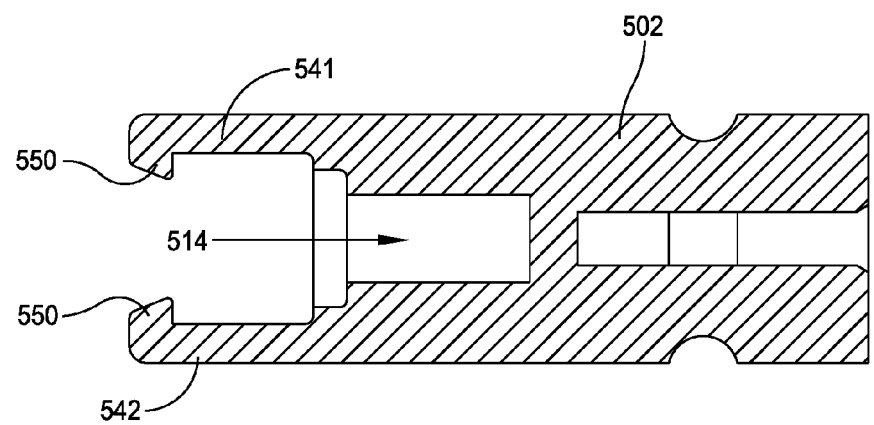
Figure 26D:
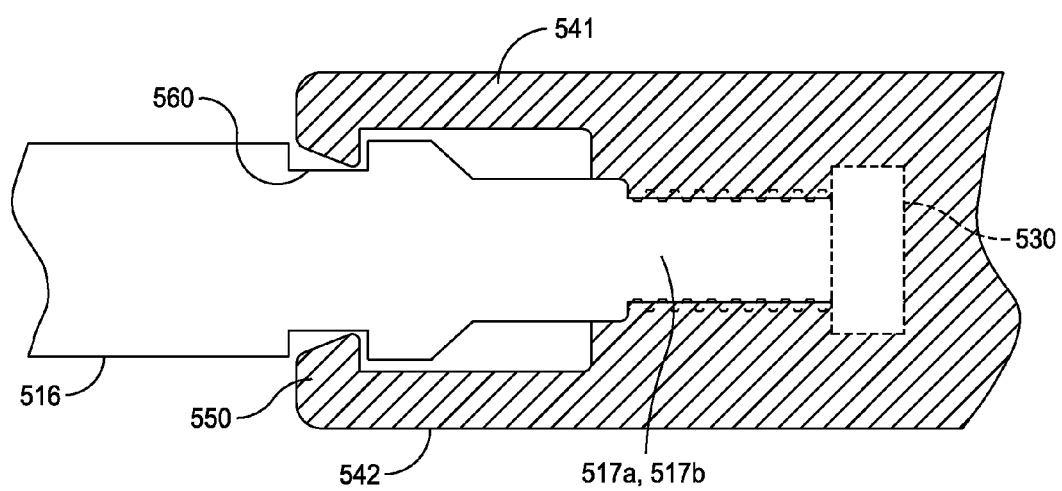

FIGS. 26C and 26D are cross-sectional views of the adapter 502 showing the driver-engaging end. FIG. 26C shows the profile of the tabs 541 and 542 and the bore 514 for receiving the adapter-engaging end 517 of the driver shaft. If the adapter 502 is intended for use with the driver shaft 516 of the embodiment shown in FIG. 26A, the bore 514 is tapped with screw thread for threadably engaging the threaded adapter-engaging end 517a. If the adapter 502 is intended for use with the driver shaft 516 of the embodiment shown in FIG. 26B, the bore 514 is provided with a magnet 530 for engaging the magnetized tip of the adapter-engaging end 517b.

The tabs 541, 542 and the adapter-engaging end 517a, 517b are configured for further mechanical coupling. In the illustrated example, the tabs 541, 542 are provided with bumps 550 and the adapter-engaging end 517a, 517b of the driver shaft is provided with corresponding cutouts 560 for mating with the bumps 550.

Figure 27A:
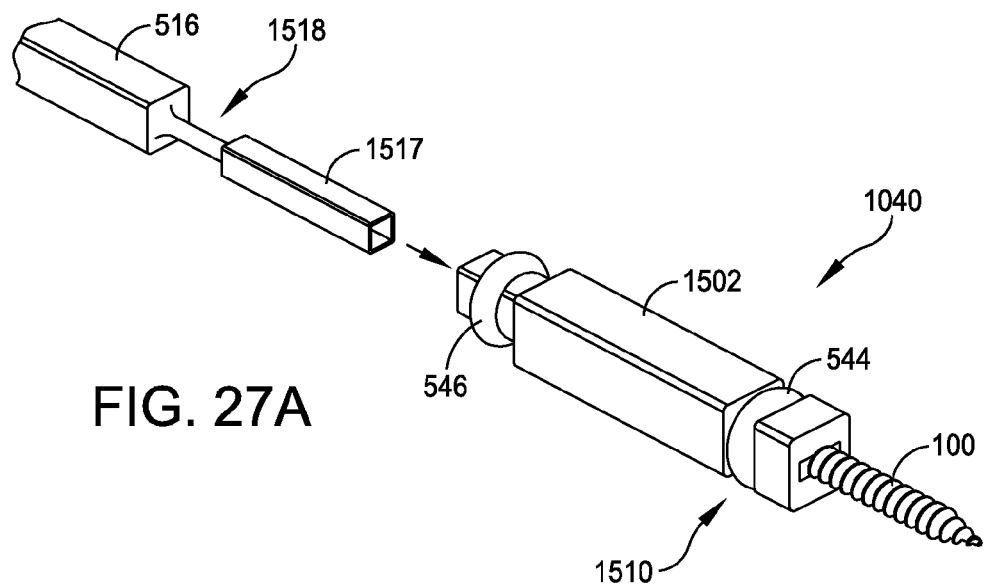
FIGS. 27A-27C are various views of an implant kit according to an embodiment whose adapter has an implant receiving end configured to couple to an implant by an O-ring according to the adapter of FIGS. 13, 21A and 21B and having a driver shaft coupling end configured for coupling to the driver shaft by an O-ring.
Figure 27B:
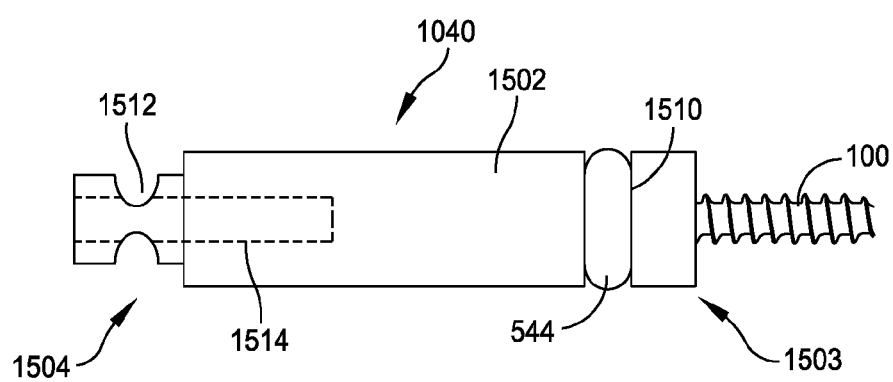
Figure 27C:
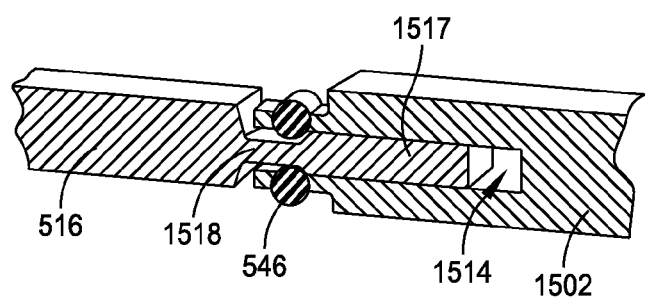

Shown in FIGS. 27A-27C are various views of an implant kit 1040 comprising an adapter 1502 and an implant 100 according to another embodiment. The implant 100 is removably coupled to the adapter 1502 at the adapter's implant-receiving end 1503 by a first O-ring 544 in the same manner as with the adapter 502 shown in FIGS. 13, 20A, 20B and 21. The adapter 1502 has a circumferential groove 1510, in which the first O-ring 544 is provided, in the outer surface of the adapter in proximity to the implant-receiving end 1503. As with the adapter embodiment 502, the adapter 1502 comprises a slot provided in the implant-receiving end 1503 that receives the blade portion 104 of the implant 100. The adapter 1502 also has a driver shaft coupling end 1504 configured for removably coupling to the driver shaft 516 by a second O-ring 546. The driver shaft coupling end 1504 is provided with a longitudinally extending bore 1514 for receiving the adapter-engaging end 1517 of the driver shaft 516. The driver shaft coupling end 1504 is also provided with a second circumferential groove 1512 in which the second O-ring 546 is disposed. The adapter-engaging end 1517 has a cross-section that is larger than the inner diameter of the second O-ring 546 but has a turned down section 1518 that has a reduced cross-section for accommodating the second O-ring 546 when the adapter-engaging end 1517 is inserted into the bore 1514 as shown in FIG. 27C. When the adapter-engaging end 1517 is inserted into the bore 1514, the turned down section 1518 and the second circumferential groove 1512 align so that the second O-ring 546 rests in the turned down section 1518. The second O-ring 546 thus provides an interference with the adapter-engaging end 1517 to prevent the adapter 1502 and the driver shaft 516 from decoupling without exerting some force.

Figure 28A:
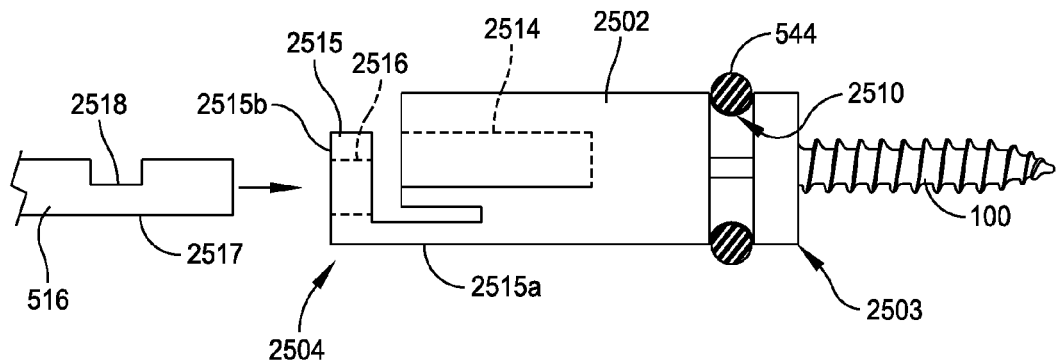
FIGS. 28A-28C are various views of an implant kit according to an embodiment whose adapter has an implant receiving end configured to couple to an implant by an O-ring according to the adapter of FIGS. 13, 21A and 21B and having a driver shaft coupling end configured for coupling to the driver shaft by an off-set clip.
Figure 28B:
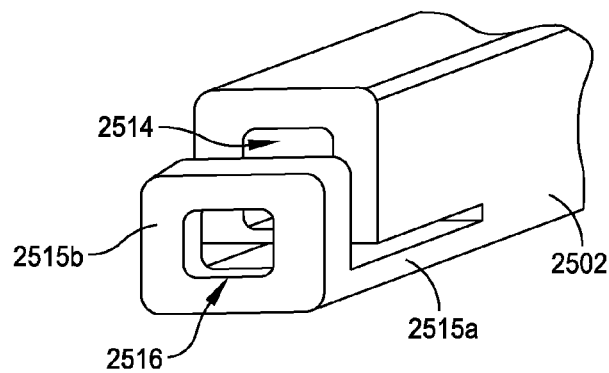
Figure 28C:
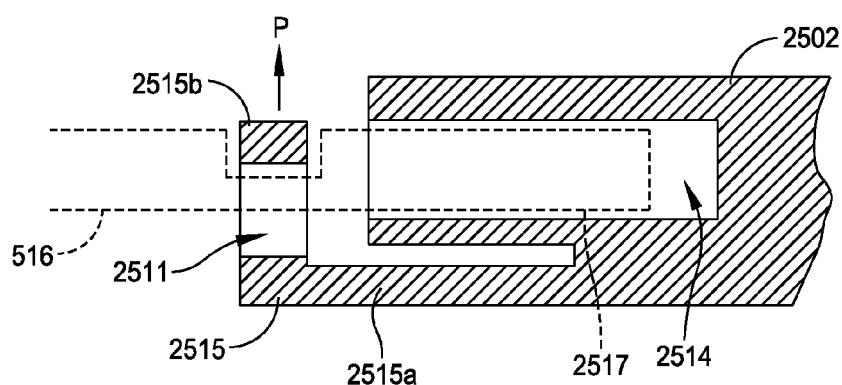

FIGS. 28A-28C are various views of an adapter 2502 that can be used in an implant kit 1050 according to another embodiment of the present disclosure. The adapter 2502 has an implant receiving end 2503 configured to couple to an implant 100 by an O-ring 544 according to the adapter of FIGS. 13, 21A and 21B and a driver shaft coupling end 2504 configured for coupling to the driver shaft 516 by an off-set clip 2515. The driver shaft coupling end 2504 has a longitudinally extending bore 2514 for receiving an adapter-engaging end 2517 of the driver shaft 516. The off-set clip 2515 is cantilevered to the adapter having a cantilever portion 2515a connected to the adapter body and a locking portion 2515b extending orthogonal to the cantilever portion 2515a. The locking portion 2515b is provided with a through hole 2516 for the adapter-engaging end 2517 of the driver shaft 516. The through hole 2516 and the bore 2514 are off-set to enable the locking function. The adapter-engaging end 2517 is provided with a groove or a cutout 2518 on one side for removably engaging the off-set clip 2515. To insert the adapter-engaging end 2517 into the adapter, the user pushes the off-set clip 2515 in the direction shown by the arrow P in FIG. 28C, which is a longitudinal cross-sectional view of the adapter 2502. That will deflect the cantilever portion 2515a in the direction P and bring the through hole 2516 in linear alignment with the bore 2514 so that the adapter-engaging end 2517 can be inserted through the through hole 2516 and the bore 2514. Once the adapter-engaging end 2517 is fully inserted, the off-set clip 2515 is released to its normal off-set position as shown in FIG. 28C. The off-set position of the locking portion 2515b keeps the locking portion 2515b seated within the cutout 2518 keeping the driver shaft 516 coupled to the adapter 2502. The off-set clip can be configured so that in the configuration shown in FIG. 28C, the locking portion 2515b maintains a force against the cutout 2518 in the direction opposite the arrow P. To remove the adaper 2502 from the adapter-engaging end 2517, the off-set clip 2515 is pushed in the direction of the arrow P shown in FIG. 28C bringing the through hole 2516 and the bore 2514 into longitudinal alignment and thus removing the interference between the locking portion 2515b and the cutout 2518. In another embodiment, the adapter-engaging end 2517 may simply be straight without the cutout 2518 structure. In that embodiment, the urging of the locking portion 2515b against the straight adapter-engaging end 2517 in the direction opposite the arrow P will provide sufficient frictional interference to keep the driver shaft 516 and the adapter 2502 coupled.

Figure 29A:
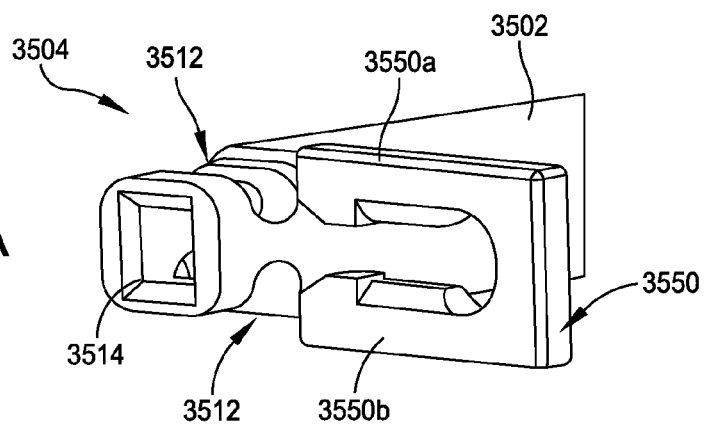
FIGS. 29A-29E are various views of an implant kit according to an embodiment whose adapter has an implant receiving end configured to couple to an implant by an O-ring according to the adapter of FIGS. 13, 21A and 21B and having a driver shaft coupling end configured for coupling to the driver shaft by a C-clip.
Figure 29B:
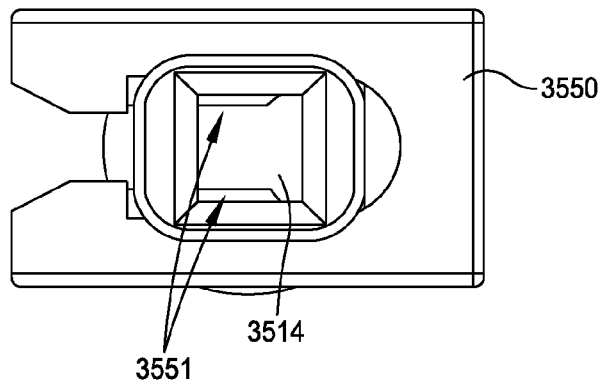
Figure 29C:
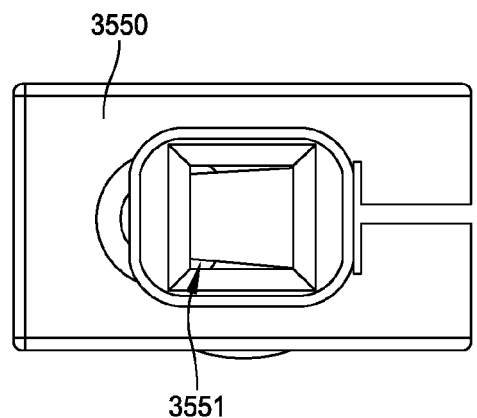
Figure 29E:
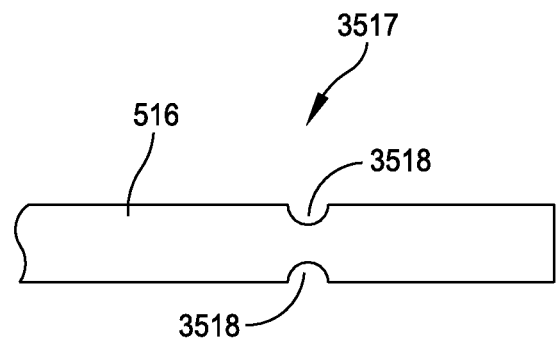
Figure 29D:
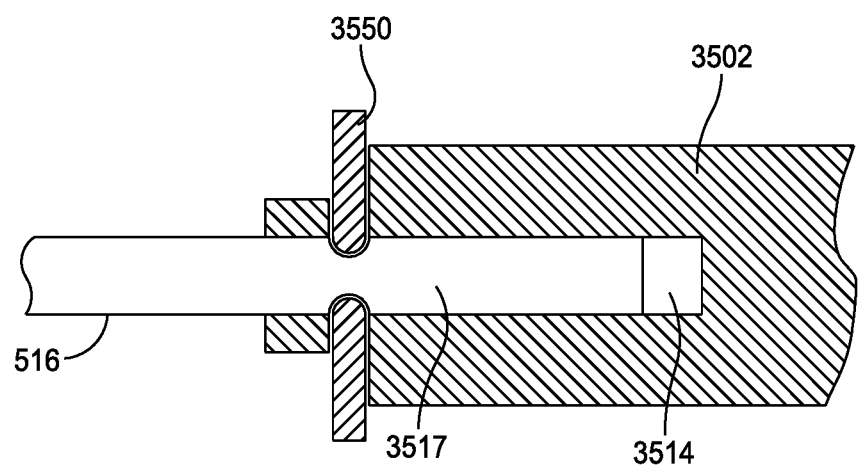

FIGS. 29A-29E are various views of the driver shaft coupling end 3504 of an adapter 3502 that is configured for removably coupling to the implant 100 to form an implant kit according to another embodiment. The implant-receiving end of the adapter 3502 is configured to couple to the implant by an O-ring 544 according to the adapter of FIGS. 13, 21A and 21B. The driver shaft coupling end 3504 is configured to removably couple to the adapter-engaging end 3517 of the driver shaft 516 by a C-clip 3550. The C-clip 3550 is generally shaped like a letter C and has two prongs 3550a and 3550b joined at one end and open at the opposite end. The driver shaft coupling end 3504 of the adapter 3502 is provided with a bore 3514 for receiving the adapter-engaging end 3517. The driver shaft coupling end 3504 is further configured with a pair of slots 3512 for receiving the C-clip 3550 and oriented orthogonal to the longitudinal axis of the adapter 3502. FIG. 29B is an end view of the adapter assembly viewed from the driver shaft coupling end 3504 showing the C-clip 3550 clipped on to the adapter 3502 by sliding the two prongs 3550a, 3550b into the pair of slots 3512. The pair of slots 3512 are cut into the adapter 3502 sufficiently deep to overlap with the bore 3514 so that when the C-clip 3550 is clipped on to the adapter 3502, interference tabs 3551 on each of the two prongs 3550a, 3550b protrude into the bore 3514 as shown in FIG. 29B. When the adapter-engaging end 3517 of the driver shaft 516 is inserted into the bore 3514 and locked with the C-clip 3550 as shown in the longitudinal cross-sectional view of FIG. 29E, the interference tabs 3551 reside in the corresponding slots 3518 provided in the adapter-engaging end 3517 and prevent the adapter 3502 and the driver shaft 516 from decoupling. In this embodiment, the interference tabs 3551 are oriented substantially parallel to one another. In one preferred embodiment, the interference tabs 3551 can be oriented in a slant so that the interference tabs 3551 are tapered towards the open end of the C-clip 3550. The tapered interference tabs 3551 makes is easier to insert the C-clip 3550 over the adapter-engaging end 3517.

Figure 30:
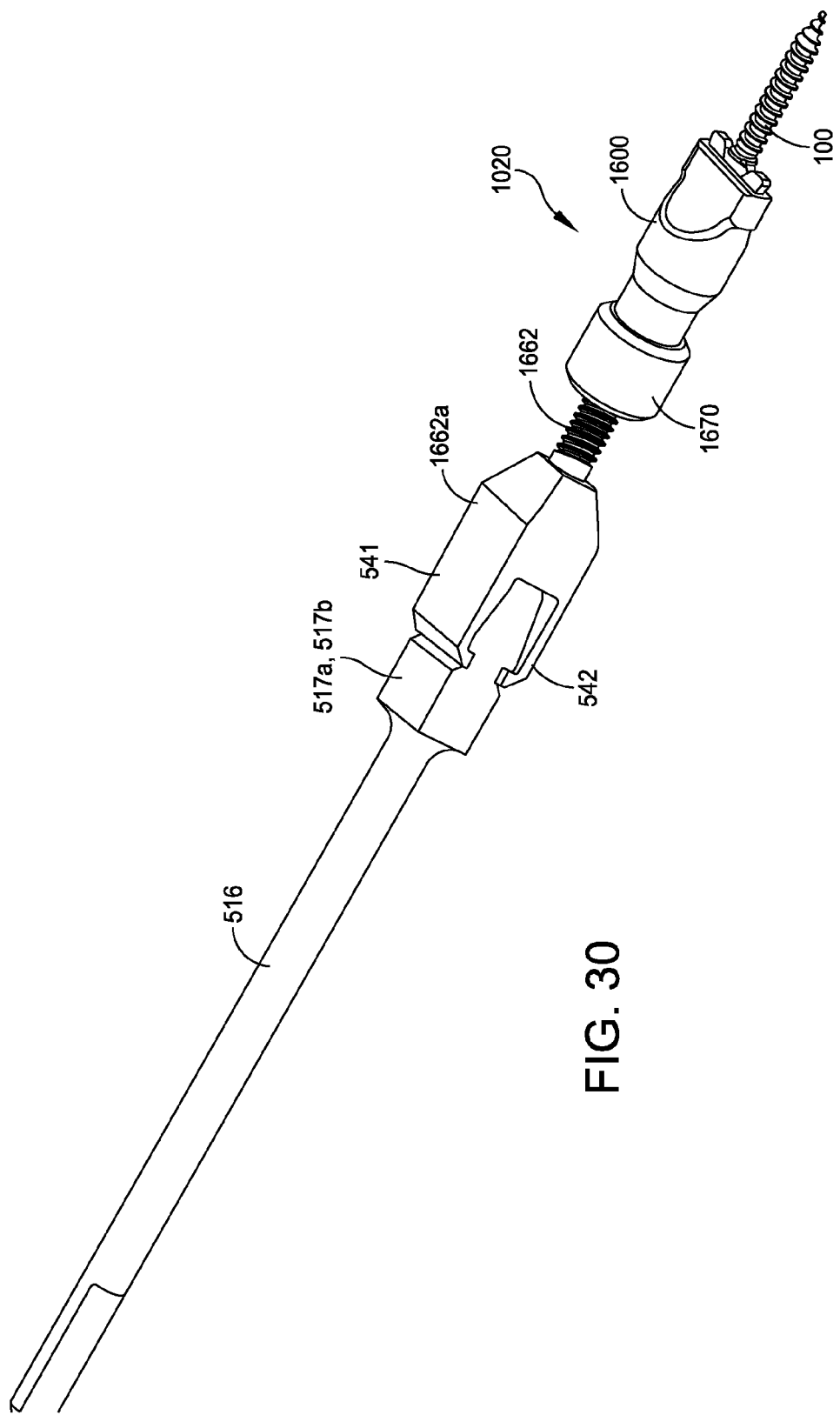
FIG. 30 shows an embodiment of the implant kit comprising an adapter having an implant-receiving end configured according to the adapter of FIG. 24A and having a driver shaft coupling end configured for coupling to the driver shaft by a pair of opposing tabs as shown in FIGS. 26A and 26B.

According to another embodiment, the driver shaft coupling ends of the implant kit 1010 (shown in FIG. 23A), implant kit 1020 (shown in FIG. 24A) can be configured and adapted to removably couple to the adapter-engaging end of the driver shaft 516 by adopting one of the structural configurations described herein. For example, FIG. 30 shows an embodiment where the implant kit 1020 whose driver shaft coupling end 1662a is configured with the pair of opposing tabs 541, 542 as shown in FIGS. 26A-26D and the adapter-engaging end of the driver shaft 516 is configured to have the structures of 517a or 517b as shown in FIGS. 26A-26D.

Figure 31A:
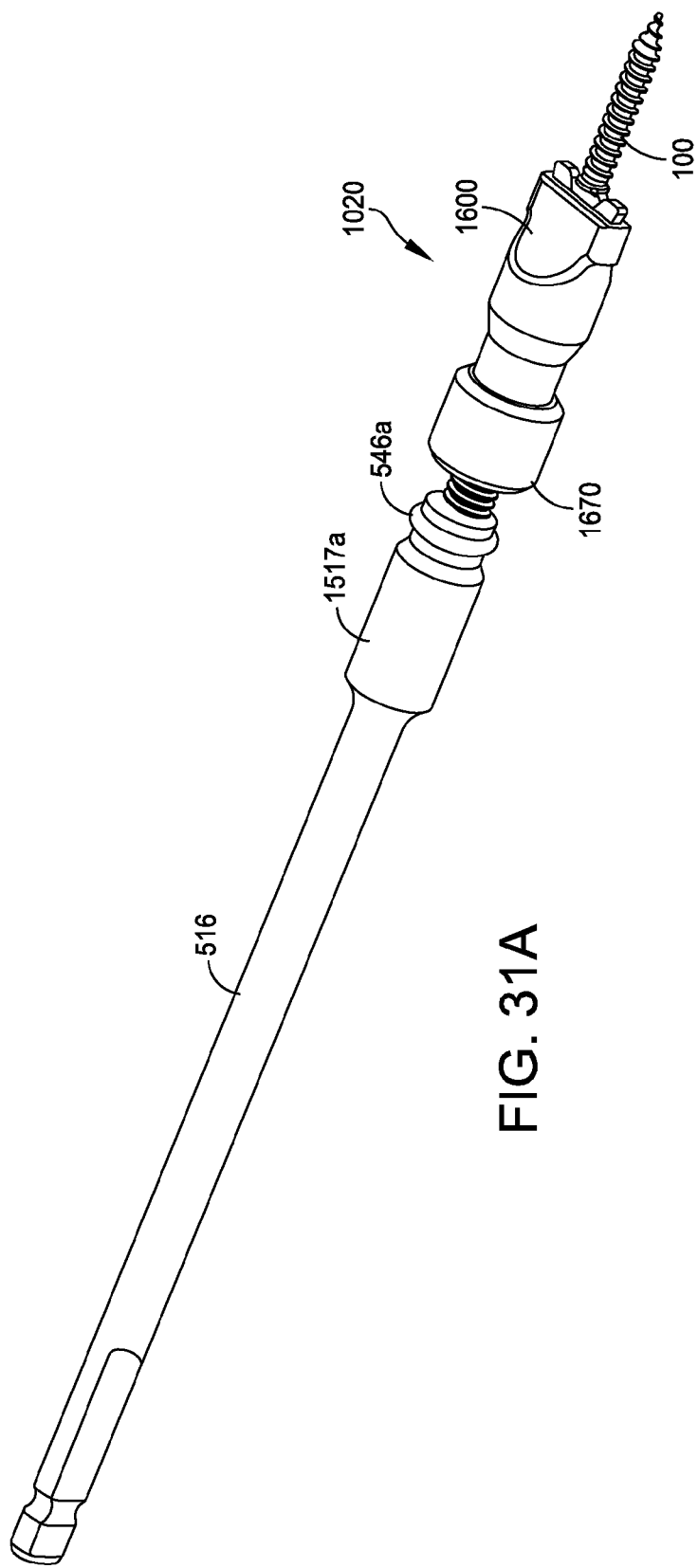
FIGS. 31A-31B are various views of an embodiment of the implant kit comprising an adapter having an implant receiving end configured according to the adapter of FIG. 24A and having a driver shaft coupling end configured for coupling to the driver shaft by an O-ring provided on the driver shaft.
Figure 31B:
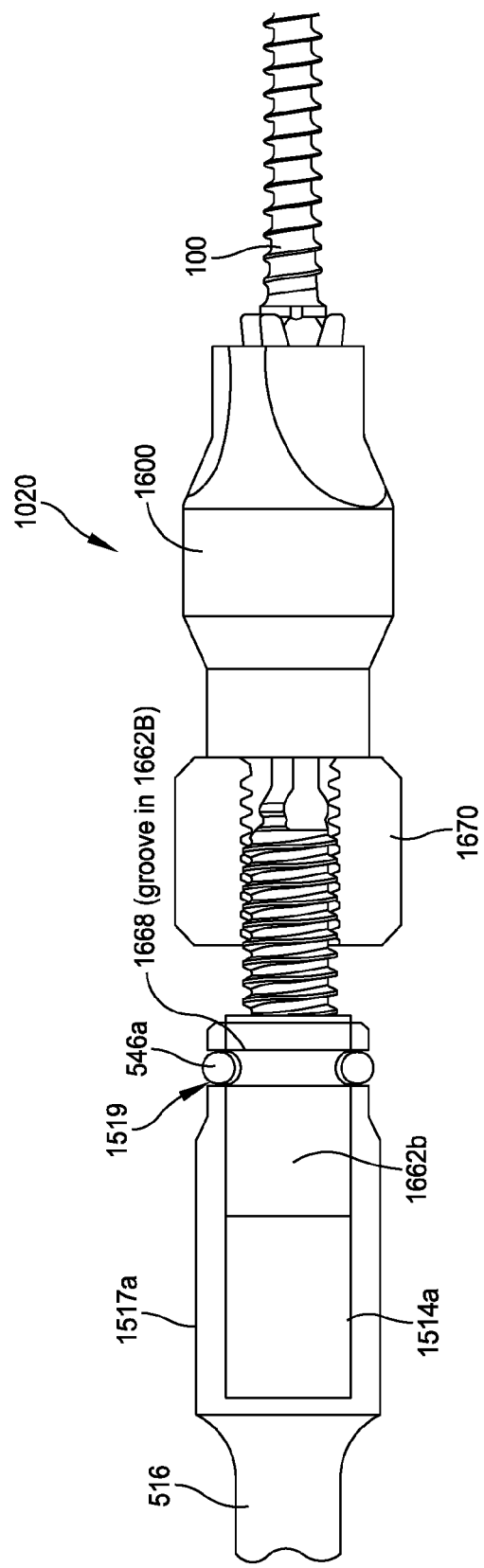

According to another embodiment, FIGS. 31A and 31B show the implant kit 1020 (shown in FIG. 24A) whose driver shaft coupling end 1662b is configured to couple to the driver shaft 516 by an O-ring similar to the structure shown in connection with the implant kit 1040 (shown in FIG. 27A). In this embodiment, however, the structures of the adapter-engaging end 1517a of the driver shaft 516 and the driver shaft coupling end 1662b of the adapter 1600 are switched compared to the structures shown in FIG. 27A. Here, the driver shaft coupling end 1662b is configured for coupling to the driver shaft 516 by an O-ring 546a that is provided on the driver shaft rather than the driver shaft coupling end 1662b of the adapter's stem portion 1662. The adapter-engaging end 1517a of the driver shaft 516 is cylindrical and is provided with a bore 1514a for receiving the driver shaft coupling end 1662b. The adapter-engaging end 1517a is provided with a circumferential groove 1519 for accommodating the O-ring 546a. The driver shaft coupling end 1662b is configured to be a prism-like structure having a square cross-section or some other polygon cross-section and the bore 1514a has a corresponding shape for receiving the polygon shape. This configuration allows torsional force from the driver shaft 516 to be transferred to the driver shaft coupling end 1662b.

Because the adapter-engaging end 1517a is a cylinder, the corners of the polygon shaped driver shaft coupling end 1662b are closer to the outer surface of the adapter-engaging end 1517a and the corners of the polygon shaped driver shaft coupling end 1662b intersect the bottom of the circumferential groove 1519. This creates openings at the bottom of the groove 1519 that expose the driver shaft coupling end 1662b when the driver shaft coupling end 1662b is inserted into the bore 1514a. The driver shaft coupling end 1662b is provided with a groove 1668 that aligns with the circumferential groove 1519 so that the groove 1668 is exposed through the openings at the bottom of the groove 1519 and the O-ring 546a provided in the circumferential groove 1519 of the adapter-engaging end 1517a of the driver shaft retains the driver shaft coupling end 1662b in place.

Figure 32:
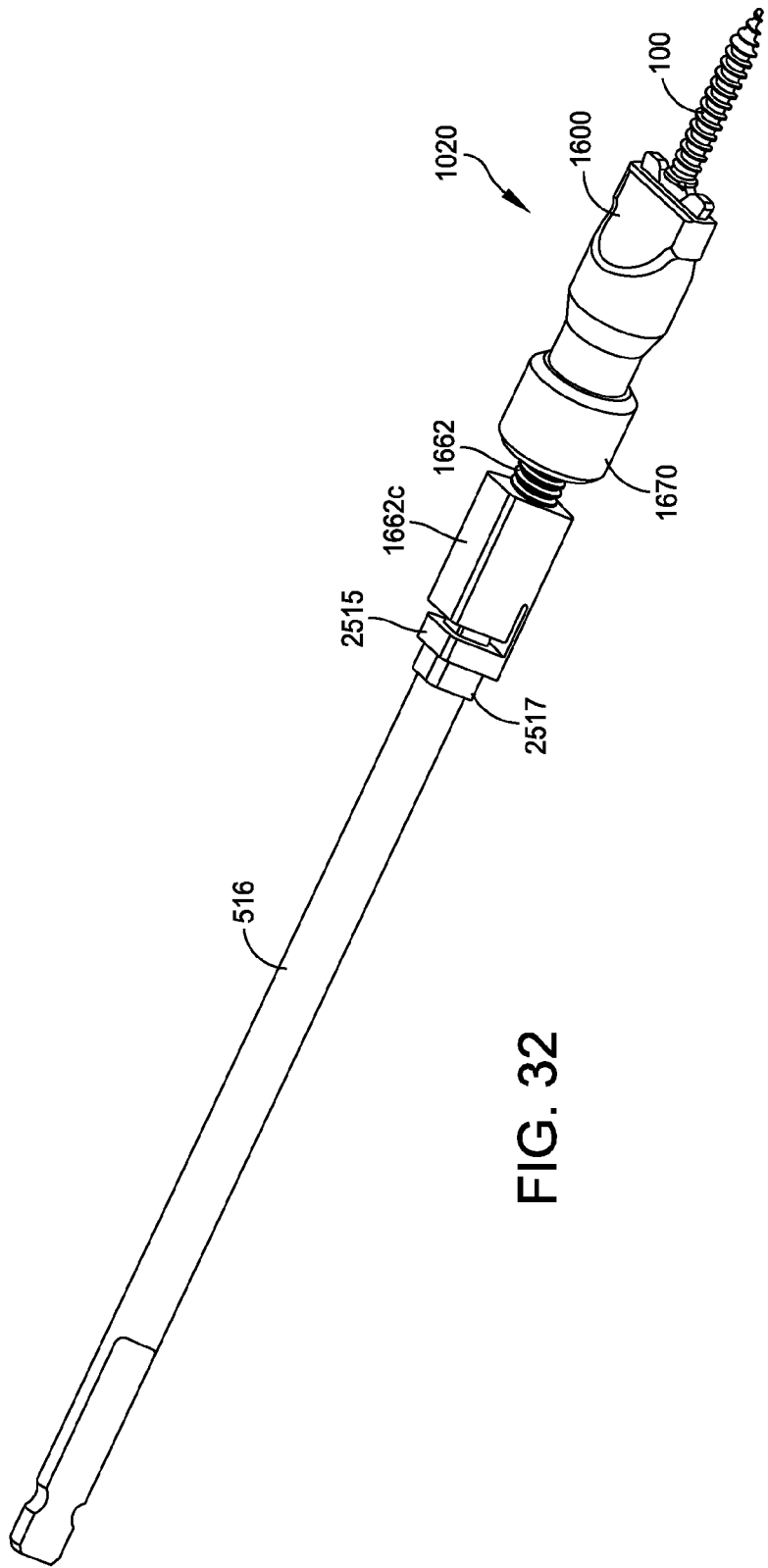
FIG. 32 shows an embodiment of the implant kit comprising an adapter having an implant receiving end configured according to the adapter of FIG. 24A and having a driver shaft coupling end configured for coupling to the driver shaft by an off-set clip shown in the implant kit of FIGS. 28A-28C.

FIG. 32 shows another embodiment of the implant kit 1020 as shown in FIG. 24A that is removably coupled to the driver shaft 516. In this embodiment, the adapter 1600 has an implant receiving end structure as shown in FIG. 24A and a driver shaft coupling end 1662c that is configured with the off-set clip structure 2515 for coupling to the adapter-engaging end 2517 of the driver shaft 516. The off-set clip structure 2515 is as used in the implant kit 1050 as shown in FIGS. 28A-28C.

Figure 33:
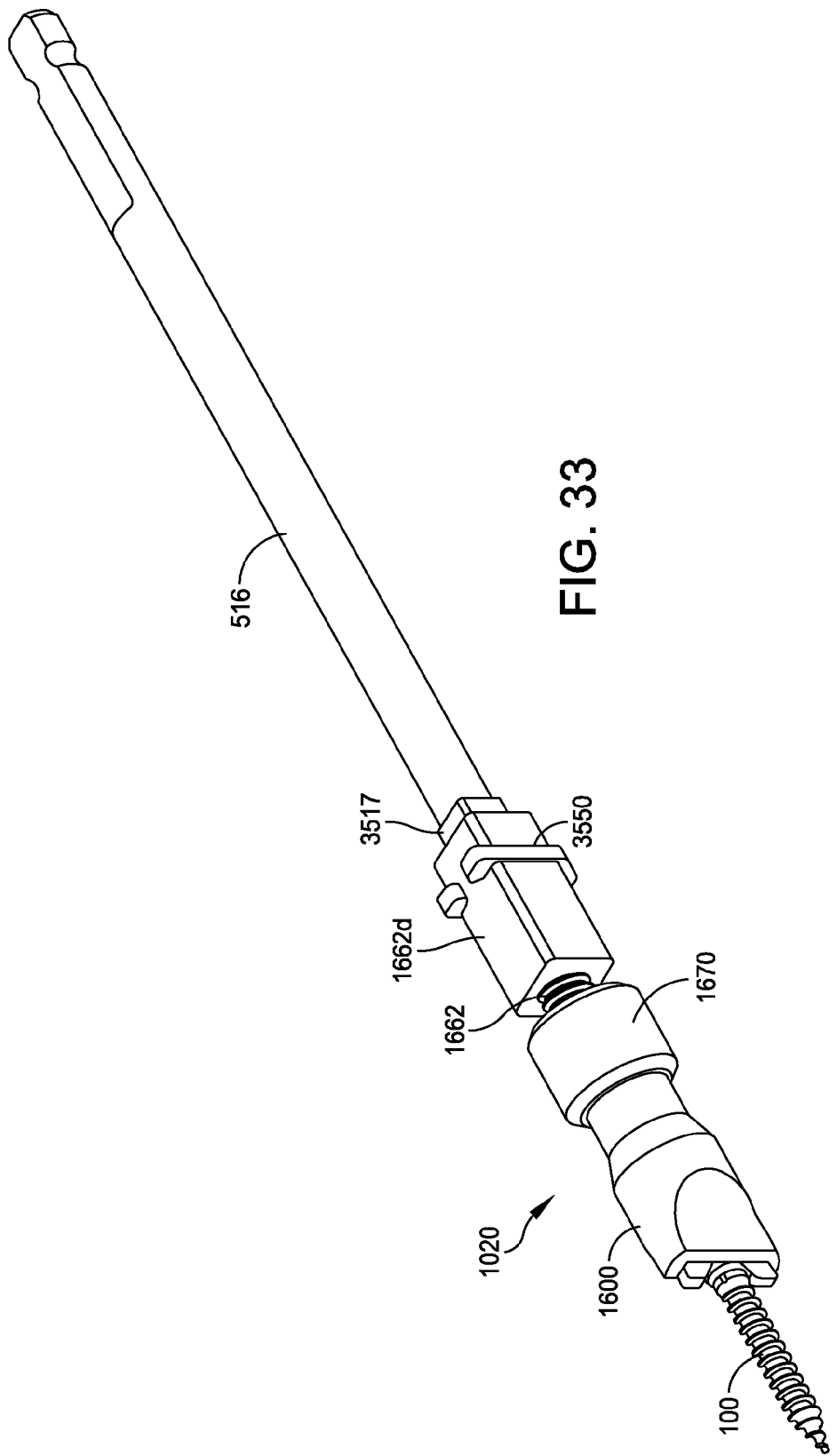
FIG. 33 shows an embodiment of the implant kit comprising an adapter having an implant receiving end configured according to the adapter of FIG. 24A and having a driver shaft coupling end configured for coupling to the driver shaft by a C-clip shown in FIGS. 29A-29E.

FIG. 33 shows another embodiment of the implant kit 1020 as shown in FIG. 24A that is removably coupled to the driver shaft 516. In this embodiment, the adapter 1600 has an implant receiving end structure as shown in FIG. 24A and a driver shaft coupling end 1662d that is configured with the C-clip structure 3550 as shown in FIGS. 29A-29E for coupling to the adapter-engaging end 3517 of the driver shaft 516.

Figure 34:
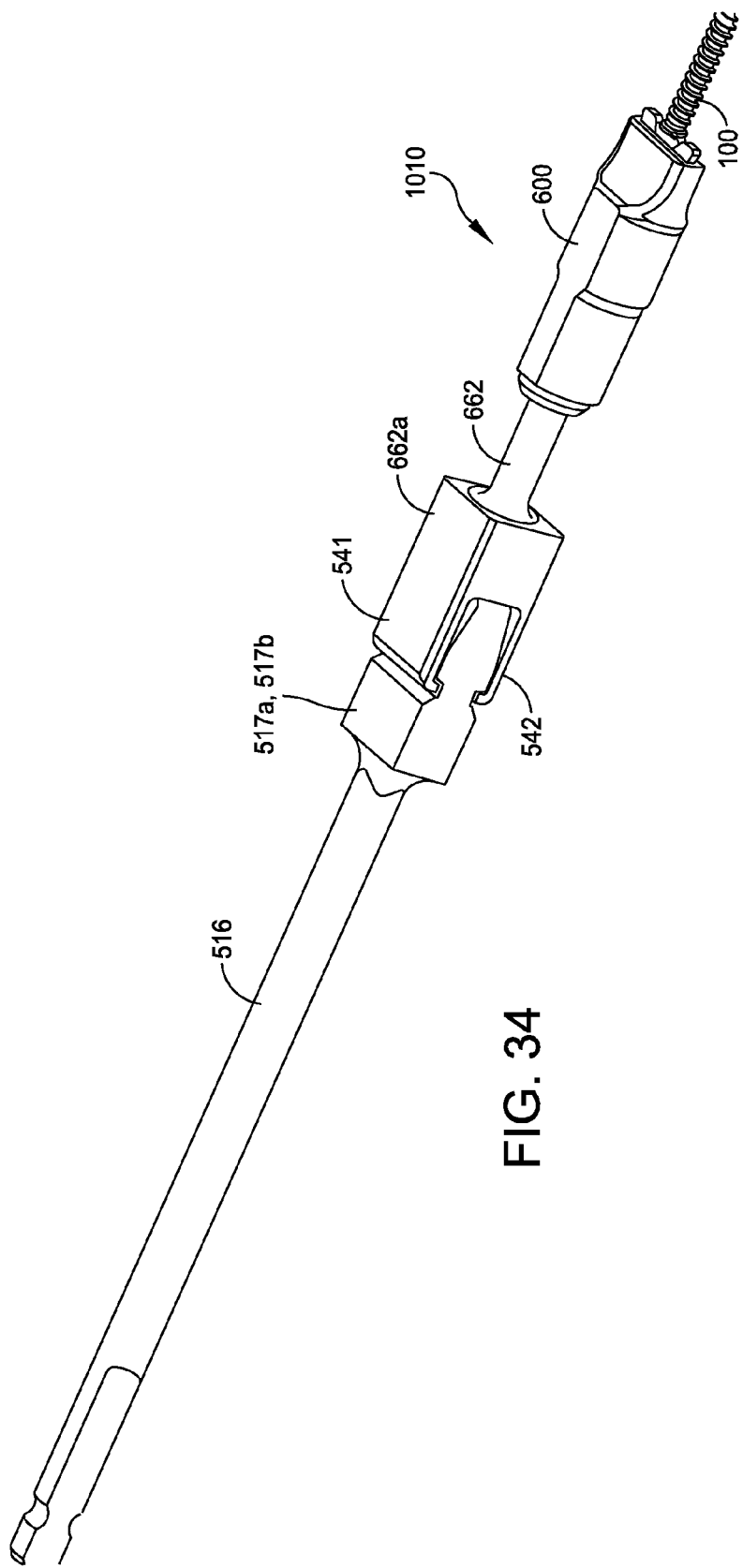
FIG. 34 shows an embodiment of the implant kit comprising an adapter having an implant receiving end configured according to the adapter of FIG. 23A and having a driver shaft coupling end configured for coupling to the driver shaft by a pair of opposing tabs shown in FIGS. 26A, 26B.

FIG. 34 shows an embodiment where the implant kit 1010 of FIGS. 23A-23C whose driver shaft coupling end 662a is configured with the pair of opposing tabs 541, 542 as shown in FIGS. 26A-26D and the adapter-engaging end of the driver shaft 516 is configured to have the structures of 517a or 517b as shown in FIGS. 26A-26D.

Figure 35A:
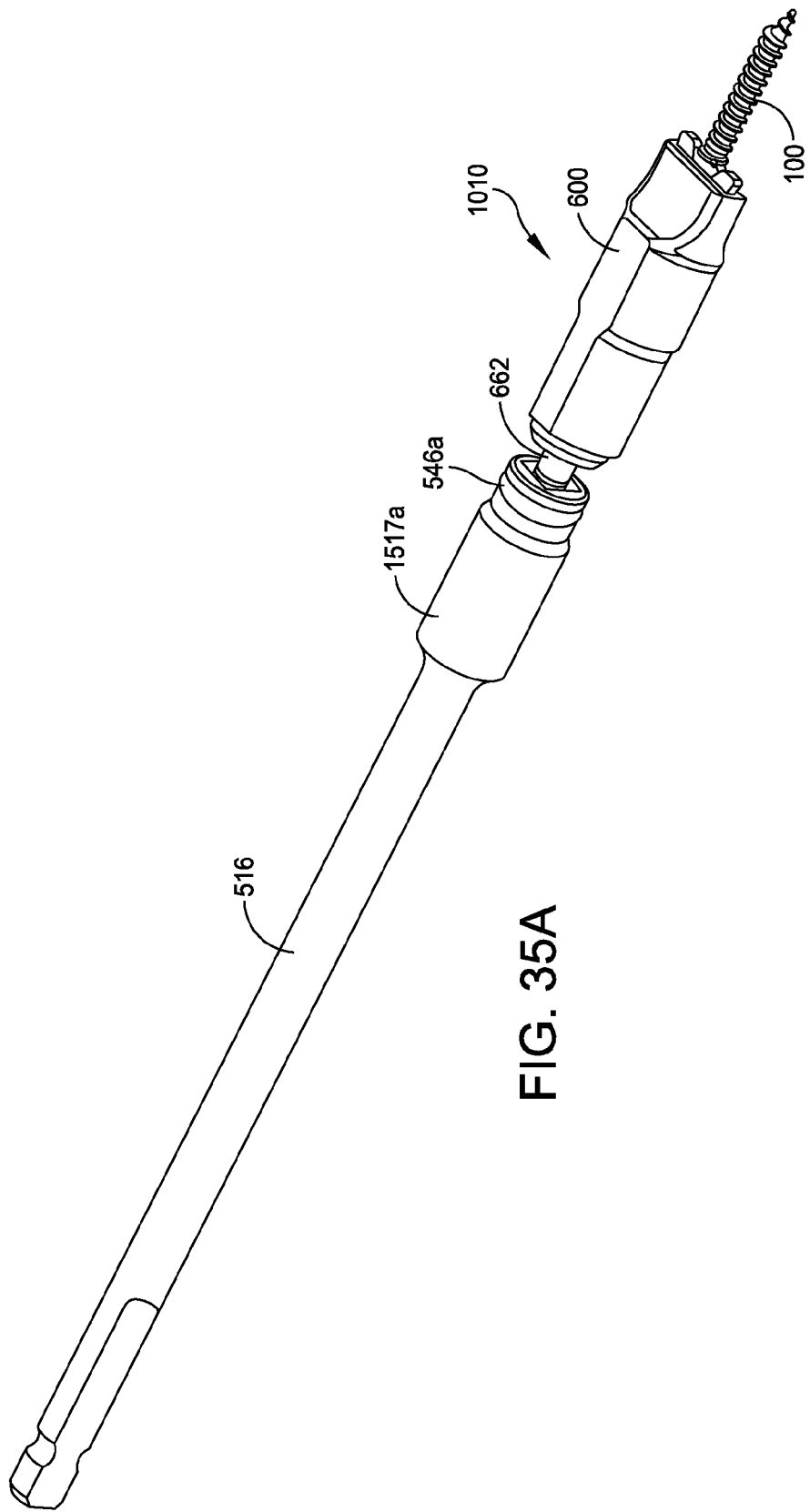
FIGS. 35A-35B show an embodiment of the implant kit comprising an adapter having an implant receiving end configured according to the adapter of FIG. 23A and having a driver shaft coupling end configured for coupling to the driver shaft by an O-ring provided on the driver shaft.
Figure 35B:
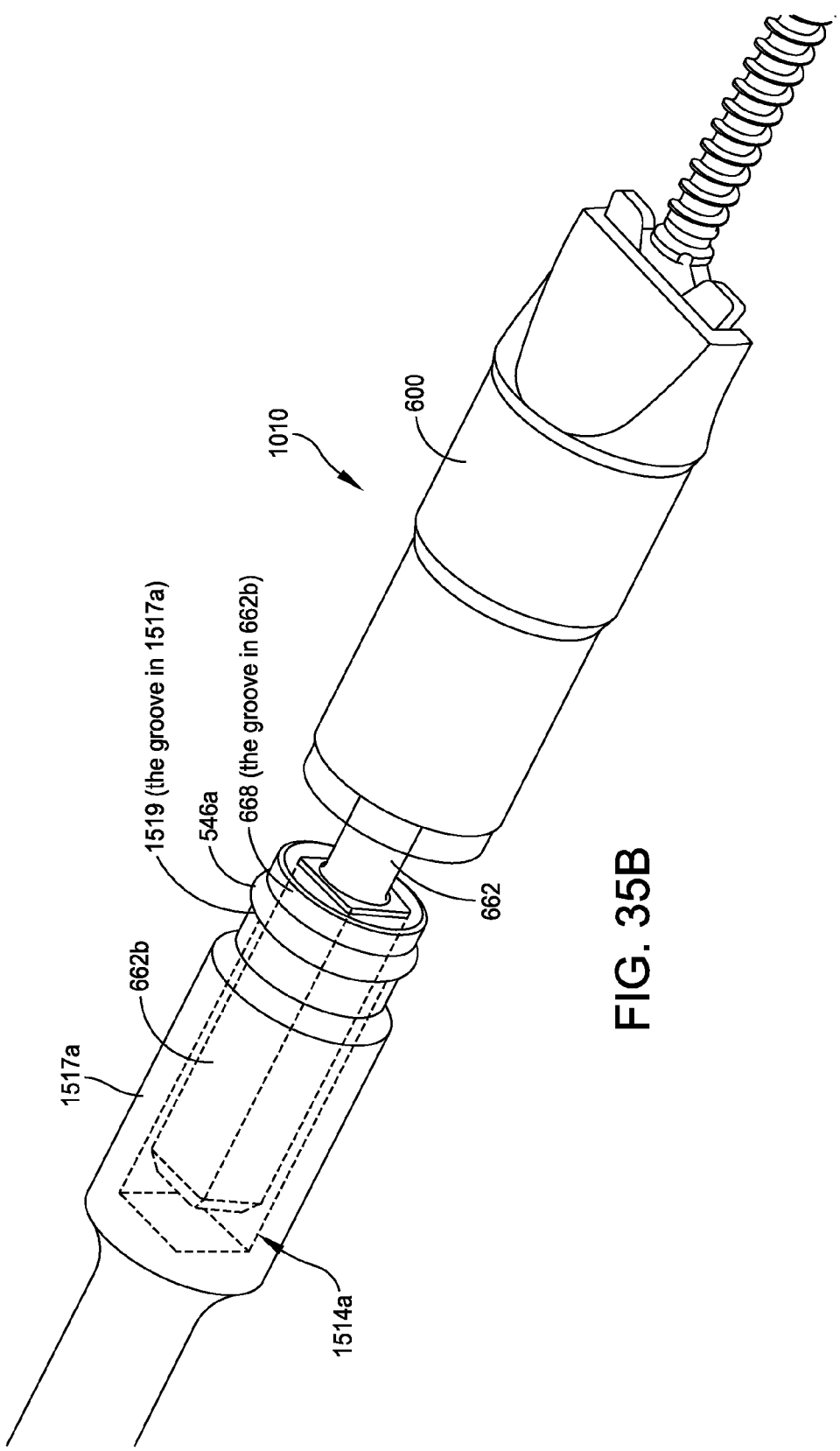

According to another embodiment, FIGS. 35A and 35B show the implant kit 1010 (shown in FIG. 23A) whose driver shaft coupling end 662b is configured to couple to the driver shaft 516 by an O-ring similar to the structure shown in connection with the implant kit 1040 (shown in FIG. 27A). In this embodiment, however, the structures of the adapter-engaging end 1517a of the driver shaft 516 and the driver shaft coupling end 662b of the adapter 600 are switched compared to the structures shown in FIG. 27A. Here, the driver shaft coupling end 662b is configured for coupling to the driver shaft 516 by an O-ring 546a that is provided on the driver shaft rather than the driver shaft coupling end 662b of the adapter's stem portion 662. The adapter-engaging end 1517a of the driver shaft 516 is cylindrical and is provided with a bore 1514a for receiving the driver shaft coupling end 662b. The adapter-engaging end 1517a is provided with a circumferential groove 1519 for accommodating the O-ring 546a. The driver shaft coupling end 662b is configured to be a prism-like structure having a square cross-section or some other polygon cross-section and the bore 1514a has a corresponding shape for receiving the polygon shape. This configuration allows torsional force from the driver shaft 516 to be transferred to the driver shaft coupling end 662b.

Because the adapter-engaging end 1517a is a cylinder, the corners of the polygon shaped driver shaft coupling end 662b are closer to the outer surface of the adapter-engaging end 1517a and the corners of the polygon shaped driver shaft coupling end 662b intersect the bottom of the circumferential groove 1519. This creates openings at the bottom of the groove 1519 that expose the driver shaft coupling end 662b when the driver shaft coupling end 662b is inserted into the bore 1514a. The driver shaft coupling end 662b is provided with a groove 668 that aligns with the circumferential groove 1519 so that the groove 668 is exposed through the openings at the bottom of the groove 1519 and the O-ring 546a provided in the circumferential groove 1519 of the adapter-engaging end 1517a of the driver shaft retains the driver shaft coupling end 662b in place.

Figure 36:
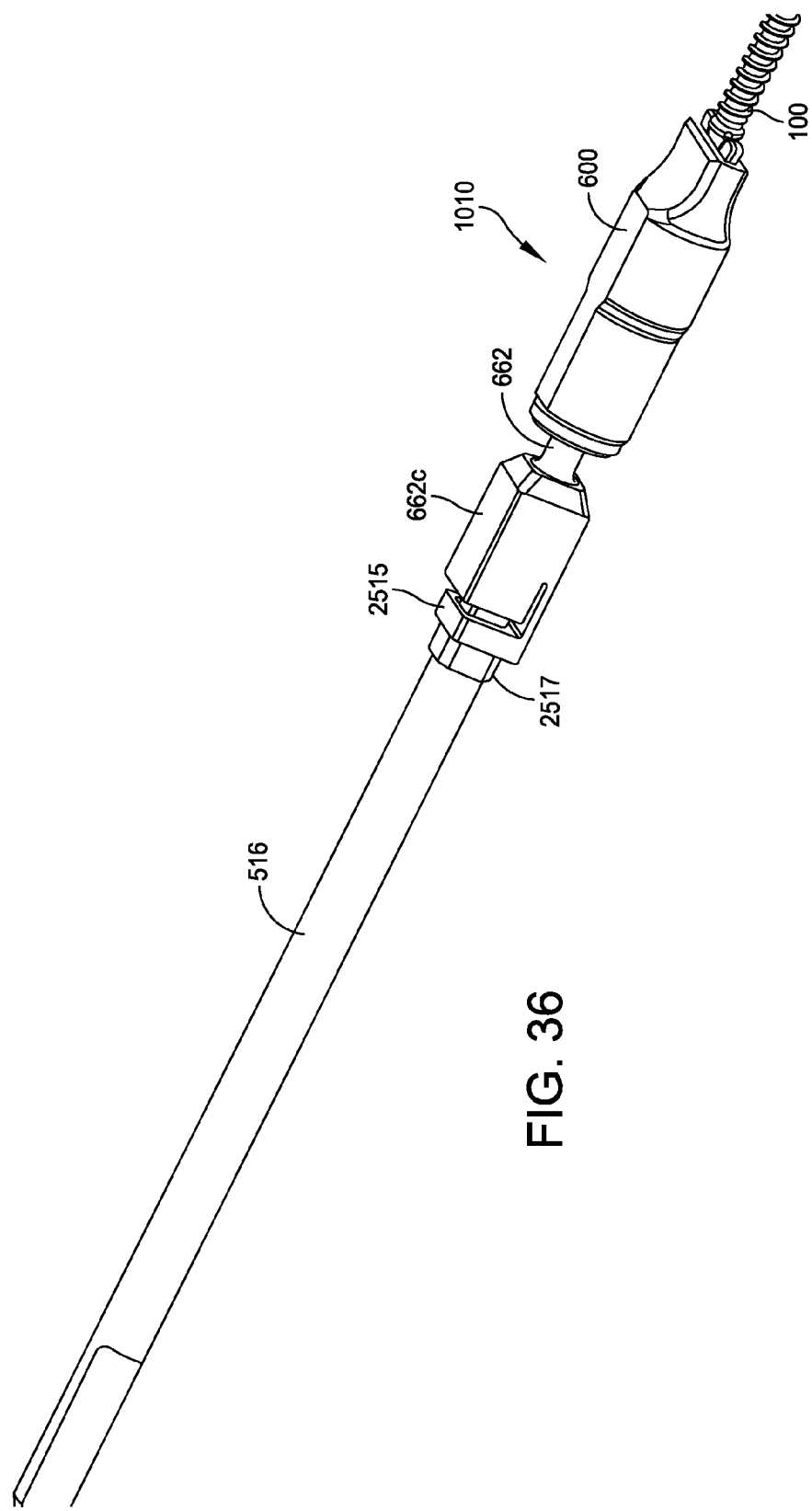
FIG. 36 shows an embodiment of the implant kit comprising an adapter having an implant receiving end configured according to the adapter of FIG. 23A and having a driver shaft coupling end configured for coupling to the driver shaft by an off-set clip shown in the implant kit of FIGS. 28A-28C.

FIG. 36 shows another embodiment of the implant kit 1010 as shown in FIG. 23A that is removably coupled to the driver shaft 516. In this embodiment, the adapter 600 has an implant receiving end structure as shown in FIG. 23A and a driver shaft coupling end 662c that is configured with the off-set clip structure 2515 for coupling to the adapter-engaging end 2517 of the driver shaft 516. The off-set clip structure 2515 is as used in the implant kit 1050 as shown in FIGS. 28A-28C.

Figure 37:
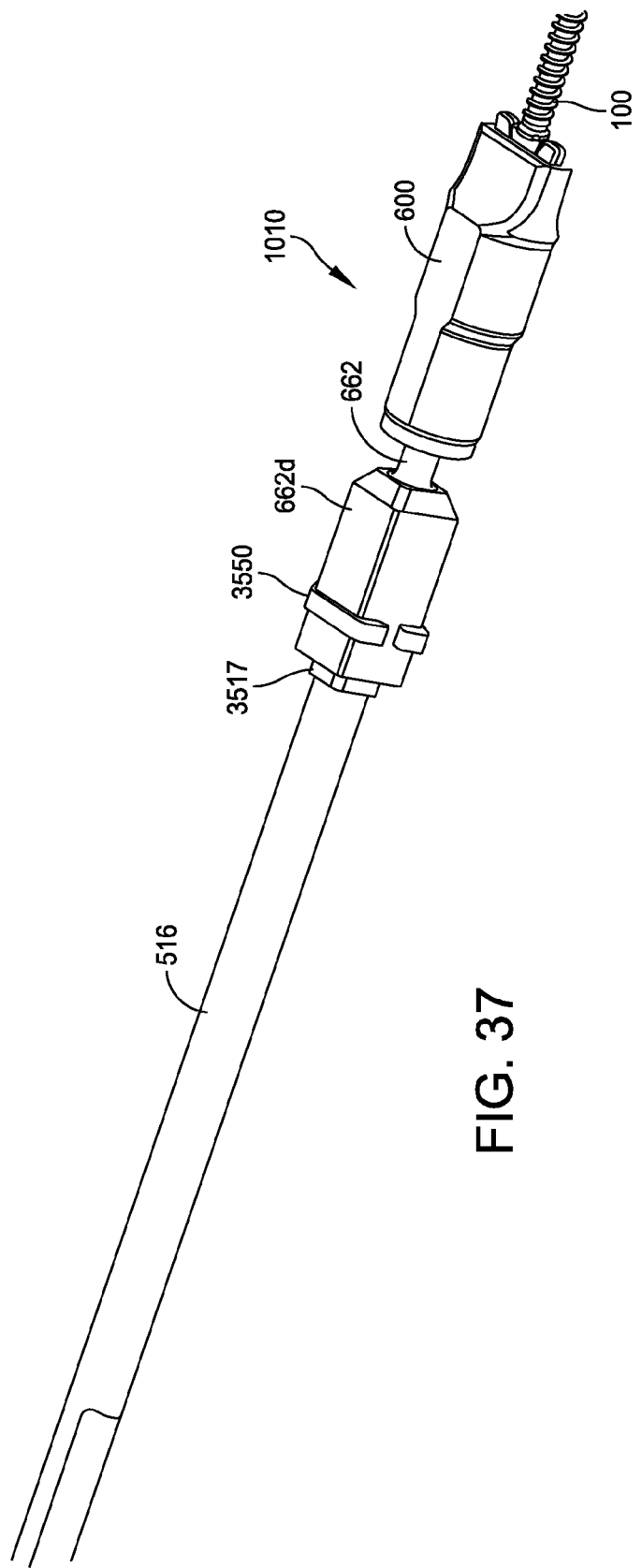
FIG. 37 shows an embodiment of the implant kit comprising an adapter having an implant receiving end configured according to the adapter of FIG. 23A and having a driver shaft coupling end configured for coupling to the driver shaft by the C-clip shown in FIGS. 29A-29E.

FIG. 37 shows another embodiment of the implant kit 1010 as shown in FIG. 23A that is removably coupled to the driver shaft 516. In this embodiment, the adapter 600 has an implant receiving end structure as shown in FIG. 23A and a driver shaft coupling end 662d that is configured with the C-clip structure 3550 as shown in FIGS. 29A-29E for coupling to the adapter-engaging end 3517 of the driver shaft 516.

FIG. 38 shows an embodiment where the implant kit 1030 of FIGS. 25A-25D whose driver shaft coupling end 2663a is configured with the pair of opposing tabs 541, 542 as shown in FIGS. 26A-26D and the adapter-engaging end of the driver shaft 516 is configured to have the structures of 517a or 517b as shown in FIGS. 26A-26D.

Figure 39B:
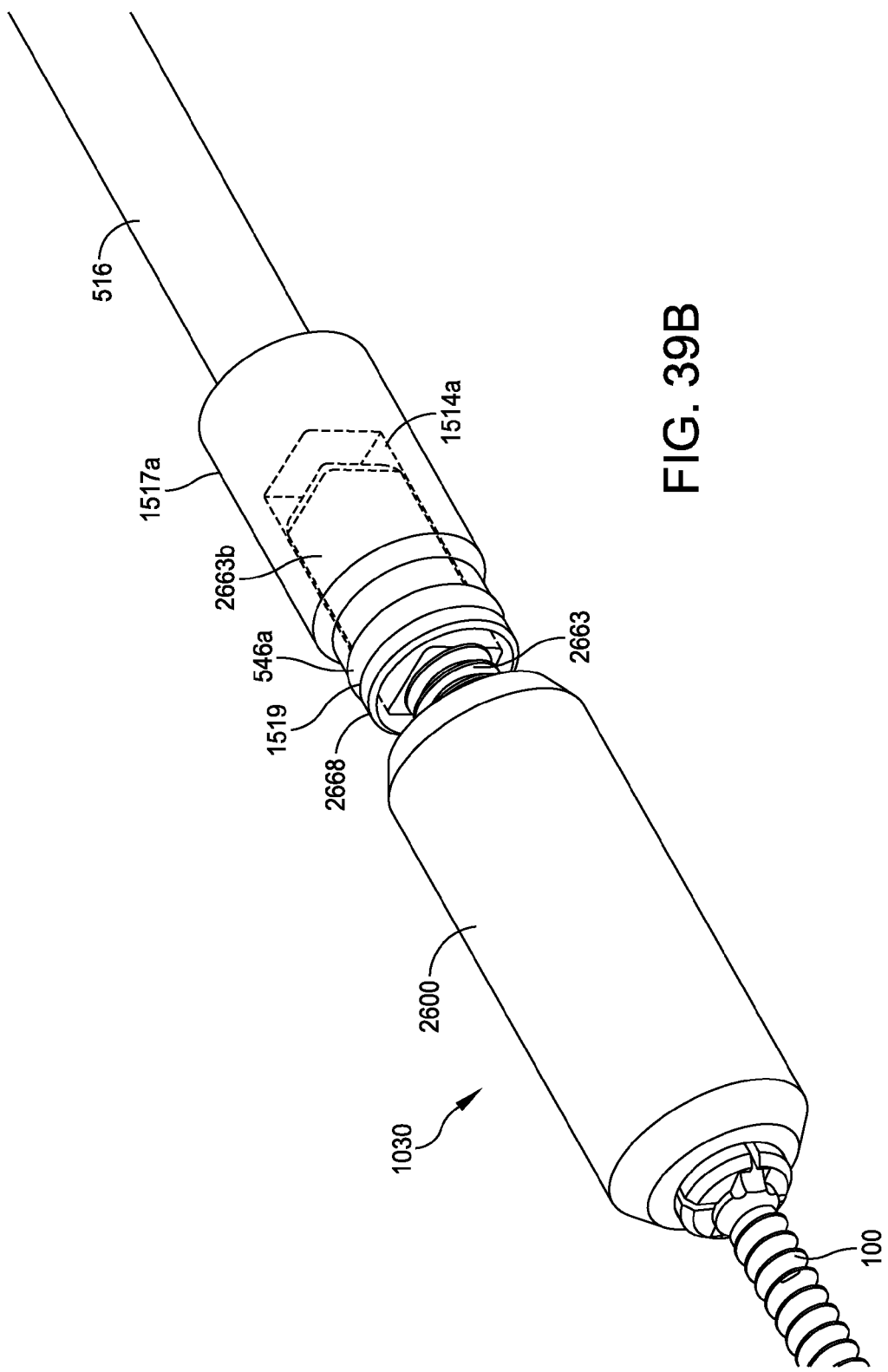

FIGS. 39A-39B show the implant kit 1030 (shown in FIGS. 25A-25D) whose driver shaft coupling end 2663b is configured to couple to the driver shaft 516 by an O-ring similar to the structure shown in connection with the implant kit 1040 (shown in FIG. 27A). In this embodiment, however, the structures of the adapter-engaging end 1517a of the driver shaft 516 and the driver shaft coupling end 2663b of the adapter 2600 are switched compared to the structures shown in FIG. 27A. Here, the driver shaft coupling end 2663b is configured for coupling to the driver shaft 516 by an O-ring 546a that is provided on the driver shaft rather than the driver shaft coupling end 2663b of the adapter's stem portion 2663. The adapter-engaging end 1517a of the driver shaft 516 is cylindrical and is provided with a bore 1514a for receiving the driver shaft coupling end 2663b. The adapter-engaging end 1517a is provided with a circumferential groove 1519 for accommodating the O-ring 546a. The driver shaft coupling end 2663b is configured to be a prism-like structure having a square cross-section or some other polygon cross-section and the bore 1514a has a corresponding shape for receiving the polygon shape. This configuration allows torsional force from the driver shaft 516 to be transferred to the driver shaft coupling end 2663b.

Because the adapter-engaging end 1517a is a cylinder, the corners of the polygon shaped driver shaft coupling end 2663b are closer to the outer surface of the adapter-engaging end 1517a and the corners of the polygon shaped driver shaft coupling end 2663b intersect the bottom of the circumferential groove 1519. This creates openings at the bottom of the groove 1519 that expose the driver shaft coupling end 2663b when the driver shaft coupling end 2663b is inserted into the bore 1514a. The driver shaft coupling end 2663b is provided with a groove 2668 that aligns with the circumferential groove 1519 so that the groove 2668 is exposed through the openings at the bottom of the groove 1519 and the O-ring 546a provided in the circumferential groove 1519 of the adapter-engaging end 1517a of the driver shaft retains the driver shaft coupling end 2663b in place.

FIG. 40 shows another embodiment of the implant kit 1030 as shown in FIGS. 25A-25D that is removably coupled to the driver shaft 516. In this embodiment, the adapter 2600 has an implant receiving end structure as shown in FIG. 23A and a driver shaft coupling end 2663c that is configured with the off-set clip structure 2515 for coupling to the adapter-engaging end 2517 of the driver shaft 516. The off-set clip structure 2515 is as used in the implant kit 1050 as shown in FIGS. 28A-28C.

Figure 41:
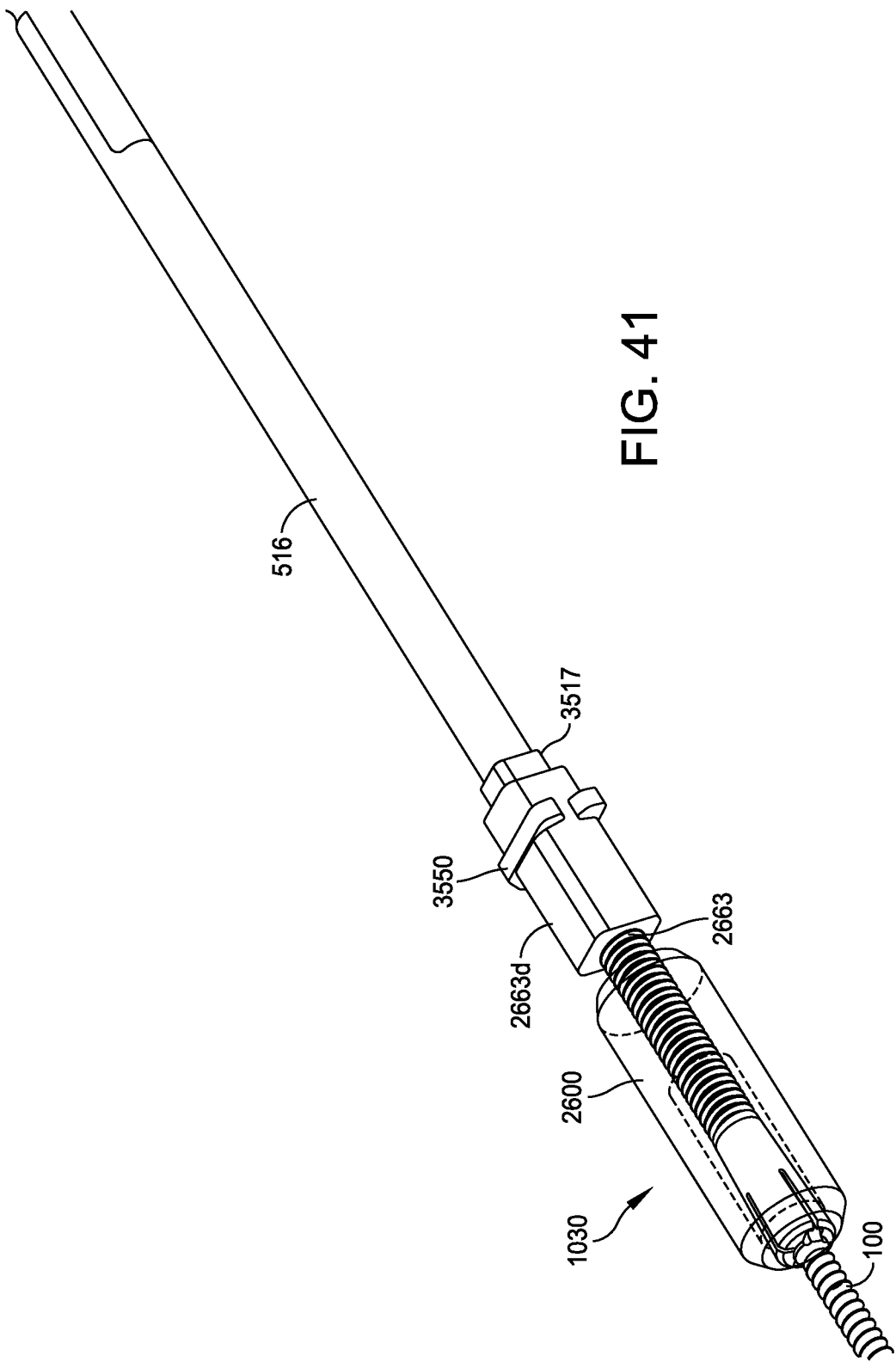
FIG. 41 shows an embodiment of the implant kit comprising an adapter having an implant receiving end configured according to the adapter of FIG. 25A and having a driver shaft coupling end configured for coupling to the driver shaft by a C-clip shown in FIGS. 29A-29E.

FIG. 41 shows another embodiment of the implant kit 1030 as shown in FIGS. 25A-25D that is removably coupled to the driver shaft 516. In this embodiment, the adapter 2600 has an implant receiving end structure as shown in FIG. 23A and a driver shaft coupling end 2663d that is configured with the C-clip structure 3550 as shown in FIGS. 29A-29E for coupling to the adapter-engaging end 3517 of the driver shaft 516.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. An implant kit comprising:
    an adapter having a first end, a second end, and a longitudinal axis extending from the first and to the second end, wherein the first end is configured for removably receiving and engaging an implant and the second end is configured for removably coupling to a driver shaft of an implant driving tool wherein a slot is provided on the first end in which the blade portion of the implant is received; and
    an implant preloaded into the first end of the adapter, said implant comprising:
    an elongated threaded portion;
    a blade portion extending from the elongated threaded portion, and having two serrated edges, wherein the blade portion includes a plurality of teeth along its serrated edges defining valley portions between the plurality of teeth, wherein the blade portion is received in the first end of the adapter and the elongated threaded portion of the implant is coaxially aligned with the longitudinal axis of the adapter;
    wherein a groove is provided on the outer surface of the adapter in proximity to the first end and extending circumferentially around the adapter, wherein the groove is located at a distance from the first end and in alignment with one of the valley portions on the blade, and wherein an elastic O-ring is disposed in the groove and directly engaging the teeth by being positioned within the one of the valley portions and retaining the implant within the slot of the adapter; and
    wherein the first end of the adapter comprises a sleeve having a first open end and a second open end with a bore longitudinally extending through the sleeve between the two open ends, and a collet received in the bore, the collet including an implant receiving portion and a threaded portion, the implant receiving portion having an implant-receiving opening, the implant-receiving opening defined by a plurality of collet segments which is defined by slots extending from the implant-receiving end towards the threaded portion.

2. The implant kit of claim 1, wherein the blade portion of the implant extends from the elongated threaded portion at an angle with respect to the longitudinal axis of the adapter and the slot extends into the adapter at said angle with respect to the longitudinal axis of the adapter.

3. The implant kit of claim 2, wherein the angle is between zero and 45 degrees.

4. The implant kit of claim 1, wherein the first end of the adapter comprising:
    an adapter body having a first end and a second end;
    a slot provided within the adapter body, extending longitudinally therein and open at the first end of the adapter body; and
    a bifurcated clip having a stem portion and a pair of bifurcated arms received within the slot wherein the stem portion extends through the second end of the adapter body and the bifurcated clip is slidable within the slot between an extended position and a retracted position, wherein the bifurcated clip is in the retracted position in which the bifurcated arms are in a closed position with the blade portion of the implant received through the slot and being held between the pair of bifurcated arms.

5. The implant kit of claim 4, wherein the bifurcated clip is spring-biased for keeping the bifurcated clip in the retracted position.

6. The implant kit of claim 5, wherein the implant can be released by sliding the bifurcated clip to its extended position.

7. The implant kit of claim 4, wherein the bifurcated clip is thread-biased for keeping the bifurcated clip in the retracted position.

8. The implant kit of claim 7, wherein the second end of the adapter body comprises a retaining nut that is rotatable about the longitudinal axis, the retaining nut having a threaded bore extending along the longitudinal axis,
    wherein the stem portion of the bifurcated clip has a screw threaded portion that extends through the threaded bore of the retaining nut,
    whereby the bifurcated clip is moved between the extended position and the retracted position by rotating the retaining nut.

9. The implant kit of claim 1, wherein the second end of the adapter is provided with a longitudinally extending bore for receiving the driver shaft;
    a groove provided in the outer surface of the adapter in proximity to the second end and extending circumferentially around the adapter; and
    an elastic O-ring disposed in the groove for coupling the implant kit to the driver shaft when the driver shaft is received in the bore.

10. The implant kit of claim 3, wherein the driver shaft has an adapter-engaging end and the second end of the adapter comprises:
    a longitudinally extending bore for receiving the adapter-engaging end of the driver shaft; and
    a pair of opposing tabs for removably coupling the driver shaft to the adapter, the opposing tabs longitudinally extending away from the first end of the adapter.

11. The implant kit of claim 1, wherein the adapter-engaging end is provided with screw threads and the longitudinally extending bore is tapped with corresponding screw threads whereby the adapter-engaging end and the longitudinally extending bore can be threadably coupled.

12. The implant kit of claim 1, wherein the adapter-engaging end is magnetized and a magnet is provided within the longitudinally extending bore, whereby the adapter-engaging end and the longitudinally extending bore can be magnetically coupled.

13. The implant kit of claim 1, wherein the driver shaft has an adapter-engaging end and the second end of the adapter comprises:
    a longitudinally extending bore for receiving the adapter-engaging end of the driver shaft; and
    an off-set clip cantilevered to the adapter for removably coupling the driver shaft to the adapter, wherein the off-set clip has a deflectable cantilever portion.

14. The implant kit of claim 13, wherein the off-set clip has a through hole that is in an off-set alignment with the longitudinally extending bore, whereby by deflecting the cantilever portion, the through hole can be brought in linear alignment with the longitudinally extending bore and allow the adapter-engaging end of the driver shaft to be inserted through the through hole and into the longitudinally extending bore.

15. The implant kit of claim 1, wherein the driver shaft has an adapter-engaging end and the second end of the adapter is configured to removably couple to the adapter-engaging end of the driver shaft by a C-clip.

16. The implant kit of claim 15, wherein the adapter comprises:
- a longitudinally extending bore for receiving the adapter-engaging end of the driver shaft;
- a pair of grooves for receiving the C-clip, where one groove is provided on each opposing side of the second end; and
- a C-clip for clipping on to the adapter by slidingly engaging the pair of grooves, whereby when the adapter-engaging end of a driver shaft is inserted into the longitudinally extending bore, sliding the C-clip onto the pair of grooves couples the driver shaft to the adapter.

* * * * *